(12) United States Patent
Schreck

(10) Patent No.: US 12,740,880 B2
(45) Date of Patent: Sep. 22, 2026

(54) DEVICES AND METHODS FOR TREATING BRANCHING BLOOD VESSELS

(71) Applicant: Restore Endosystems, LLC, Trabuco Canyon, CA (US)

(72) Inventor: Stefan Georg Schreck, Duvall, WA (US)

(73) Assignee: Restore Endosystems, Inc., South Jordan, UT (US)

( * ) Notice: Subject to any disclaimer, the term of this patent is extended or adjusted under 35 U.S.C. 154(b) by 962 days.

(21) Appl. No.: 17/929,260

(22) Filed: Sep. 1, 2022

(65) Prior Publication Data

US 2023/0144448 A1 May 11, 2023

Related U.S. Application Data

(63) Continuation of application No. PCT/US2021/054258, filed on Oct. 8, 2021.

(60) Provisional application No. 63/089,411, filed on Oct. 8, 2020, provisional application No. 63/195,589, filed on Jun. 1, 2021, provisional application No. 63/240,508, filed on Sep. 3, 2021.

(51) Int. Cl.

| | |
|---|---|
| ***A61F 2/958*** | (2013.01) |
| ***A61F 2/954*** | (2013.01) |
| ***A61F 2/962*** | (2013.01) |
| ***A61M 25/10*** | (2013.01) |

(52) U.S. Cl.
CPC .............. *A61F 2/958* (2013.01); *A61F 2/954* (2013.01); *A61F 2/962* (2013.01); *A61F 2250/0039* (2013.01); *A61M 2025/1045* (2013.01)

(58) Field of Classification Search
CPC ........ A61F 2/07; A61F 2/9522; A61F 2/9524; A61F 2/9525; A61F 2/9526; A61F 2/954; A61F 2/958; A61M 2025/1045; A61M 25/1011
See application file for complete search history.

(56) References Cited

U.S. PATENT DOCUMENTS

| | | | |
|---|---|---|---|
| 4,776,337 | A | 10/1988 | Palmaz et al. |
| 5,735,892 | A | 4/1998 | Myers et al. |
| 5,824,055 | A | 10/1998 | Spiridigliozzi et al. |
| 6,017,324 | A | 1/2000 | Tu et al. |
| 6,045,557 | A | 4/2000 | White et al. |

(Continued)

FOREIGN PATENT DOCUMENTS

| | | | |
|---|---|---|---|
| CN | 102470029 | A | 5/2012 |
| EP | 0965311 | A2 | 12/1999 |

(Continued)

OTHER PUBLICATIONS

European Search Report dated Aug. 22, 2024 for EP21870220.7.

(Continued)

*Primary Examiner* — Sarah W Aleman
(74) *Attorney, Agent, or Firm* — Dorsey & Whitney LLP

(57) ABSTRACT

Described herein are systems and methods for the treatment of branching blood vessels. The system can be introduced percutaneously or by surgical cutdown into a patient's arterial system. The bifurcation from the aorta to the iliac arteries (aortic bifurcation) is used as an example of a branching blood vessel which can be treated with the systems described herein. Also, described herein are methods for assembling the medical devices.

16 Claims, 60 Drawing Sheets

(56) References Cited

U.S. PATENT DOCUMENTS

| | | | | |
|---|---|---|---|---|
| 6,086,611 | A * | 7/2000 | Duffy | A61F 2/82 623/1.35 |
| 6,099,497 | A * | 8/2000 | Adams | A61F 2/958 604/103.05 |
| 6,165,195 | A | 12/2000 | Wilson | |
| 6,355,061 | B1 | 3/2002 | Quiachon et al. | |
| 6,537,284 | B1 | 3/2003 | Inoue | |
| 6,558,396 | B1 | 5/2003 | Inoue | |
| 7,959,667 | B2 * | 6/2011 | Ta | A61F 2/91 623/1.35 |
| 8,257,431 | B2 | 9/2012 | Henderson et al. | |
| 9,539,083 | B2 | 1/2017 | Krimsky et al. | |
| 10,219,926 | B2 * | 3/2019 | Bourang | A61F 2/9524 |
| 2002/0077692 | A1 | 6/2002 | Besselink | |
| 2004/0049204 | A1 | 3/2004 | Harari et al. | |
| 2004/0127850 | A1 | 7/2004 | Steadham et al. | |
| 2004/0148007 | A1 * | 7/2004 | Jackson | A61F 2/95 623/1.12 |
| 2004/0176837 | A1 | 9/2004 | Atladottir et al. | |
| 2005/0043784 | A1 | 2/2005 | Yampolsky et al. | |
| 2005/0149168 | A1 | 7/2005 | Gregorich | |
| 2005/0192656 | A1 | 9/2005 | Eidenschink | |
| 2005/0228472 | A1 | 10/2005 | Case et al. | |
| 2006/0212113 | A1 | 9/2006 | Shaolian et al. | |
| 2007/0118165 | A1 | 5/2007 | Demello et al. | |
| 2007/0142819 | A1 | 6/2007 | El-Nounou et al. | |
| 2007/0168020 | A1 | 7/2007 | Brucker et al. | |
| 2007/0213802 | A1 | 9/2007 | Von et al. | |
| 2007/0270769 | A1 | 11/2007 | Wilson et al. | |
| 2007/0299495 | A1 | 12/2007 | Zukowski et al. | |
| 2008/0051869 | A1 * | 2/2008 | Yribarren | A61F 2/954 623/1.11 |
| 2008/0103587 | A1 | 5/2008 | Henderson et al. | |
| 2008/0114438 | A1 | 5/2008 | Hartley et al. | |
| 2008/0125847 | A1 * | 5/2008 | Krever | A61F 2/958 623/1.11 |
| 2008/0133000 | A1 | 6/2008 | Molony | |
| 2009/0012601 | A1 | 1/2009 | Siu et al. | |
| 2009/0124968 | A1 | 5/2009 | Goshgarian | |
| 2009/0204083 | A1 | 8/2009 | ODonnell et al. | |
| 2009/0259288 | A1 | 10/2009 | Wijay et al. | |
| 2009/0259293 | A1 | 10/2009 | Moloney | |
| 2010/0106238 | A1 | 4/2010 | Hilaire et al. | |
| 2011/0208286 | A1 | 8/2011 | Ta et al. | |
| 2013/0053940 | A1 | 2/2013 | Suhr | |
| 2013/0123907 | A1 | 5/2013 | Roeder et al. | |
| 2013/0184810 | A1 | 7/2013 | Hall et al. | |
| 2013/0296997 | A1 | 11/2013 | Kamat | |
| 2014/0214002 | A1 | 7/2014 | Lieber et al. | |
| 2014/0277353 | A1 | 9/2014 | Hartley | |
| 2014/0324150 | A1 | 10/2014 | Stephens et al. | |
| 2015/0126986 | A1 * | 5/2015 | Kelly | A61B 18/02 606/23 |
| 2015/0250579 | A1 | 9/2015 | Howard et al. | |
| 2015/0289875 | A1 | 10/2015 | Consigny et al. | |
| 2017/0007431 | A1 | 1/2017 | Al-Saadon | |
| 2018/0015264 | A1 | 1/2018 | Wang et al. | |
| 2020/0375724 | A1 | 12/2020 | Perkins et al. | |
| 2021/0401566 | A1 | 12/2021 | Geusen et al. | |
| 2022/0387200 | A1 * | 12/2022 | Kamat | A61F 2/954 |
| 2023/0190501 | A1 | 6/2023 | Schreck | |
| 2023/0210679 | A1 | 7/2023 | Schreck | |
| 2024/0156622 | A1 | 5/2024 | Hall et al. | |
| 2024/0156627 | A1 | 5/2024 | Adams et al. | |

FOREIGN PATENT DOCUMENTS

| | | | | |
|---|---|---|---|---|
| EP | 1920734 | A2 | 5/2008 | |
| EP | 2068761 | B1 | 2/2019 | |
| JP | 2003502080 | A | 1/2003 | |
| WO | 2000027307 | | 5/2000 | |
| WO | WO-0143665 | A2 * | 6/2001 | A61F 2/958 |
| WO | 2009131309 | A2 | 10/2009 | |
| WO | 2022060994 | A1 | 3/2022 | |

OTHER PUBLICATIONS

Extended European Search Report dated Sep. 24, 2025 for EP22908768.9.

Office Action dated Oct. 14, 2025 for U.S. Appl. No. 18/067,321.

Office Action dated Nov. 4, 2025 for U.S. Appl. No. 18/177,027.

Partial European Search Report dated Sep. 25, 2024 for EP21878652.3.

International Search Report and Written Opinion dated Mar. 20, 2024 for PCT/US2023/079678.

International Search Report and Written Opinion dated Apr. 24, 2024 for PCT/US2023/079627.

International Search Report and Written Opinion dated Jan. 14, 2022 for PCT/US2021/054258.

International Search Report and Written Opinion dated Feb. 4, 2022 for PCT/US2021/050688.

International Search Report and Written Opinion dated Apr. 19, 2023 for PCT/US2022/081847.

European Search Report dated Dec. 16, 2024 for EP21878652.3.

Office Action dated Mar. 11, 2026 for U.S. Appl. No. 18/508,539.

Notice of Allowance dated Mar. 16, 2026 for U.S. Appl. No. 18/177,027.

Notice of Allowance dated Mar. 25, 2026 for U.S. Appl. No. 18/067,321.

Office Action dated Mar. 24, 2026 for U.S. Appl. No. 18/509,005.

Office Action dated Aug. 4, 2026 for U.S. Appl. No. 18/508,539.

* cited by examiner

| Infrarenal Aortic Diameter [mm] | Iliac Diameter [mm] | Proximal Balloon Diameter [mm] | Distal Balloon Diameter [mm] | Sleeve Diameter [mm] |
|---|---|---|---|---|
| 10 | 6.3 | 6.3 | 8.2 | 10 |
| 11 | 6.9 | 6.9 | 9.0 | 11 |
| 12 | 7.6 | 7.6 | 9.8 | 12 |
| 13 | 8.2 | 8.2 | 10.6 | 13 |
| 14 | 8.8 | 8.8 | 11.5 | 14 |
| 15 | 9.5 | 9.5 | 12.3 | 15 |
| 16 | 10.1 | 10.1 | 13.1 | 16 |

| $D_A$ | $D_B$ | $D_C$ |
|---|---|---|
| 7 mm | 12 mm | 14 mm |
| 8 mm | 13 mm | 15 mm |
| 9 mm | 14 mm | 16 mm |
| 10 mm | 15 mm | 17 mm |
| 11 mm | 16 mm | 18 mm |
| 12 mm | 17 mm | 19 mm |
| | 18 mm | 20 mm |

| $D_P$ | $D_{D1}$ | $D_{D2}$ |
|---|---|---|
| 7 mm | 6mm, 7mm, 8mm | 5mm, 6mm, 7mm |
| 8 mm | 7mm, 8mm, 9mm | 5mm, 6mm, 7mm, 8mm |
| 9 mm | 8mm, 9mm, 10mm | 5mm, 6mm, 7mm, 8mm, 9mm |
| 10mm | 9mm, 10mm, 11mm | 5mm, 6mm, 7mm, 8mm 9mm, 10mm |

DEVICES AND METHODS FOR TREATING BRANCHING BLOOD VESSELS

CROSS REFERENCE TO RELATED APPLICATIONS

This application is a continuation of PCT/US2021/054258, filed on Oct. 8, 2021 and titled "Devices and Methods for Treating Branching Blood Vessels," which is hereby incorporated by reference in its entirety. PCT/US2021/054258 claims the benefit of U.S. Provisional Patent Application Ser. No. 63/089,411, filed Oct. 8, 2020, U.S. Provisional Patent Application Ser. No. 63/195,589, filed Jun. 1, 2021, and U.S. Provisional Patent Application Ser. No. 63/240,508, filed Sep. 3, 2021, the entire disclosures of all of which are incorporated herein by reference.

FIELD

Medical devices and methods for treating branching blood vessels are described herein. Also, described herein are methods for assembling the medical devices.

BACKGROUND

Aorto-iliac occlusive disease (AIOD) refers to narrowing or stenosis of the blood vessels involving the infrarenal aorta and the two iliac arteries. In complex cases the aorto-iliac bifurcation may be involved.

Balloon angioplasty and placement of bare or covered stents are current methods of treating local narrowing or occlusions of arteries. The "kissing-balloon" technique, the "kissing-stent" technique, and the Covered Endovascular Reconstruction of Aortic Bifurcation (CERAB) technique have been developed to treat AOID involving the aorto-iliac bifurcation. These three methods include simultaneous placement of two parallel "kissing" balloons across the bifurcation. A shortcoming of these techniques is the need for accurate simultaneous placement and inflation of the two kissing balloons. Another shortcoming is that the balloons form a dual double barrel in the aorta and do not conform to the aortic wall. An additional shortcoming of the two-stenting technique is the disruption of the natural blood flow through the bifurcation that can lead to thrombus formation, hemolysis, emboli and restenosis. Another shortcoming is the high technical skill set required to perform these procedures. Even further yet, another shortcoming is that the two stenting technique makes re-intervention procedures using a retrograde approach (up-and-over technique) very challenging.

As an alternative approach, self-expanding bifurcated stent grafts (e.g., AFX device manufactured by Endologix) have been placed to treat complex aorto-iliac disease. The advantage of the bifurcated stent graft is that it preserves the bifurcation avoiding flow disturbances and allowing for a retrograde approach for re-intervention. A shortcoming of this approach is that the self-expanding stent may have insufficient outward force to maintain a patent flow lumen. Another shortcoming is the large profile (cross-sectional area) of the delivery system. A third shortcoming is the exposed stent structures of the AFX device that can lead to flow disruptions, thrombus formation and difficulties with future cross-over interventions. Another shortcoming is the complex procedural steps and high technical skill set that is required to place the AFX device in a diseased aorto-iliac bifurcation. Further yet, another shortcoming is the difficulty to accurately size self-expanding stents to the variability in aortic and iliac diameters, which can lead to infolding and blood flow disturbances and/or a lack of vessel wall apposition. Other self-expanding abdominal aortic aneurysm stent grafts are sometimes used to treat aorto-iliac occlusive disease, but they have similar shortcomings as the AFX system.

There is a need for medical devices and methods for the treatment of AIOD involving the aorto-iliac bifurcation that overcome the above listed shortcomings of existing methods.

BRIEF SUMMARY OF THE INVENTION

Described herein are systems and methods for the treatment of branching blood vessels. The system can be introduced percutaneously or by surgical cutdown into a patient's arterial system. The bifurcation from the aorta to the iliac arteries (aortic bifurcation) is used as an example of a branching blood vessel which can be treated with the systems described herein. It is understood that the application of the systems described herein are not limited to the aortic bifurcation. The systems and methods of use described herein can be applied to any branching or bifurcated artery, vein, or airway in a body. In some embodiments, the body is the body of a mammal. In other embodiments, the mammal is a human. The words systems, devices, medical devices, and/or apparatuses are used herein interchangeably.

For consistency, when describing the systems, the direction toward the external end of the system outside the body is referred to as "proximal" and the direction away from the external end of the system is referred to as "distal". The side on which the system is inserted into the arteries is referred to as "ipsilateral", the opposite side is referred to as "contralateral". For example, if the system is inserted into an artery of the right leg, the right side of the body is referred to as ipsilateral and the right iliac artery is referred to as the ipsilateral iliac artery. The left side is referred to as contralateral and the left iliac artery is referred to as the contralateral iliac artery.

In some embodiments, a system comprising a balloon catheter including two parallel arranged balloons is described herein. In other embodiments, a systems comprising a balloon catheter including two parallel arranged balloons to perform a "kissing balloon" angioplasty of an aorto-iliac bifurcation is described. The balloons can be rigid or semi-rigid. In some embodiments, the balloons can be drug eluting. The balloons can be cutting or scoring balloons. In other embodiments, the balloon catheter can also include at least one or more lithotripsy emitters.

In some embodiments, a system comprises a balloon catheter including two balloons, a first balloon and a second balloon. The first balloon can be at least partially placed in the ipsilateral iliac artery. In other embodiments, the first balloon can be completely placed in the ipsilateral iliac artery. In some embodiments, the first balloon also be referred to as an ipsilateral balloon. The second balloon can be at least partially placed in the contralateral iliac artery. In other embodiments, the second balloon can be completely placed in the contralateral iliac artery. In some embodiments, the second balloon can be referred to as a contralateral balloon. The balloon catheter can have a first guidewire lumen for placement of a guidewire from the ipsilateral access point into the aorta. In some embodiments, the balloon catheter can include a second guidewire lumen for placement of a guidewire from the ipsilateral access point into the contralateral iliac artery. In other embodiments, the second guidewire lumen can form a loop in the aorta distal to the first balloon and the second balloon to direct the second guidewire into the contralateral iliac artery. In other embodiments, the system can comprise a balloon catheter including at least two or more balloons, .e.g. a first balloon, a second balloon, and a third balloon. In some embodiments, the system can comprise a balloon catheter including at two or more balloons, .e.g. a first balloon, a second balloon, a third balloon, and a fourth balloon.

In some embodiments, the balloon catheter can include a proximal hub with an inflation port that is in fluid communication with the first balloon and a distal hub which is in fluid communication with the first balloon and the second balloon enabling inflation of the two balloons from a single inflation port. In some embodiments, the distal hub can be connected to the first balloon and the second balloon by at least one or more flexible tube(s). In other embodiments, the distal hub can further include lumens for the first guidewire and the second guidewire.

In some embodiments, the proximal segments of the first balloon and the second balloon can be placed in the iliac arteries, and the distal segments of the first balloon and the second balloon can be placed in the aorta. In other embodiments, the expansion of the distal segments of the first balloon and the second balloon can be constrained by a tubular constraining sleeve. The diameter of the constraining sleeve can be less than 1.6 times the diameter of the distal segments of the first balloon and the second balloon. In some embodiments, the diameter of the constraining sleeve can be about 1.2-1.4 times the diameter of the distal segments of the first balloon and the second balloon. In other embodiments, when the balloons are inflated, the constraining sleeve can have an oval or circular cross-sectional profile. The balloon segments constrained by the sleeve can have non-circular cross-sectional profiles.

In some embodiments, the proximal segments of the first balloon and the second balloon that are placed in the iliac arteries can have a smaller diameter than the distal segments of the first balloon and the second balloon that are placed in the aorta. In other embodiments, the proximal segments of the first balloon and the second balloon can have a diameter of about 75%-85% of the distal segments of the balloons. In some embodiments, the balloons can have a further reduced diameter between the proximal and distal segments to increase the bending flexibility of the balloon(s) when inflated.

In some embodiments, the balloon catheter can include a tether connected to a free end of the second balloon. The tether can extend from the free end of the second balloon through an opening in the shaft of the catheter proximal to the first balloon to the proximal hub of the catheter. In some embodiments, pulling on the tether at the proximal hub can pull the free end of the second balloon towards the shaft of the balloon catheter.

In some embodiments, the balloon catheter can be used to deliver and deploy a balloon-expandable bifurcated stent into the aortic bifurcation. In other embodiments, the bifurcated stent can include a main body stent and two branch stents. In some embodiments, the bifurcated stent can include a single unibody bifurcated stent. The bifurcated stent can be covered with biocompatible material. In some embodiments, the stent can be covered with a thin sheet of biocompatible material. Biocompatible material such as, but not limited to, polytetrafluroethylene (PTFE), ePTFE, polyurethane, or polyester. The bifurcated stent can be mounted onto the balloon catheter by mounting the first branch stent of the bifurcated stent onto the proximal segment of the first balloon, the second branch stent of the bifurcated stent onto the proximal segment of the second balloon, and the main body of the bifurcated stent onto the distal segments of the first balloon and the second balloon.

Methods of performing a kissing-balloon angioplasty procedure of the aorto-iliac bifurcation are also described herein. The method utilizes an example embodiment of the balloon catheter described above and comprises the following steps:

a) Advancing a first guidewire into a body from an ipsilateral leg artery through the ipsilateral iliac artery into the aorta.
b) Inserting the first guidewire into a first guidewire lumen in the balloon catheter and advancing the balloon catheter over the first guidewire past the aorto-iliac bifurcation into the aorta.
c) Inserting a second guidewire into the proximal end of the second guidewire lumen and advancing the second guidewire through the distal hub and the loop into the contralateral iliac artery.
d) Placing the second balloon at least partially into the contralateral iliac artery by partially retracting the balloon catheter.
e) Injecting fluid into the inflation lumen, simultaneously inflating both the first balloon and the second balloon, and performing an angioplasty of the aortic bifurcation.
f) Withdrawing the fluid from the inflation lumen and collapsing the first balloon and the second balloon.
g) Advancing the catheter until the entire second balloon is within the aorta.
h) Pulling on the tether to pull the second balloon against the shaft of the balloon catheter.
i) Removing the balloon catheter from the body.

The preceding steps do not need to occur in the order presented. Also, in some embodiments not all the steps need to be preformed, e.g. steps can be removed. In other embodiments, additional steps can be preformed, e.g. steps can be added.

Alternatively, the method utilizes an example embodiment of a bifurcated stent and an example embodiment of a catheter described above and comprises the following steps:

a) Mounting a first branch stent of the bifurcated stent onto a proximal segment of a first balloon, a second branch stent of the bifurcated stent graft onto a proximal segment of a second balloon, and a main body stent of the bifurcated stent onto distal segments of the first balloon and the second balloon.
b) Advancing a first guidewire into the body from a leg artery through the ipsilateral iliac artery into the aorta.
c) Inserting the first guidewire into a first guidewire lumen in the balloon catheter and advancing the balloon catheter over the first guidewire past the aorto-iliac bifurcation into the aorta.
d) Inserting a second guidewire into the proximal end of the second guidewire lumen and advancing the guidewire through the distal hub and loop into the contralateral iliac artery.
e) Placing the second balloon partially into the contralateral iliac artery by partially retracting the catheter.
f) Injecting fluid into the inflation lumen, inflating the first balloon and the second balloon, and deploying the bifurcated stent into the aorto-iliac bifurcation.
g) Withdrawing the fluid from the inflation lumen and collapsing the first balloon and second balloon.
h) Advancing the catheter until the entire second balloon is within the aorta.

i) Pulling on the tether to pull the second balloon against the shaft of the balloon catheter.

j) Retracting the balloon catheter through the ipsilateral iliac artery.

k) Removing the balloon catheter from the body.

The preceding steps do not need to occur in the order presented. Also, in some embodiments not all the steps need to be preformed, e.g. steps can be removed. In other embodiments, additional steps can be preformed, e.g. steps can be added.

In some embodiments, the body is a body of a patient or a subject. The patient/subject can be a mammal. In other embodiments, the mammal is a human.

If needed, post-ballooning of the bifurcated stent can be performed to conform the main body stent and the two branch stents to the vessel wall of the aorta and iliac arteries, respectively. The sequence of steps can be altered, steps can be removed, and additional steps can be performed.

Other embodiments of the balloon catheter for placing a bifurcated stent into the aortoiliac bifurcation is described. The balloon catheter can comprise a proximal hub, a proximal and a distal shaft, and a bifurcated balloon assembly located between the proximal shaft and the distal shaft. The bifurcated balloon assembly can comprise at least two cylindrical balloons which are arranged substantially in parallel to each other: a first balloon that is connected on the proximal end to the proximal shaft and on the distal end to the distal shaft, and a second balloon that has a free proximal end and is connected on the distal end to the distal shaft. In some embodiments, the balloon assembly can comprise an additional restraining sleeve that is placed over the distal sections of both balloons. The balloon catheter includes a bifurcated inflation lumen that extends from the proximal hub, through the first balloon into the distal shaft and has a branch from the distal shaft to the second balloon. The bifurcated inflation lumen is connected to an inflation port within the proximal hub and is in fluid communication with the first balloon and the second balloon.

In some embodiments, the balloon catheter can include a second bifurcated lumen that extends from the proximal hub, through the first balloon into the distal shaft and has a branch from the distal shaft through the second balloon. The bifurcated lumen can include a contralateral guidewire comprising a first proximal end that exits the balloon catheter at the proximal hub and a second proximal end that exits the balloon catheter at the free proximal end of the second balloon, and a distal end that is housed within the distal shaft. The first proximal end of the contralateral guidewire can be connected to a guidewire handle. The second proximal end of the contralateral guidewire can be comprised of a flexible radiopaque guidewire tip for atraumatically advancing the contralateral guidewire through the vasculature. Rotating the guidewire handle can rotate the guidewire tip. Moving the handle proximally can move the guidewire tip proximally. Moving the handle distally can move the guidewire tip distally. The balloon catheter can include a third lumen extending from a port in the proximal hub to the distal end of the proximal shaft. The third lumen can house the tip of the contralateral guidewire during device insertion. The third lumen can also provide a pathway for a tether that is connected at its proximal end to a tether handle and on the distal end to the free proximal end of the second balloon. Alternatively, the third lumen can include a snare to capture the tip of the guidewire.

Methods of deploying a balloon-expandable bifurcated stent into the aortic bifurcation are also described herein. The methods utilize an example embodiment of the balloon catheter including a contralateral guidewire as described above and a bifurcated balloon-expandable stent crimped onto the balloon assembly. The main body of the bifurcated stent is crimped onto the distal sections of both balloons. The first branch stent is crimped onto the proximal section of the first balloon and the second branch stent is crimped onto the proximal section of the second balloon. This method comprises the following steps:

a) Advancing a guidewire into a body from an ipsilateral leg artery through the ipsilateral iliac artery into the aorta.

b) Advancing the balloon catheter over the guidewire until the balloon assembly is beyond the aortic bifurcation.

c) Advancing the guidewire handle distally to release the contralateral guidewire from the proximal shaft.

d) Advancing the guidewire handle proximally to advance the contralateral guidewire into the contralateral iliac artery.

e) Advancing the balloon catheter proximally to place the bifurcated stent onto the aortic bifurcation.

f) Injecting fluid into the inflation lumen, inflating the balloon assembly, and deploying the bifurcated stent into the aortic bifurcation.

g) Withdrawing the fluid from the inflation lumen to deflate the balloon assembly.

h) Advancing the balloon catheter distally until the balloon assembly is distal to the aortic bifurcation.

i) Advancing the contralateral guidewire distally until the tip of the contralateral guidewire is distal to the aortic bifurcation.

j) Pulling on the tether to align the free end of the second balloon with the distal end of the proximal shaft.

k) Removing the balloon catheter from the body.

In some embodiments, a self-deploying stent cover is described to protect the contralateral branch stent from dislodging from the balloon assembly during device insertion into the contralateral branch vessel. The self-deploying stent cover can be tubular in shape. The self-deploying stent can be composed from an elastomeric material. In some embodiments, the self-deploying stent is tubular in shape and made from an elastomeric material. The self-deploying stent cover is placed over the distal section of the second balloon covering the distal end of the contralateral branch stent and the distal shoulder of the second balloon. During insertion of the crimped contralateral stent into the contralateral branch vessel, the stent cover prevents the stent from being dislodged when contacting the arterial wall, which can be calcified or occluded. The friction between the self-deploying stent cover and the second balloon is sufficiently low so that the stent cover slips off the proximal end of the contralateral branch stent when the balloon assembly is inflated.

Adaptive bifurcated balloon assemblies are also described herein that allow for independent control of the diameter of the main body segment and at least one branch segment of the balloon assembly during balloon inflation. In some embodiments, the two balloons are non-compliant, and the restraining sleeve is semi-compliant. Inflating the balloon assembly to a first pressure expands the two branch segments of the bifurcated stent to a first diameter and the main body segment of the bifurcated stent to second diameter. Further increasing the inflation pressure from the first pressure to a second pressure does not considerably increase the diameters of the two branch segments beyond the first diameter; but increases the diameter of the main body segment to a third diameter, which can be at least 10% larger than the second diameter. In other embodiments, the first balloon and the restraining sleeve are non-compliant, and the second balloon is semi-compliant. Inflating the bifurcated balloon assembly to a first pressure expands the first branch of the bifurcated balloon assembly to a first diameter, the second branch to a second diameter, and the main body of the bifurcated balloon assembly to a third diameter. Further increasing the inflation pressure from the first pressure to a second pressure does not considerably increase the diameter of the first branch beyond the first diameter and the diameter of the main body beyond the third diameter; but increases the diameter of the second branch to a fourth diameter, which can be at least 10% larger than the second diameter. A bifurcated balloon assembly is considered adaptive if it comprises a first balloon, a second balloon arranged in part substantially parallel to the first balloon, a restraining sleeve partially placed over the first balloon and the second balloon, wherein at least one of the three components is made from non-compliant material and at least one component is made from semi-compliant material. In some embodiments, non-compliant material restricts the expansion of a component to less than 110% of the nominal diameter. In other embodiments, semi-compliant material allows for expansion of the component beyond 110% of the nominal diameter.

In some embodiments, the balloon segments can be inflated by separate inflation lumens which are not in fluid communication with each other. For example, the first balloon is in fluid communication with a first inflation lumen, and the second balloon is in fluid communication with a second inflation lumen. Alternatively, the distal segments of both balloons are in fluid communication with a first inflation lumen, and the proximal segments of both balloons are in fluid communication with a second inflation lumen. The combination of semi-complaint and non-complaint balloon and sleeve material and separate inflation lumens allows for independent control of the diameters of the two branches and the main body of the bifurcated balloon assembly.

In other embodiments, a bifurcated balloon assembly comprises two cylindrical balloons arranged substantially in parallel. In each balloon, a narrowing (or waist) in the center of the balloon divides the balloon into a distal and a proximal segment. A restraining sleeve is mounted over the distal segments of both balloons restraining the expansion of the two distal segments when the balloons are inflated. The restraining sleeve forms the main body of the bifurcated balloon assembly and the proximal segments of the two balloons form the two branches of the bifurcated balloon assembly. The waists in the balloons create flex points in the balloon assembly at the bifurcation.

One application of the bifurcated balloon assembly is the deployment of a balloon-expandable bifurcated stent into the aortic bifurcation. The bifurcated stent can comprise a main body stent and two branch stents. The bifurcated stent can be covered with a biocompatible material such as ePTFE or polyurethane. The branch stents of the bifurcated stent can be crimped onto the proximal segments of the bifurcated balloon assembly, and the main body stent onto the restraining sleeve. When the bifurcated balloon assembly is inflated, the proximal segments of the two balloons expand the two branch stents. The two restrained distal segments of the balloons expand the main body stent into a cylindrical shape.

In some embodiments of the bifurcated balloon assembly, the restraining sleeve is only placed onto the distal section of the distal balloon segments. When the two balloons are inflated, the proximal sections of the distal balloon segments located between the waists and the restraining sleeve are not restrained. A bifurcated stent can be crimped onto the bifurcated balloon assembly with the proximal end of the main body stent aligned with the waists in the two balloons. Inflating the bifurcated balloon assembly expands the bifurcated stent. The branch stents are expanded by the proximal balloon segments. The proximal end of the main body stent is expanded into an oval cross-section by the unconstrained sections of the distal balloon segments. The distal end of the main body stent is expanded into a circular cross-section by the constrained sections of the distal balloon segments. The oval cross-section of the proximal end of the main body stent provides a smooth flow lumen transition from the main body stent into the two branch stents.

In other embodiments of the bifurcated balloon assembly, the distal segments of the two balloons can include a first diameter at the proximal end and a second diameter at the distal end, with the first diameter being equal to the diameter of the proximal segments of the balloon assembly and the second diameter being smaller than the diameter of the proximal segments of the balloon assembly. A bifurcated stent can be crimped onto the bifurcated balloon assembly with the branch stent crimped on the proximal segments of the balloons and the main body stent crimped onto the two distal segments of the balloons. The bifurcated stent can be deployed into the aortic bifurcation of a patient. In one step, the balloon assembly can be placed onto the aortic bifurcation and inflated to expand the branch stents to the diameter of the iliac arteries and the main body stent into an oval cross-section along. In another step, a cylindrical balloon can be placed into the main body stent and inflated to further expand the distal end of the main body stent into a circular cross-section.

Existing methods for crimping a stent onto a balloon are designed for tubular non-bifurcating stents. There is a need for new crimping methods to crimp a bifurcated stent onto a bifurcated balloon assembly. Methods for crimping a bifurcated stent onto a bifurcated balloon assembly are described here. In some embodiments, a method comprises compressing the main body stent and the two branch stents toward their respective centerline, and compressing the main body stent and the two branch stents toward a common centerline.

The method of crimping a bifurcated stent onto a bifurcated balloon assembly can comprise compressing the two branch stents from a first circular cross-section to a second circular cross-section, wherein the second cross-section is smaller than the first cross-section, and compressing the branch stents from the second circular cross-section to a third oval cross-section.

In some embodiments, the method of crimping a bifurcated stent onto a bifurcated balloon assembly can include a crimping tool. A crimping tool can comprise two interlacing parts, the two parts forming a bifurcated channel when interlaced. In some embodiments, a set of crimping tools with progressively smaller channels can be used to stepwise crimp the bifurcated stent from an uncrimped configuration to a crimped configuration.

In other embodiments, the method of crimping a bifurcated stent onto a bifurcated balloon assembly can include the application of heat to the balloon assembly to make the balloon material more compliant. The method of crimping a bifurcated stent onto a bifurcated balloon assembly can comprise a step of inflating the balloons when the stent is restrained by the crimping tool to conform the balloons to the bifurcated stent. The bifurcated balloon assembly can be heated during the inflation step.

BRIEF DESCRIPTION OF DRAWINGS

FIG. 27H illustrates a tether of the balloon catheter of FIG. 26A retracted and the balloons in a parallel configuration.

FIG. 32B illustrates a different slope of the balloon shoulder of FIG. 31A.

FIG. 73A illustrates crimping branches of a bifurcated stent with a single channel crimping tool.

FIG. 73B illustrates further crimping branches of the bifurcated stent of FIG. 73A.

FIG. 73C illustrates further crimping branches of the bifurcated stent of FIG. 73A.

FIG. 74 illustrates a process flow of a crimping process described herein.

DETAILED DESCRIPTION OF INVENTION

Described herein are balloon catheter systems. In some embodiments, a balloon catheter system can comprise at least two hubs, at least two balloons, and a shaft. In other embodiments, a balloon catheter system can comprise at least two hubs, at least two balloons, and a catheter shaft, wherein the last two hubs include a proximal hub and a distal hub, and wherein the at least two balloons include a first balloon and a second balloon. Proximal hub can include one or more ports. The one or more ports can include a guidewire port, an inflation port, a tether port, and/or a combination thereof.

Figure 1:
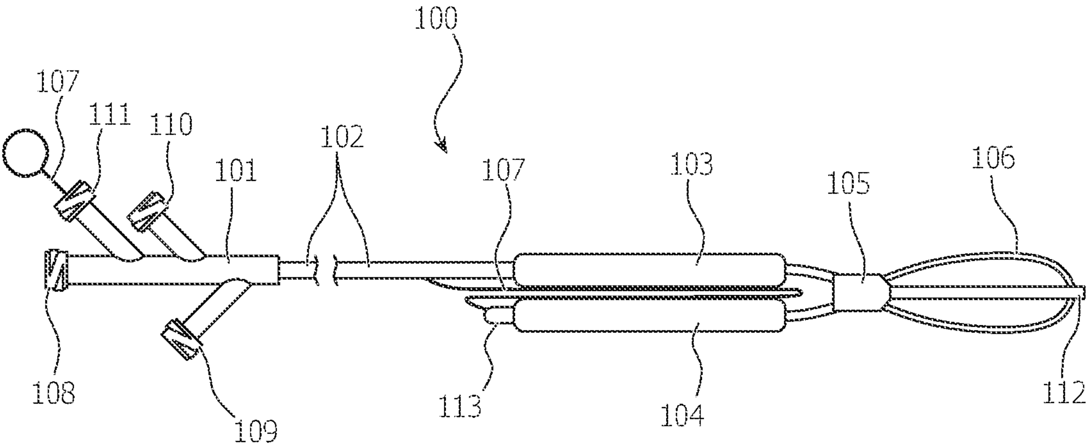
FIG. 1 illustrates a balloon catheter system described herein.

FIG. 1 illustrates an example embodiment of balloon catheter (100). Balloon catheter system (100) comprises proximal hub (101), catheter shaft (102), first balloon (103), second balloon (104), distal hub (105), loop (106), and tether (107). Proximal hub (101) includes first guidewire port (108), second guidewire port (109), inflation port (110), and tether port (111). First balloon (103) and second balloon (104) are arranged in parallel. A first guidewire lumen (not shown) extends from first guidewire port (108) through catheter shaft (102), first balloon (103), and distal hub (105) to distal end (112) of balloon catheter (100). A second guidewire lumen (not shown) extends from second guidewire port (109), through catheter shaft (102), first balloon (103), distal hub (105), into loop (106), and from loop (106) back through distal hub (105) to free end (113) of second balloon (104). Inflation port (110) is in fluid communication with first balloon (103) and second balloon (104). Tether (107) extends from free end (113) of second balloon (104) through the proximal segment of shaft (102) to tether port (111).

Figure 2:
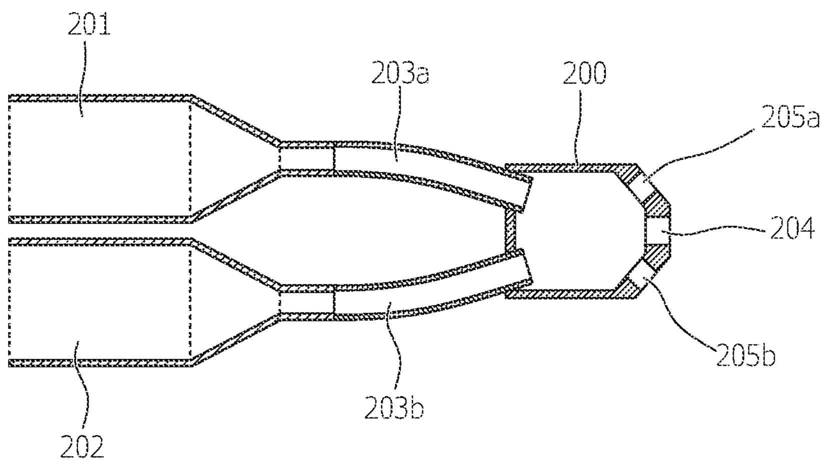
FIG. 2 illustrates a distal segment of a balloon catheter system.

FIG. 2 illustrates a distal hub assembly in more detail. Distal hub (200) is connected to first balloon (201) and second balloon (202) by at least one or more conduits (203*a*-*b*). At least one or more conduits (203*a*-*b*) can be composed of flexible material. The distal end of the distal hub can comprise at least one or more openings. Distal end of distal hub (200) comprises first opening (204). Opening (204) can be configured for passage of an aortic guide wire lumen. In some embodiments, distal hub (200) can comprise first opening (204) and second openings (205*a*-*b*). Second openings (205*a*-*b*) can be configured for passage of a contralateral guidewire loop. As illustrated in FIG. 2, first balloon (201) and second balloon (2002) are in fluid communication with each other and are inflated simultaneously by injecting fluid into the inflation port located at the proximal hub. In some embodiments, each balloon can include a separate inflation port and an inflation lumen connecting each balloon to their respective inflation port to allow for independent inflation of the two balloons.

Figure 3A:
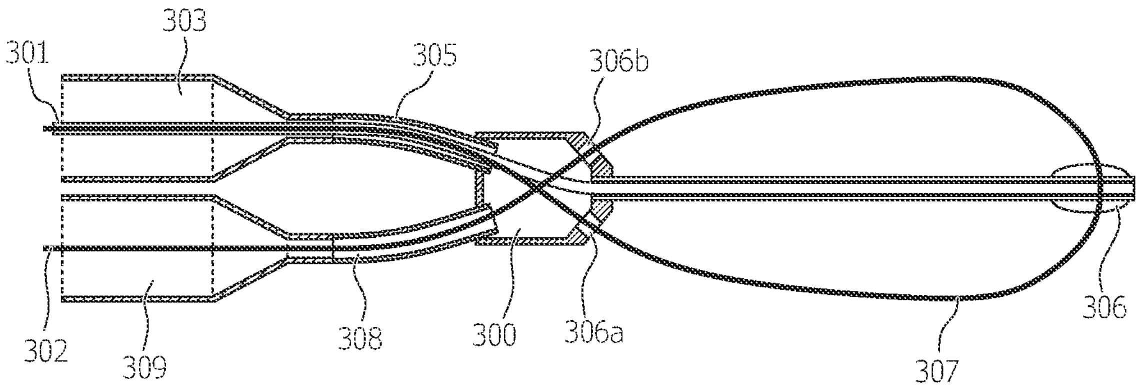
FIG. 3A illustrates guidewire pathways through a distal segment of a balloon catheter system.
Figure 3B:
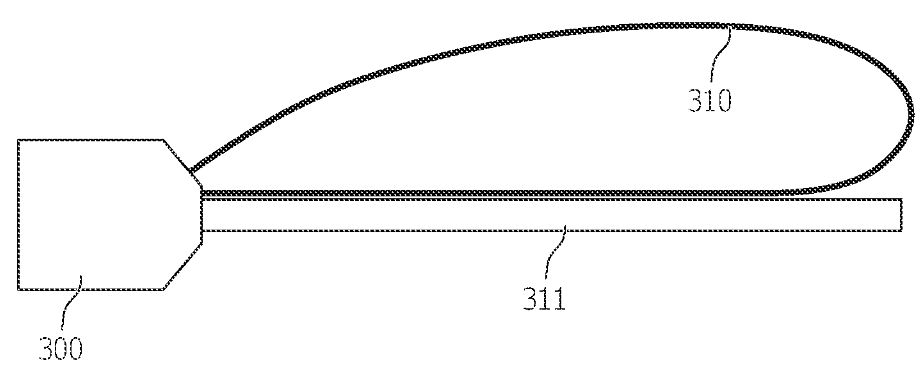
FIG. 3B illustrates guidewire pathways through a distal segment of a balloon catheter system.

FIG. 3A illustrates the routing of first guidewire lumen (301) and second guidewire lumen (302) through distal hub (300). First guidewire lumen (301) passes through first balloon (303) and first flexible conduit (305) and distal hub (300) to catheter tip (306). Second guidewire lumen (302) passes through first balloon (303) and first flexible conduit (305) into distal hub (300). Second guidewire lumen (302) exits hub (300) through first distal opening (306*a*), forms loop (307), and re-enters hub (300) through second distal opening (306*b*). From there, it passes through second flexible conduit (308) and second balloon (309). In some embodiments, the distal end of loop (307) can be secured to catheter tip (306) to prevent collapse of loop (307) during catheter insertion into an introducer sheath, guide catheter, or blood vessel. In other embodiments, as illustrated in FIG. 3B, a portion of loop (310) containing the second guidewire lumen can be routed parallel to first guidewire conduit (311) with loop (310) and first guidewire conduit (311) being connected along a substantial segment of their parallel path.

Figure 4A:
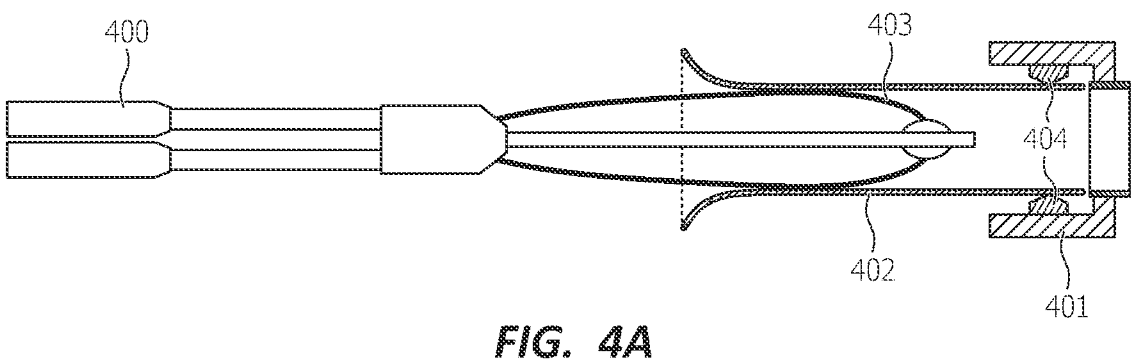
FIG. 4A illustrates placement of a balloon catheter system into an introducer sheath.
Figure 4B:
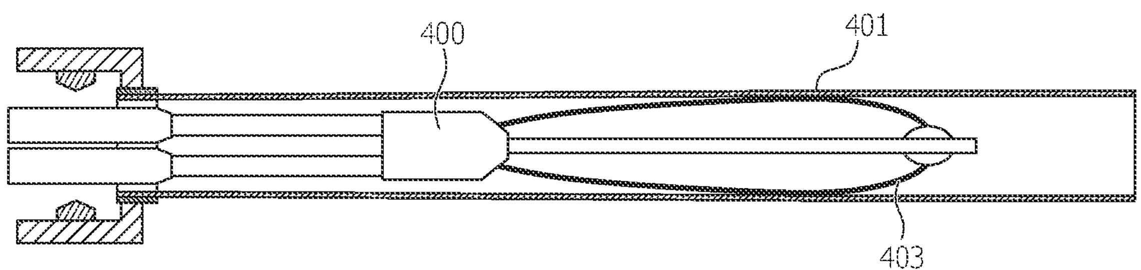
FIG. 4B illustrates placement of a balloon catheter system into an introducer sheath with a loop collapsed.

FIGS. 4A-B illustrate the insertion of balloon catheter (400) into introducer sheath (401). Insertion aid (402) comprised of a tube with a funnel shaped proximal segment can be used to collapse loop (403) to the inner diameter of introducer sheath (401). Insertion aid (402) is passed through hemostasis valve (404) of introducer sheath (401) as shown in FIG. 4A, and balloon catheter (400) is passed through insertion aid (402) into the lumen of introducer sheath (401). Insertion aid (402) is then withdrawn from introducer sheath (401). Insertion aid (402) can be retracted onto the proximal shaft of the balloon catheter (not shown). In other embodiments, insertion aid (402) can have a peel-away feature along its entire length to remove it completely from balloon catheter (400). FIG. 4B shows balloon catheter (400) placed into introducer sheath (401) with loop (403) collapsed.

Figure 5A:
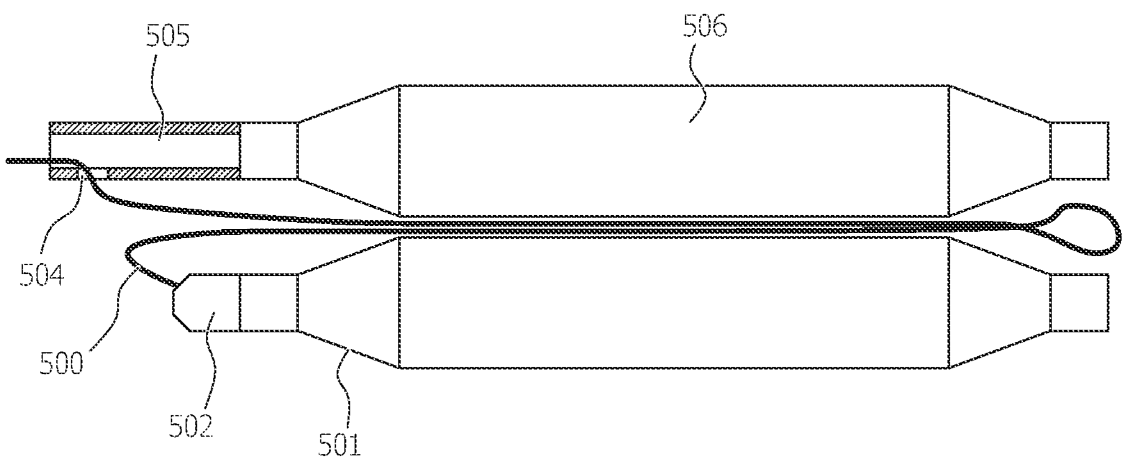
FIG. 5A illustrates a tether of a balloon catheter system.
Figure 5B:
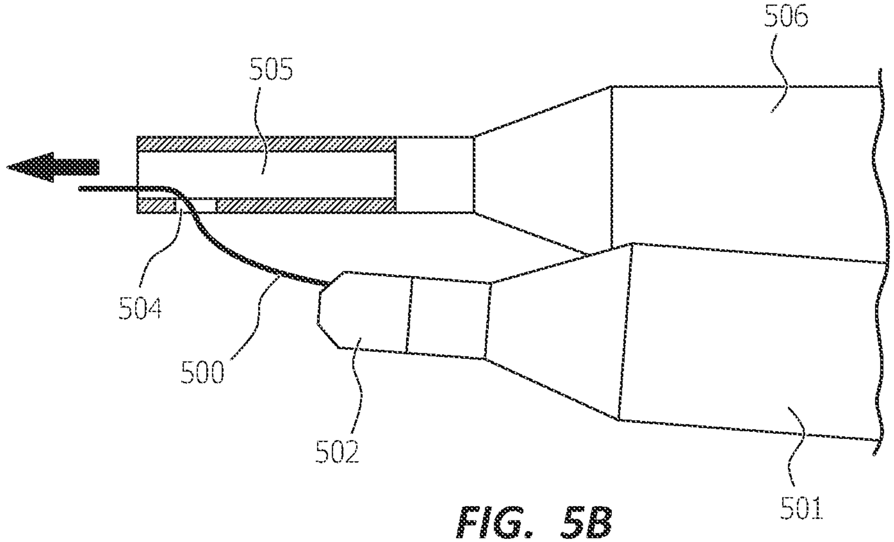
FIG. 5B illustrates a tether of a balloon catheter system with the tether pulled tight.

FIGS. 5A-B illustrate a tether feature of the balloon catheter system. In some embodiments, tether (500) can prevent second balloon (501) from catching the aortic bifurcation and/or from damaging the arterial walls during withdrawal of the balloon catheter system from the patient. Tether (500) can be made from a thin metal wire or flat metal band, such as, but not limited to, stainless steel or Nitinol. In other embodiments, tether (500) can be composed of polymer fibers or a polymeric monofilament, such as, but not limited to, Kevlar, polyester, PTFE, or a combination thereof. Tether (500) is connected to free end (502) of second balloon (501) and routed through opening (504) at the proximal end of catheter shaft (505) adjacent to first balloon (506) to the proximal hub of the catheter system (not shown). During insertion and advancement of the catheter system into the aorta and placement of second balloon (501) into the contralateral iliac artery, tether (500) is routed from free end (502) of second balloon (501) distally to the distal segments of second balloon (501) and then proximally to opening (504) as shown in FIG. 5A. Prior to retracting the catheter system, tether (500) is pulled tight to pull free end (502) of second balloon (501) against proximal end of catheter shaft (505) as shown in FIG. 5B. The steps of advancing and retracting the catheter system are further described in FIGS. 12A-H below. There are many possible routing pathways of the tether beyond the one described in FIGS. 5A-B to pull the second balloon toward the catheter shaft. For example, in some embodiments, the tether can be routed in a separate lumen parallel to the catheter shaft to the proximal end of the catheter. The tether can be routed to a separate port along the catheter shaft. It is understood that the invention is not limited to the specific pathway disclosed in FIGS. 5A-B.

Figure 6A:
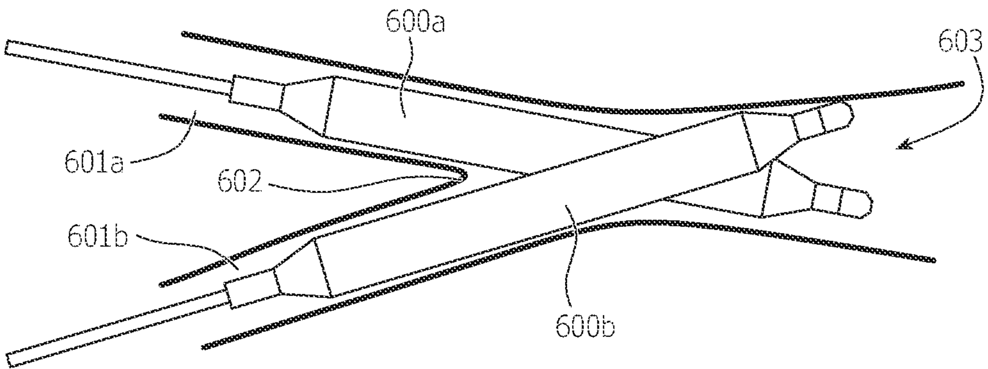
FIG. 6A illustrates a balloon catheter system with two balloons being partially joined along their line of contact.
Figure 6B:
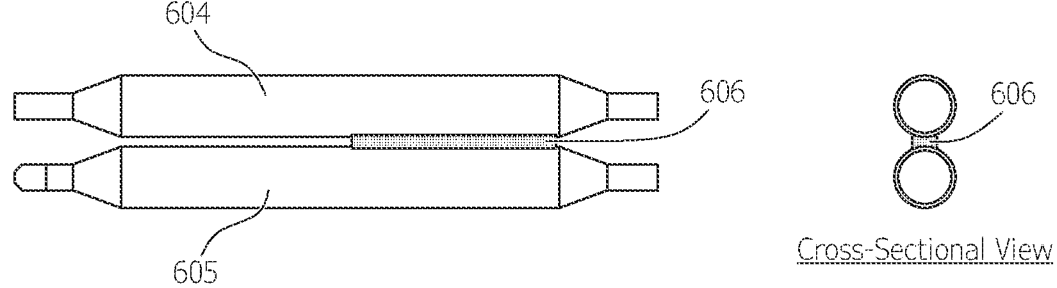
FIG. 6B illustrates a balloon catheter system with two balloons arranged in parallel and a cross-sectional view of the two balloons.

FIG. 6A illustrates the kissing balloon technique used for angioplasty procedures in AIOD. First balloon (600*a*) is placed from first iliac artery (601*a*) across aortic bifurcation (602) into aorta (603). Second balloon (600*b*) is placed from second iliac artery (601*b*) across aortic bifurcation (602) into aorta (603). One shortcoming of the technique is that balloons (600*a-b*) tend to cross over in aorta (603) deforming the aortic wall and creating unnecessary strain in the aortic tissue that can result in tissue damage and potential vessel rupture. FIG. 6B illustrates an example embodiment of a balloon assembly described herein that overcomes the above shortcoming. First balloon (604) and second balloon (605) are arranged in parallel. The proximal segments of first balloon (604) and second balloon (605) can be placed in the iliac arteries, the distal segments of first balloon (604) and second balloon (605) can be placed in the aorta. Balloons (604, 605) are joined along their distal segments to maintain a parallel configuration of balloons (604, 605) and prevent cross-over of the balloons in the aorta. Balloons (604, 605) can be joined by adhesive (606). In some embodiments, balloons (604,605) can be joined by thermo-fusion or other means.

Figure 7:
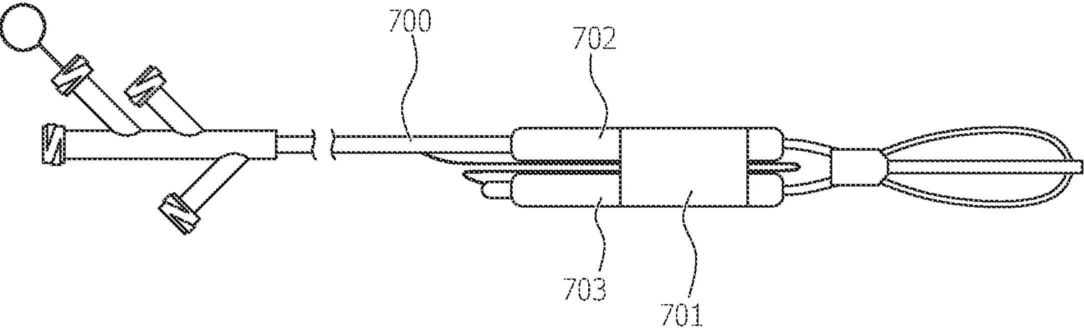
FIG. 7 illustrates a balloon catheter system with a constraining sleeve.
Figure 8:
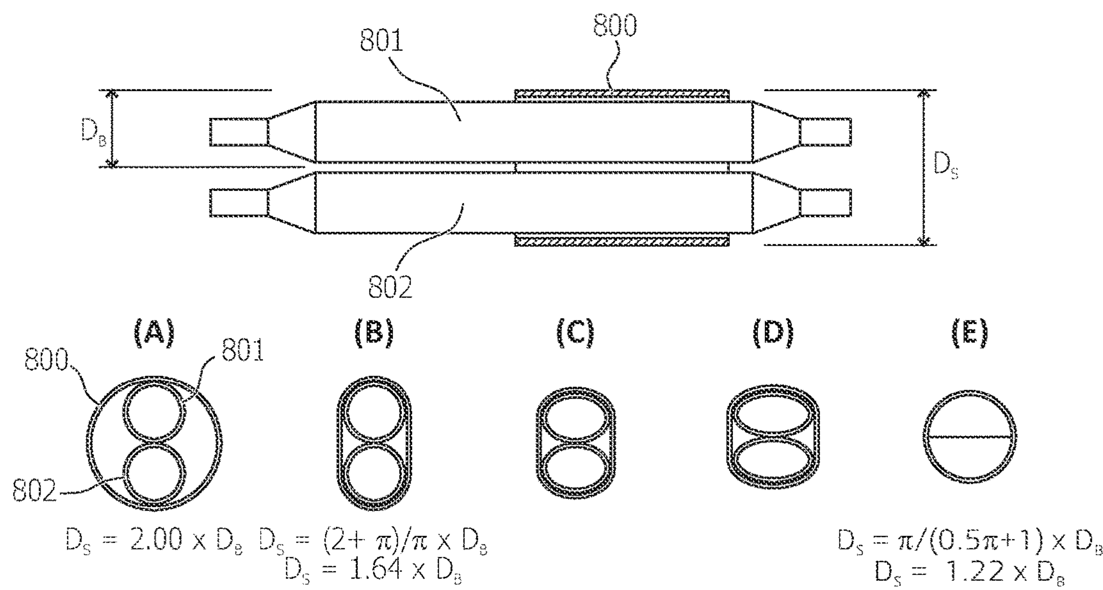
FIG. 8 illustrates a balloon catheter system with a constraining sleeve restricting the expansion of two balloons.

FIG. 7 illustrates another embodiment of balloon catheter system (700). In addition to the design elements/features of the embodiment described in FIG. 1, this other embodiment includes constraining sleeve (701) that is placed external to the distal segments of first balloon (702) and second balloon (703). Constraining sleeve (701) is further illustrated in FIG. 8. FIG. 8 shows first balloon (801) and second balloon (802) having a diameter Ds. Constraining sleeve (800) having diameter Ds is placed over the proximal segments of balloons (801, 802). The cross-sections (A) through (E) in FIG. 8 illustrate the effect of the diameter Ds of constraining sleeve (800) on the cross-sectional profile of balloons (801, 802). In cross-section (A), the sleeve diameter Ds is twice the diameter Ds of the balloons. The balloons are unconstrained. In cross-section (B), the sleeve diameter Ds is about 1.64 times the balloon diameter Ds. The balloons can still expand to a circular shape but are forced to make contact. In cross-sections (C) and (D) the diameter Ds of constraining sleeve (800) is further reduced. Fully inflated balloons (801, 802) are forced to take on non-circular shapes. Compared to cross-section (B), constraining sleeve (800) takes on a more circular shape in cross-section (C). When the diameter Ds of constraining sleeve is reduced to about 1.22 times the balloon diameter Ds, fully inflated balloons (801, 802) take on half-moon shapes and constraining sleeve (800) takes on a circular shape. Constraining sleeve (800) can be used to re-shape the cross-sectional profile of the proximal segments of balloons (801, 802) that are placed in the aorta to better conform to the cross-sectional shape of the aortic lumen. The diameter Ds of constraining sleeve (800) can be between about 1.6 times and about 1.2 times the diameter Ds of balloons (801, 802). In some embodiments, the diameter Ds of constraining sleeve (800) can be between about 1.3 times and about 1.2 times the diameter Ds of balloons (801, 802). The constraining sleeve can be made from similar material as the balloon such as, but not limited to, PET, Nylon, other suitable polymers or a combination thereof. The constraining sleeve can be a netting or woven structure made from monofilaments, fibers, and/or string. The constraining sleeve can be a series of axially arranged rings. It is understood that there are many means of externally constraining the expansion of the two parallel balloons in order to reshape their cross-sectional profile. The current systems are not limited to the embodiments described herein, but also include any means placed externally to the two balloons for the purpose of reshaping their cross-sectional profile.

Figure 9:
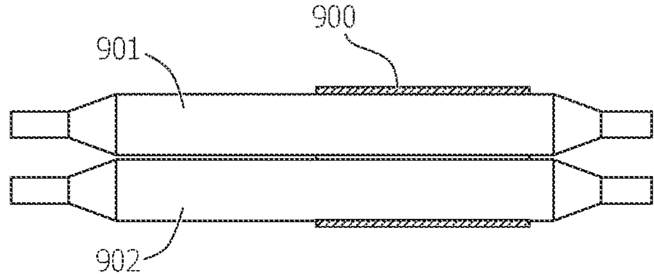
FIG. 9 is a table representing the diameters of the aorta, the iliac arteries, the balloons, and constraining sleeves of a balloon catheter system.

In a further consideration of the anatomy of the aortic bifurcation, the diameters of the balloons can vary from the proximal to the distal ends. Image analysis of the human aorta and iliac arteries indicate that the iliac arteries of healthy adults have a diameter of about 63% of that of the infrarenal aorta. Therefore, in some embodiments it can be advantageous if the distal segments of the balloons placed in the constraining sleeve form a first diameter corresponding to the targeted diameter of the aorta and the proximal segments of the balloons form a second diameter corresponding to the targeted diameter of the iliac arteries. FIG. 9 illustrates another balloon assembly comprising first balloon (901), second balloon (902) and constraining sleeve (900). The proximal segments of balloons (901, 902) have a first diameter and the distal segments of the balloons (901, 902) have a second diameter, with the first diameter being smaller than the second diameter. Using the formula provided for cross-section (E) in FIG. 8 and the relationship between the iliac artery diameter and aortic artery diameter stated above, one can calculate the desired diameter of the proximal and distal balloon segments to design a kissing balloon assembly that provides a circular cross-section in the aorta and, at the same time, preserves the diameter relationship between the aorta and the iliac arteries. The Table provided in FIG. 9 lists the expected diameters of iliac arteries, and the targeted diameters of the balloons and the constraining sleeve for diameters of the infrarenal aorta from 10 mm to 16 mm. It is understood that the diameter relationship between the iliac arteries and the aorta can vary depending on a patient's age, ethnicity, gender, and AIOC disease state. In some cases, the diameters of the two iliac arteries are not the same. The Table in FIG. 9 merely provides one example of selecting balloon and constraining sleeve diameters to create the desired geometry of the balloon assembly for balloon angioplasty of the aortic bifurcation.

Figure 10A:
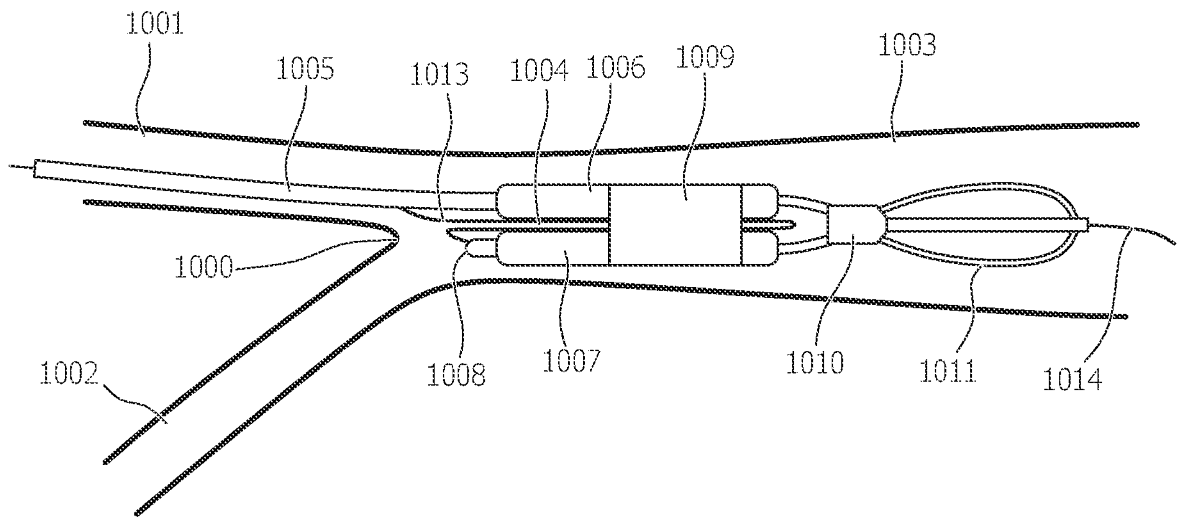
FIG. 10A illustrates a balloon catheter system advanced over a guidewire.

FIGS. 10A-10H illustrate steps for performing an angioplasty procedure at the aorto-iliac bifurcation. The illustrated steps can utilize an embodiment of the balloon catheter system described in FIG. 7. Methods of accessing the peripheral arteries and placement of a guidewire into the aorta are well described in the clinical literature and are not the subject of this invention. Percutaneous access is typically obtained from the femoral artery. A guidewire is then advanced from the femoral access point to the aorta. FIG. 10A shows aortic bifurcation (1000), ipsilateral iliac artery (1001), contralateral iliac artery (1002), and aorta (1003). Balloon catheter system (1004) comprises shaft (1005), first balloon (1006), second balloon (1007) with atraumatic free end (1008), constraining sleeve (1009), distal hub (1010), loop (1011) including a lumen fora second guidewire, and a tether (1013). Balloon catheter system (1004) is advanced over first guidewire (1014) into aorta (1003) until free end (1008) of second balloon (1007) clears aortic bifurcation (1000).

Figure 10B:
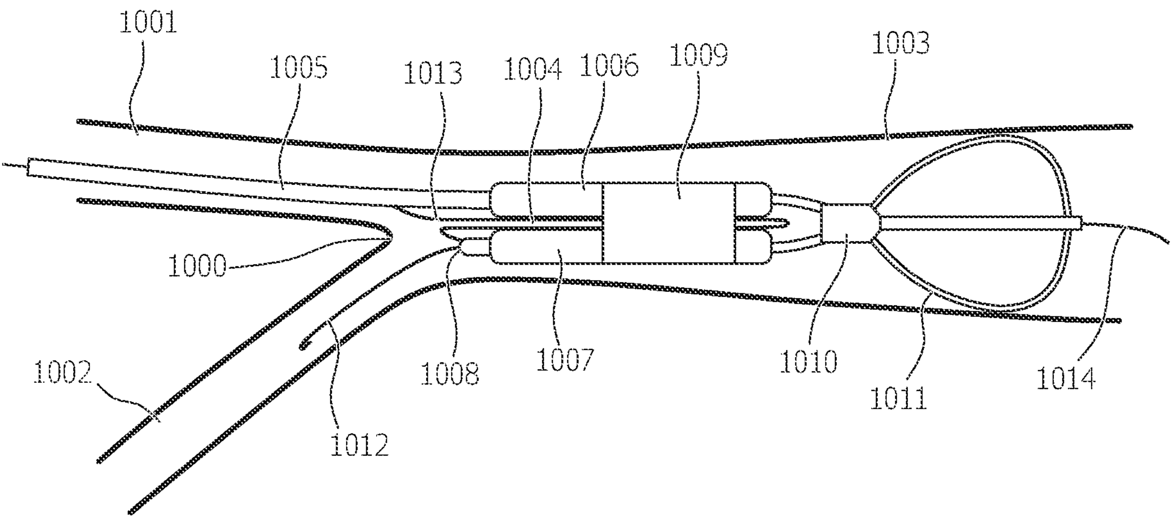
FIG. 10B illustrates a second guidewire advanced through the balloon catheter system of FIG. 10A.
Figure 10C:
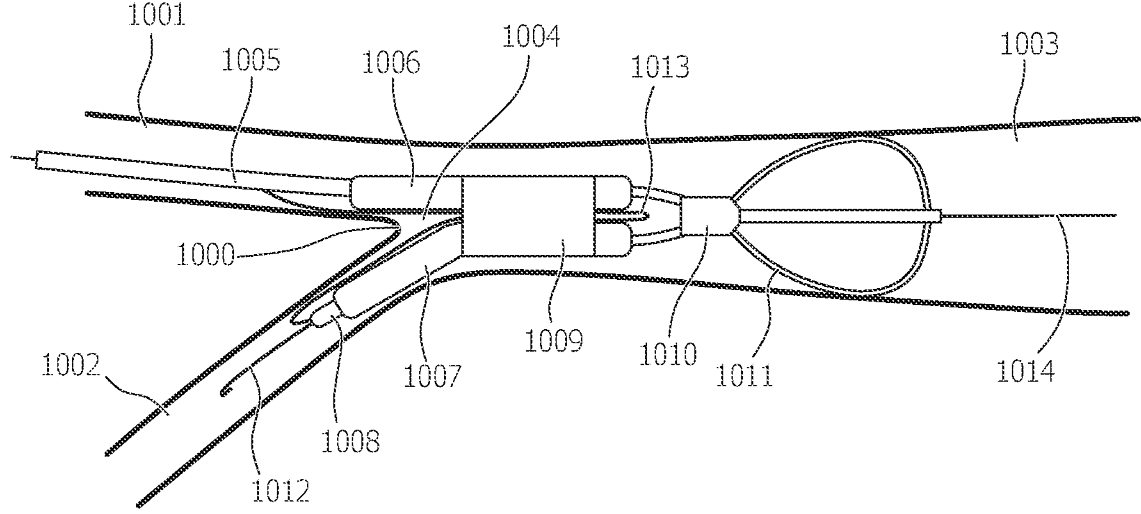
FIG. 10C illustrates partially retracing the balloon catheter system of FIG. 10A to advance a second balloon into a contralateral iliac artery.
Figure 10D:
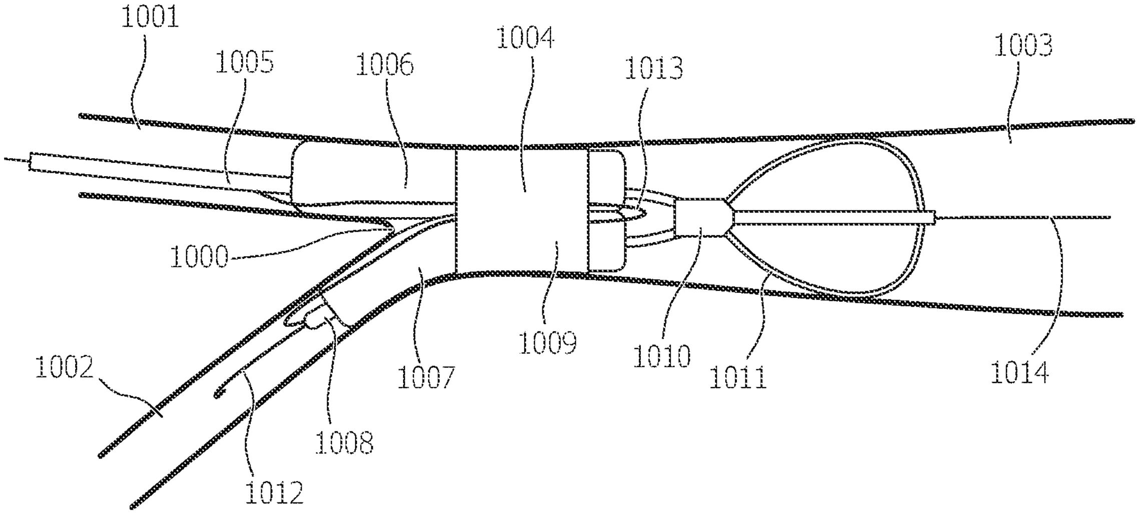
FIG. 10D illustrates simultaneously inflating balloons of the balloon catheter system of FIG. 10A.
Figure 10E:
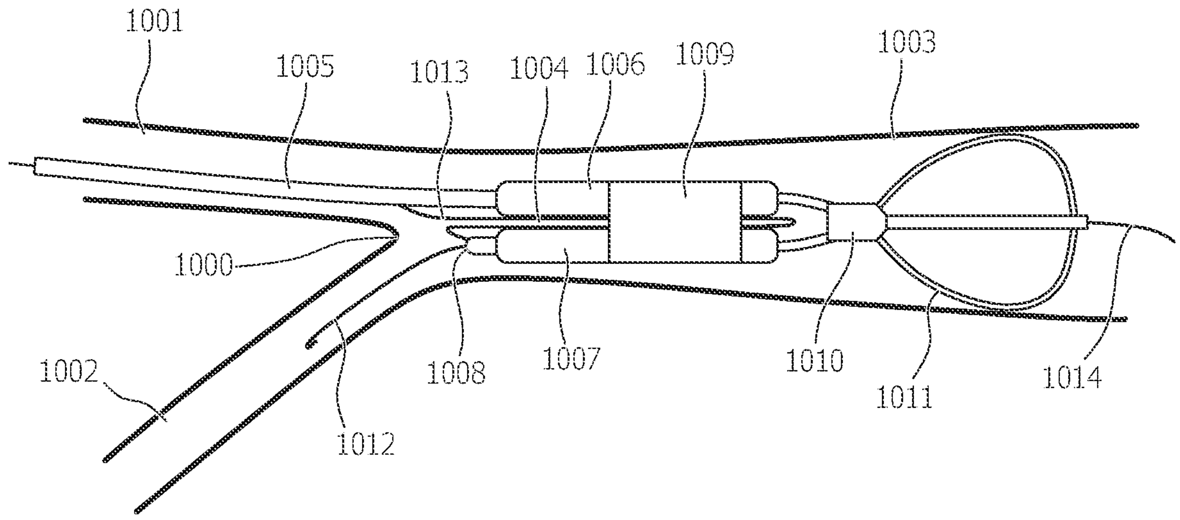
FIG. 10E illustrates advancing the balloon catheter system of FIG. 10A to retract the second balloon from the contralateral iliac artery.
Figure 10F:
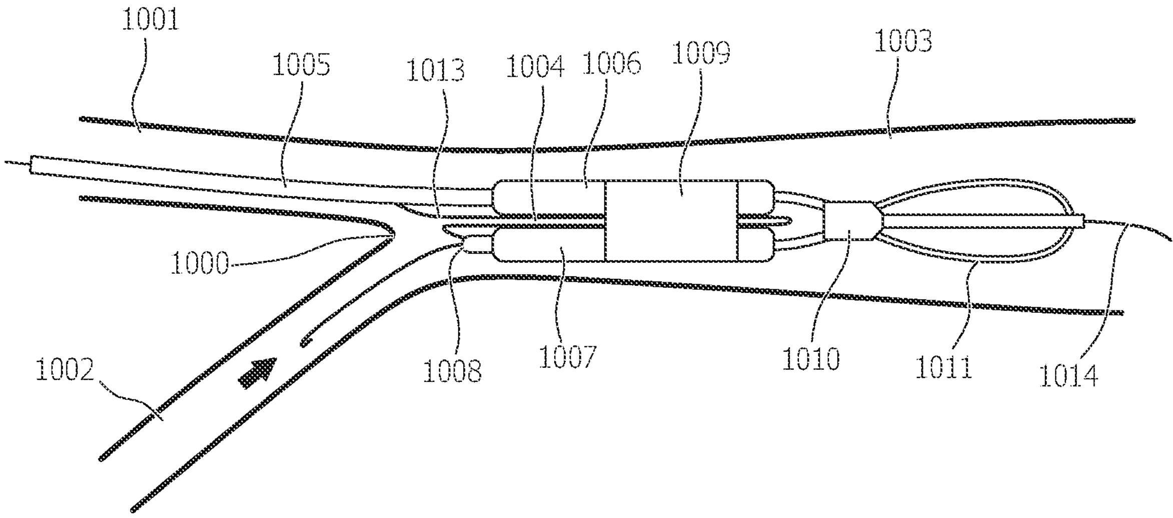
FIG. 10F illustrates retracting the second guidewire of the balloon catheter system of FIG. 10A.
Figure 10G:
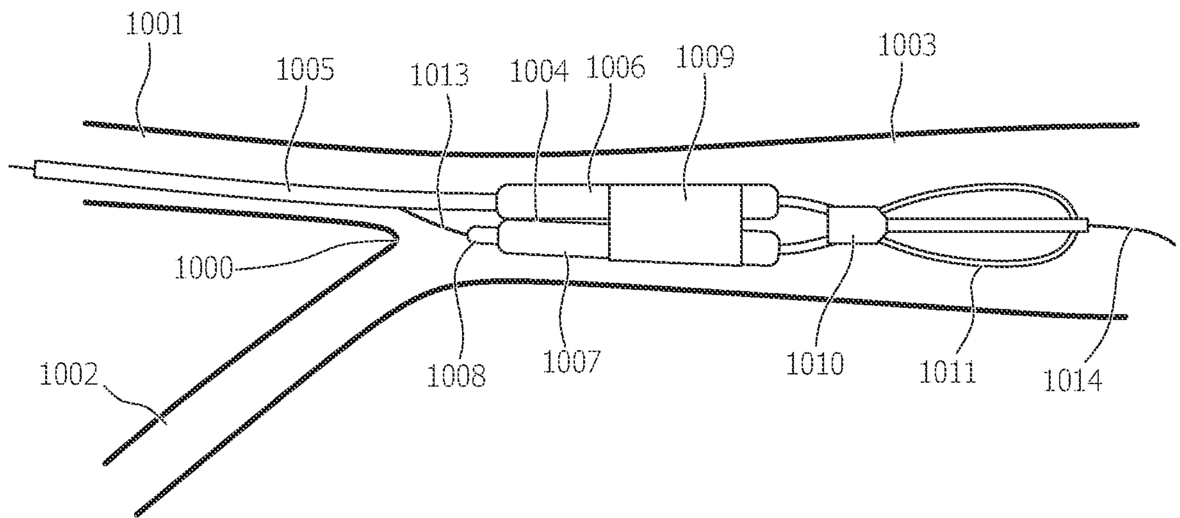
FIG. 10G illustrates pulling on a tether of the balloon catheter system of FIG. 10A to pull a free end of the second balloon.
Figure 10H:
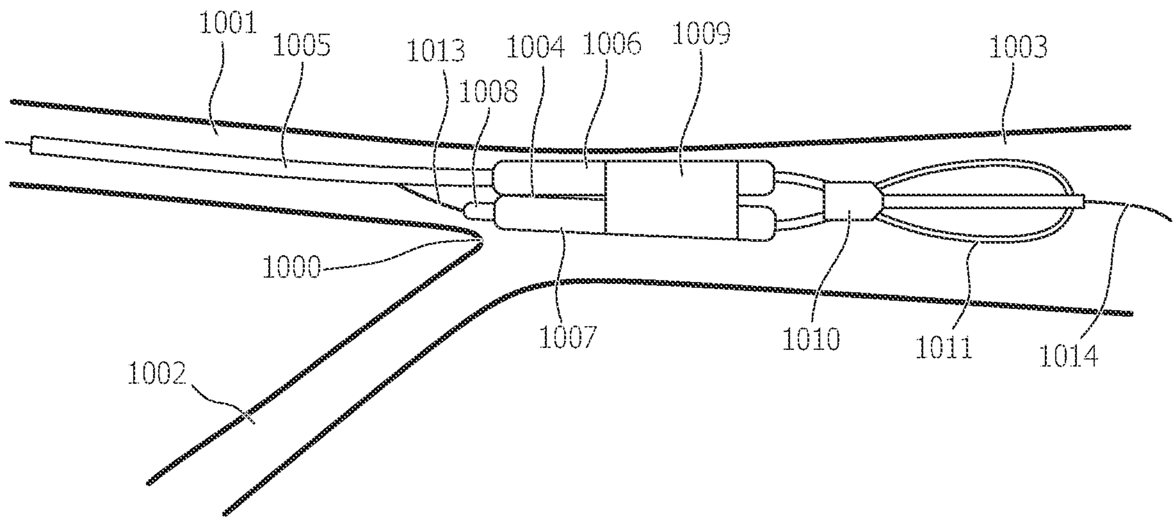
FIG. 10H illustrates retracting the balloon catheter system of FIG. 10A.

In FIG. 10B second guidewire (1012) is advanced through shaft (1005), first balloon (1006), loop (1011), and second balloon (1007) and exits balloon catheter system (1004) at free end (1008). An operator can then steer second guidewire (1012) into contralateral iliac artery (1002). FIG. 10C illustrates the step of partially retracting balloon catheter system (1004) to advance second balloon (1007) into contralateral iliac artery (1002). In some embodiments, second guidewire (1012) can be captured from the contralateral side with a snare and/or externalized through a contralateral access point to provide additional support for advancing second balloon (1007) into contralateral iliac artery (1002). Constraining sleeve (1009) is positioned in aorta (1003). FIG. 10D illustrates the step of simultaneously inflating balloons (1006, 1007) to perform an angioplasty. In some embodiments, constraining sleeve (1009), can have a diameter of about 1.2 to about 1.6 times that of balloons (1006, 1007), which forces balloons (1006, 1007) to take on a more circular shape in aorta (1003) as illustrated in FIG. 8 sections (C), (D), and (E). After completion of the angioplasty, balloons (1006, 1007) are deflated. FIG. 10E illustrates the step of advancing balloon catheter system (1004) to retract second balloon (1007) from contralateral iliac artery (1002). The arrow in FIG. 10F illustrates the step of retracting second guidewire (1012) into balloon catheter system (1004). FIG. 10G illustrates the step of pulling on tether (1013) to pull free end (1008) of second balloon (1007) against shaft (1005). FIG. 10H illustrates the step of retracting balloon catheter system (1004) from the body. Tether (1013) ensures that second balloon (1007) does not catch aortic bifurcation (1000) during retraction of balloon catheter system (1004). It is understood that the steps illustrated in FIGS. 10A-H provide one exemplary sequence of procedural steps for performing an angioplasty of the aortic bifurcation with the balloon catheter system described herein. Further steps can be added and/or removed, or the sequence of steps can be altered.

Figure 11:
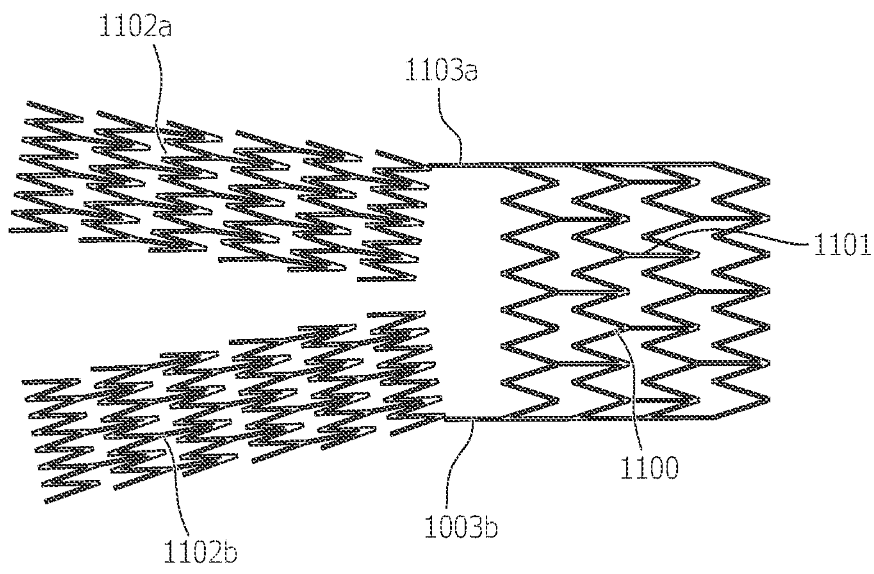
FIG. 11 illustrates an embodiment of a bifurcated stent described herein.

In some embodiments, the balloon catheter system can be utilized to place a bifurcated stent into the aortic bifurcation. FIG. 11 illustrates balloon-expandable bifurcated stent (1100). Balloon-expandable bifurcated stent (1100) comprises main body stent (1101) and branch stents (1102*a-b*). Main body stent (1101) can be connected/attached to branch stents (1102*a-b*) by axial connectors (1103*a-b*). Bifurcated stent (1100) can be covered or encapsulated with biocompatible material, such as, but not limited to, ePTFE polyurethane, woven polyester, or a combination thereof.

Figure 12:
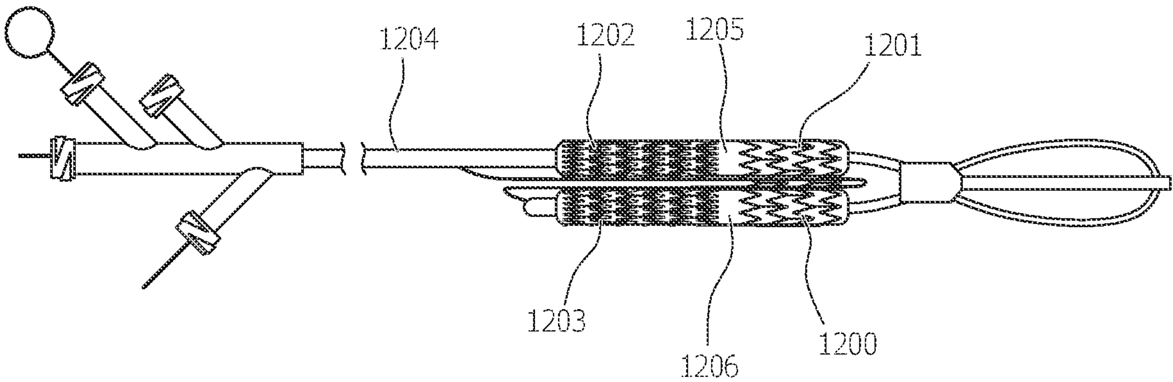
FIG. 12 illustrates an embodiment of a bifurcated stent mounted onto a balloon catheter system described herein.

FIG. 12 illustrates balloon-expandable bifurcating stent (1200) crimped onto balloon catheter system (1204). Main body stent (1201) is crimped onto the distal segments of first balloon (1205) and second balloon (1206). First branch stent (1202) is crimped onto the proximal segment of first balloon (1205) and second branch stent (1203) is crimped onto second balloon (1206). In other embodiments, the balloon catheter system can include a constraining sleeve. FIG. 7 illustrates a constraining sleeve that can be included. In some embodiments, the main body of the bifurcated stent can be crimped onto the constraining sleeve.

In some embodiments, the procedure for placing a bifurcating stent into the aortic bifurcation can follow similar steps to those used for the angioplasty procedure illustrated in FIGS. 10A-H. In other embodiments, the main body stent and the branch stents can be post ballooned to conform to the vessel wall of the ipsilateral and contralateral iliac artery and the infrarenal aorta.

Figure 13A:
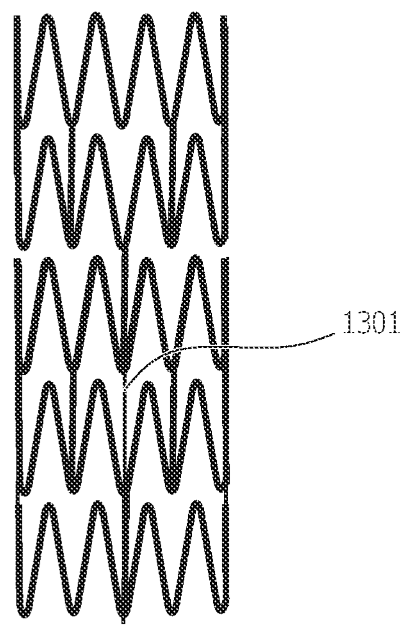
FIG. 13A illustrates a tubular balloon-expandable stent of a bifurcated stent graft.
Figure 13B:
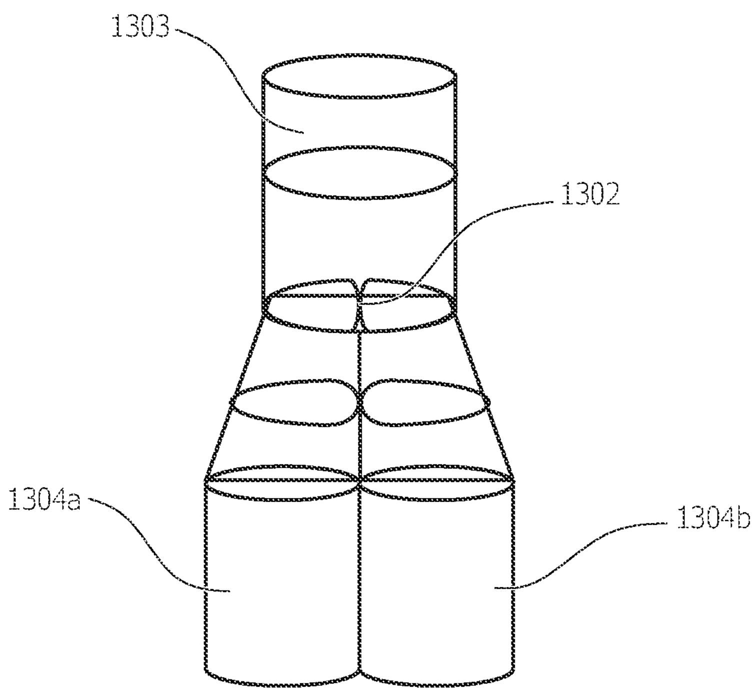
FIG. 13B illustrates an embodiment of a bifurcated stent graft.
Figure 13C:
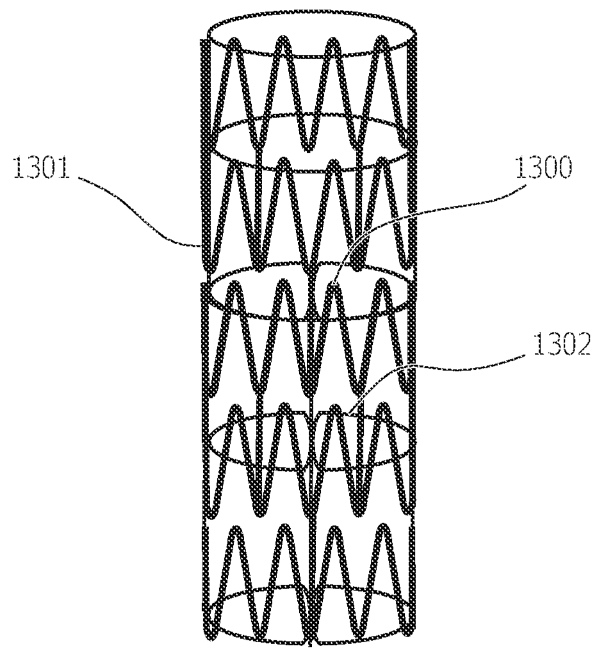
FIG. 13C illustrates a bifurcating graft mounted inside a tubular stent.

FIGS. 13A-C illustrate another embodiment of a bifurcated stent graft. Bifurcated stent graft (1300) comprises tubular balloon-expandable stent (1301) as shown in FIG. 13A with a diameter that conforms to the infrarenal aorta. In some embodiments, bifurcated stent graft (1300) can further comprise bifurcating graft (1302) as shown in FIG. 13B. Bifurcated graft (1302) comprises tubular main body graft (1303) and connecting tubular branch grafts (1304*a-b*). FIG. 13C illustrates bifurcating graft (1302) mounted inside tubular stent (1301). Bifurcating graft (1302) can be made from ePTFE, PTFE, polyester, polyurethane, Nitinol film, or a combination thereof. In some embodiments, the bifurcating graft can be made of any other thin-wall biocompatible material. The material can be porous or non-porous.

Figure 14:
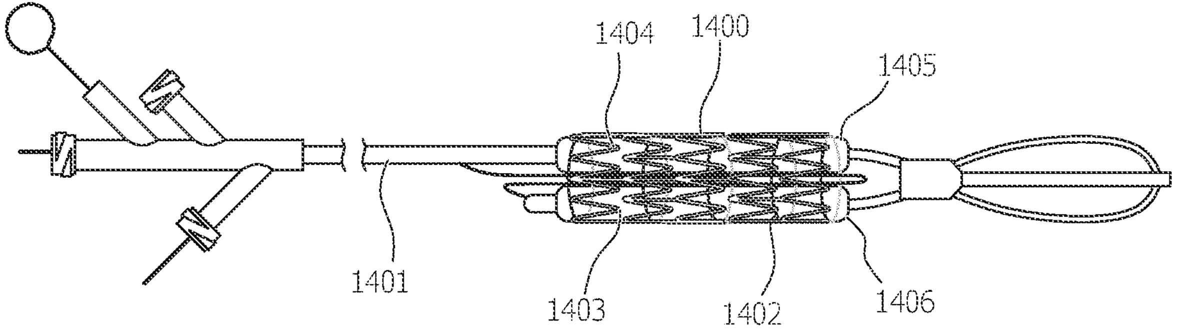
FIG. 14 illustrates another embodiment of a bifurcated stent mounted onto a balloon catheter system described herein.

FIG. 14 illustrates another embodiment of a bifurcated stent graft crimped onto a balloon catheter system as described herein. The section of bifurcated stent graft (1400) including main body graft (1402) is crimped onto the distal segments of first balloon (1405) and second balloon (1406). First branch graft (1404) is crimped onto the proximal segment of first balloon (1405) and second branch graft (1403) is crimped onto second balloon (1406). In other embodiments, the balloon catheter system can further comprise a constraining sleeve. FIG. 7 illustrates a constraining sleeve that can be utilized. In some embodiments, the main body graft can be crimped onto the constraining sleeve.

Figure 15A:
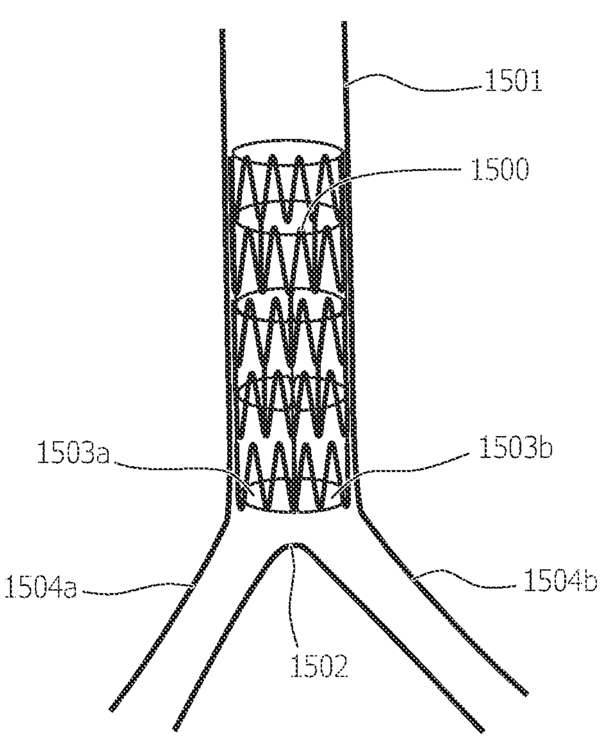
FIG. 15A illustrates another embodiment of a bifurcated stent placed in an infrarenal aorta to treat AIOD.
Figure 15B:
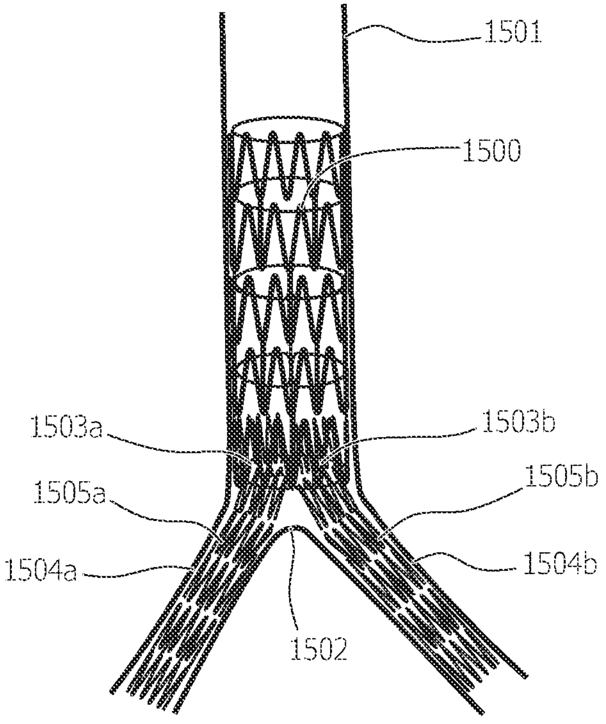
FIG. 15B illustrates the bifurcated stent placed in the infrarenal aorta.

The procedural steps for placing the bifurcated stent graft illustrated in FIG. 14 are similar to those described in FIGS. 10A-10H with the exception of omitting the procedural step illustrated in FIG. 10C and deploying the entire bifurcated stent graft distal to the aortic bifurcation. FIGS. 15A-B further illustrate the placement of the bifurcated stent graft illustrated in FIG. 14 to treat the aortic bifurcation. FIG. 15A illustrates bifurcated stent graft (1500) deployed in the infrarenal aorta (1501) above aortic bifurcation (1502). First branch graft (1503*a*) is aligned with first iliac artery (1504*a*) and second branch graft (1503*b*) is aligned with second iliac artery (1504*b*). Once stent graft (1500) is deployed, the procedure is completed by placing tubular stents (1505*a-b*) into iliac arteries (1504*a-b*), respectively. The distal end of first tubular stent (1505*a*) is placed in an overlapping fashion into first branch graft (1503*a*). The distal end of second tubular stent (1505*b*) is placed in an overlapping fashion into second branch graft (1503*b*). The tubular stents can be bare metal stents or covered stents.

Figure 16A:
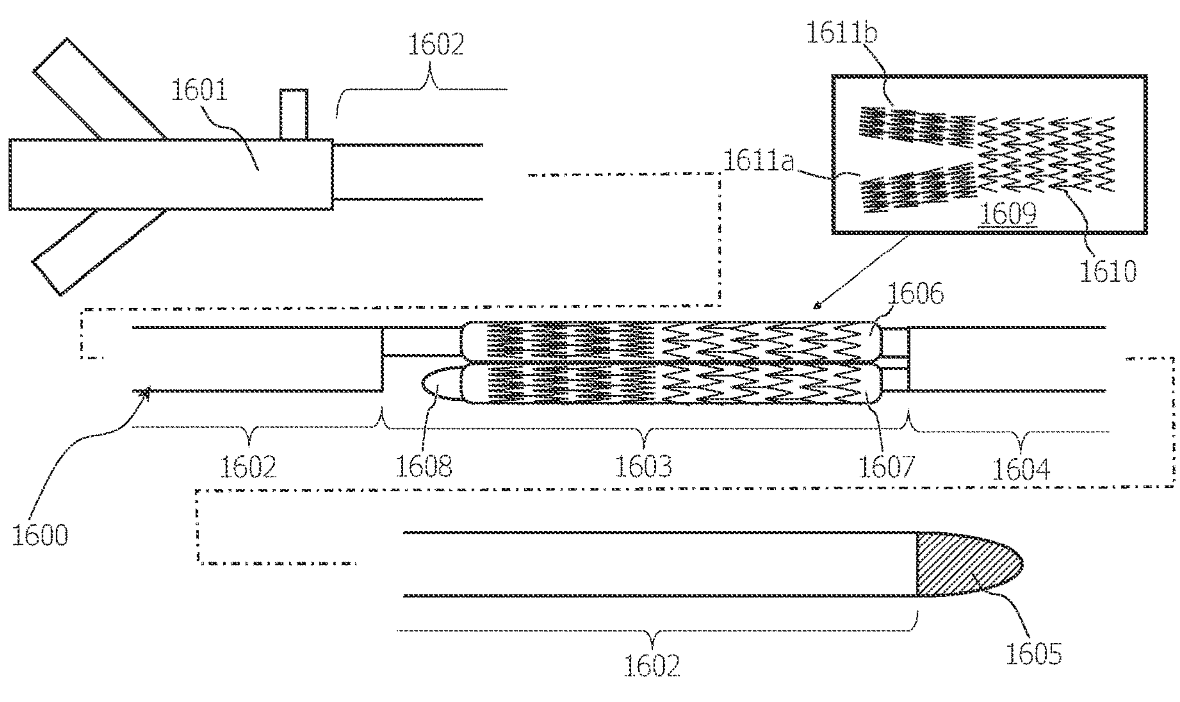
FIG. 16A illustrates an example embodiment of a balloon catheter.
Figure 16B:
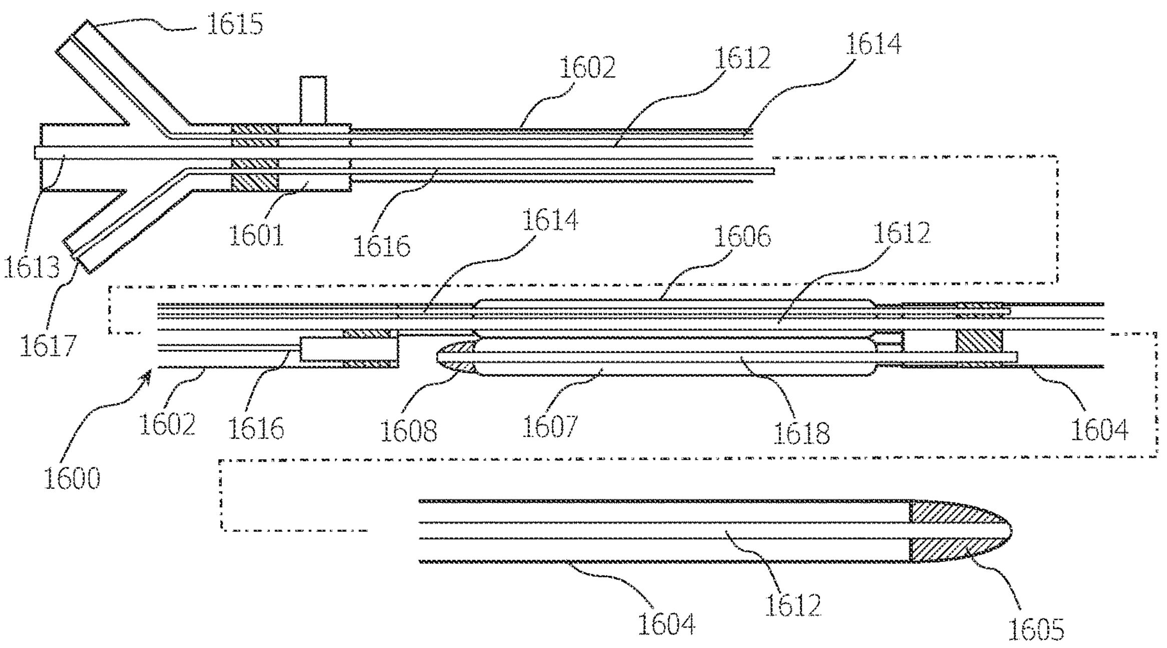
FIG. 16B illustrates schematic placement of lumens within the balloon catheter of FIG. 16A.

FIGS. 16A-B illustrate another embodiment of the balloon catheter described herein. FIG. 16A illustrates the external components of the balloon catheter. Balloon catheter (1600) comprises proximal hub (1601), proximal shaft (1602), balloon assembly (1603), distal shaft (1604), and distal tip (1605). In some embodiments, the balloon assembly comprises first (ipsilateral) balloon (1606) and second (contralateral) balloon (1607) that are arranged substantially in parallel. The proximal end of first balloon (1606) is connected to the distal end of proximal shaft (1602). The distal end of first balloon (1606) is connected to the proximal end of distal shaft (1604). Atraumatic tip (1608) is connected to the proximal free end of the second balloon (1607). The distal end of second balloon (1607) is connected to the proximal end of distal shaft (1604). For illustration purposes, bifurcated stent (1609) comprising main body stent (1610) and branch stents (1611*a-b*) is shown crimped onto balloon assembly (1603).

FIG. 16B illustrates the lumens within balloon catheter (1600). First lumen (1612) extends from first port (1613) in proximal hub (1601) through proximal shaft (1602), first balloon (1606), distal shaft (1604), and distal tip (1605). Second lumen (1614) extends from second port (1615) in proximal hub (1601) through proximal shaft (1602), and first balloon (1606) into distal shaft (1604). Third lumen (1616) extends from third port (1617) in proximal hub (1601) through proximal shaft (1602) and terminates at the end of proximal shaft (1602) opposite to atraumatic tip (1608) of second balloon (1607). Fourth lumen (1618) extends from distal shaft (1604) through second balloon (1607) to contralateral tip (1608).

Figure 17:
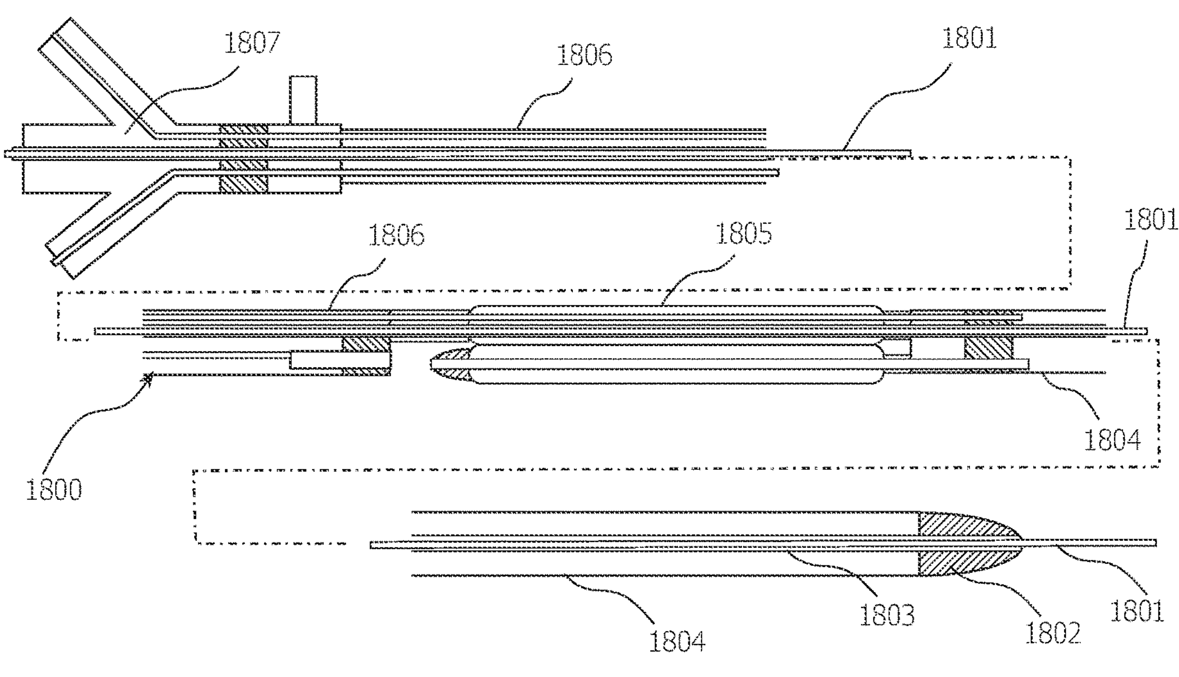
FIG. 17 illustrates an inflation lumen of a balloon catheter.

FIG. 17 illustrates the fluid pathway of the inflation medium within balloon catheter (1700). The inflation medium is injected into inflation port (1701). Inflation port (1701) is in direct fluid communication with the distal end of proximal hub (1702). The distal end of proximal hub (1702) is in direct fluid communication with proximal shaft (1703). The distal end of proximal hub (1702) is sealed off proximally to inflation port (1701) to prevent backflow of inflation medium into the proximal section of proximal hub (1702). The proximal end of proximal shaft (1703) is sealed off on the contralateral side and only allows medium to enter first balloon (1704). The proximal section of distal shaft (1705) is in fluid communication with first balloon (1704) and second balloon (1706). The proximal section of distal shaft (1705) is sealed off distally to prevent medium from entering the main section of distal shaft (1705). The flow pathway through balloon catheter (1700) forms a bifurcated lumen with the first proximal lumen extending from the proximal end of distal shaft (1705) to inflation port (1701), the second proximal lumen extending from the proximal end of distal shaft (1705) to second balloon (1706), and the distal lumen extending within the proximal segment of distal shaft (1705).

Figure 18:
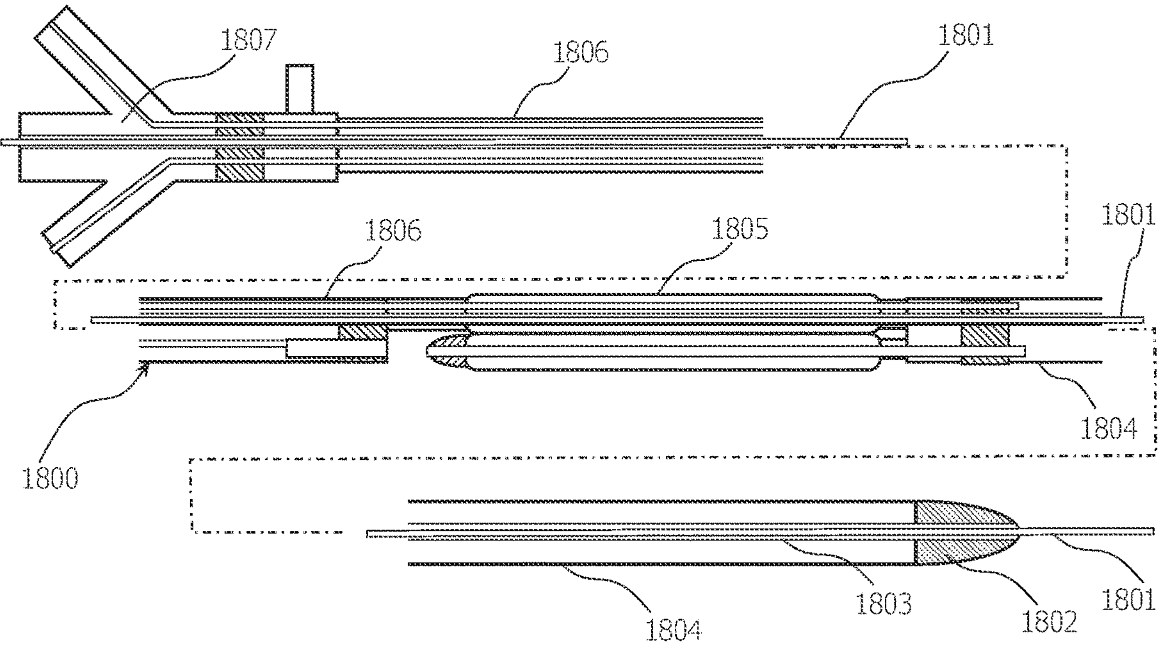
FIG. 18 illustrates a pathway of an ipsilateral guidewire through a balloon catheter.

FIG. 18 illustrates the pathway of a guidewire over which the balloon catheter tracks through the femoral access vessel into the aorta. Guidewire (1801) is inserted at distal tip (1802) of balloon catheter (1800) into first lumen (1803), which extends from distal tip (1802) through distal shaft (1804), first balloon (1805), and proximal shaft (1806) to proximal hub (1807). First lumen (1803) is also referred to as the ipsilateral guidewire lumen and the first guidewire (1801) as the ipsilateral guidewire.

Figure 19A:
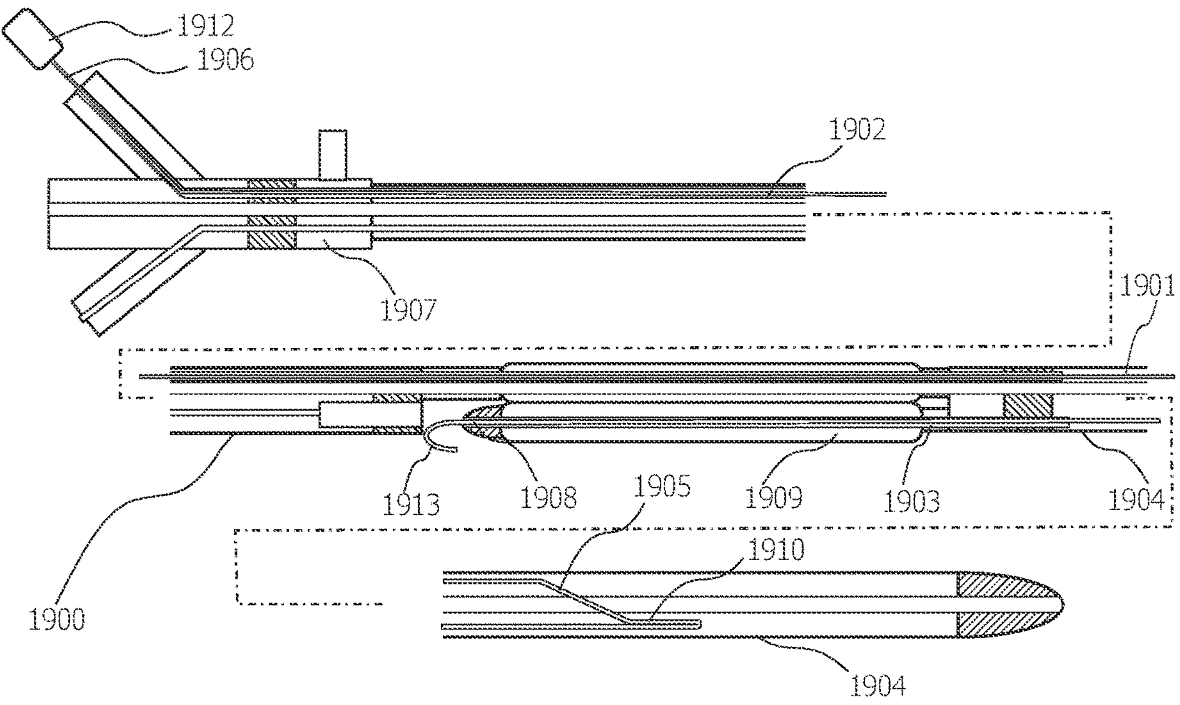
FIG. 19A illustrates a position of a contralateral guidewire in a corresponding pathway in a balloon catheter.
Figure 19B:
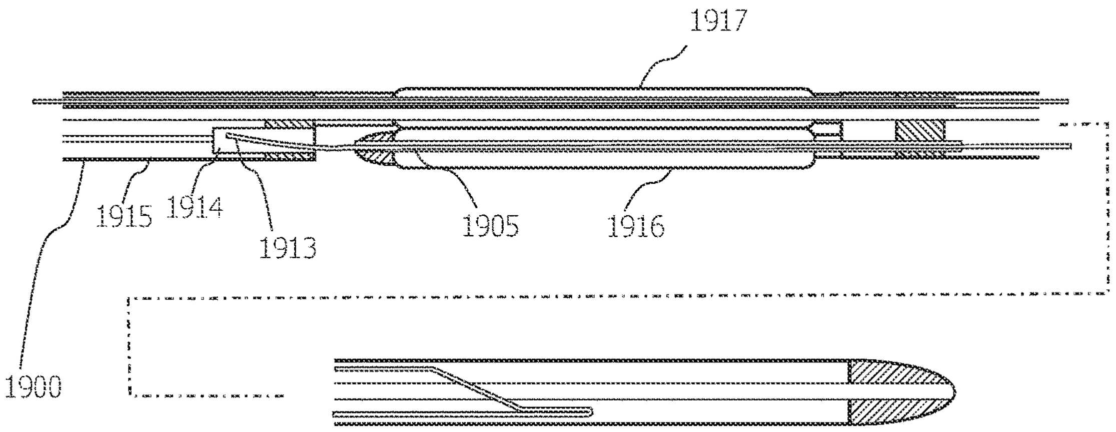
FIG. 19B illustrates another position of the contralateral guidewire of FIG. 19A in the corresponding pathway in the balloon catheter.
Figure 19C:
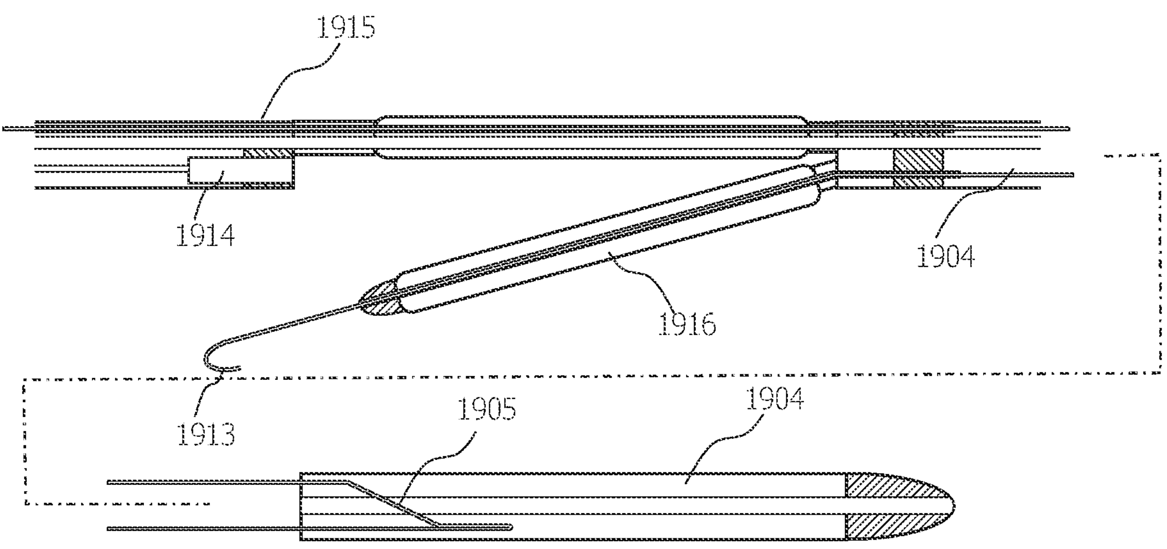
FIG. 19C illustrates another position of the contralateral guidewire of FIG. 19A in the corresponding pathway in the balloon catheter.

FIGS. 19A-C illustrate the contralateral guidewire of balloon catheter (1900). FIG. 19A illustrates bifurcated contralateral guidewire lumen (1901) formed by second lumen (1902) and third lumen (1903), and the distal section of distal shaft (1904). The bifurcated guidewire lumen is substantially coaxially arranged with the bifurcated inflation lumen. Contralateral guidewire (1905) passes through the bifurcated contralateral guidewire lumen (1901). Contralateral guidewire (1905) comprises first proximal end (1906) that exits balloon catheter (1900) at proximal hub (1907) and second proximal end (1908) that exits balloon catheter (1900) at the free end of second balloon (1909), and distal end (1910) which is retained within distal shaft (1904). First proximal end (1906) of contralateral guidewire (1901) is connected to guidewire handle (1912). Second proximal end (1908) of contralateral guidewire (1901) comprises shaped flexible guidewire tip (1913) for advancing contralateral guidewire (1901) atraumatically through the vasculature. Moving guidewire handle (1912) proximally moves contralateral guidewire tip (1913) proximally. Moving guidewire handle (1912) distally moves contralateral guidewire tip (1913) distally. Rotating guidewire handle (1912) clockwise rotates contralateral guidewire tip (1913) clockwise. Rotating guidewire handle (1912) counter-clockwise rotates contralateral guidewire tip (1913) counter-clockwise.

FIG. 19B illustrates the position of contralateral guidewire (1905) during device insertion. Guidewire tip (1913) is housed in guidewire recess (1914) within proximal shaft (1915). In this configuration, second balloon (1916) is locked in a position substantially parallel to first balloon (1917). FIG. 19C illustrates the position of contralateral guidewire (1905) during cannulation of the contralateral iliac artery. Contralateral guidewire (1905) is advanced proximally, and second balloon (1916) can swivel away from the proximal shaft (1915). The length of axial travel of contralateral guidewire (1905) is limited by the length of distal guidewire lumen (1904). In some embodiments, the length of the distal guidewire lumen and with it the length of travel of the contralateral guidewire is at least equal to the distance from the aortic bifurcation to the proximal target location of the contralateral branch stent. The length of the distal guidewire lumen and the guidewire travel can be 3 cm, 5 cm, 10 cm, 15 cm, 20 cm, about 3 cm, about 4 cm, about 5 cm, about 6 cm, about 7 cm, about 8 cm, about 9 cm, about 10 cm, about 11 cm, about 12 cm, about 13 cm, about 14 cm, about 15 cm, about 16 cm, about 17 cm, about 18 cm, about 19 cm, about 20 cm, about 21 cm, about 22 cm, between about 1 cm and about 10 cm, between about 9 cm and about 18 cm, between about 13 cm and about 22 cm, or any value in between these values.

Figure 20A:
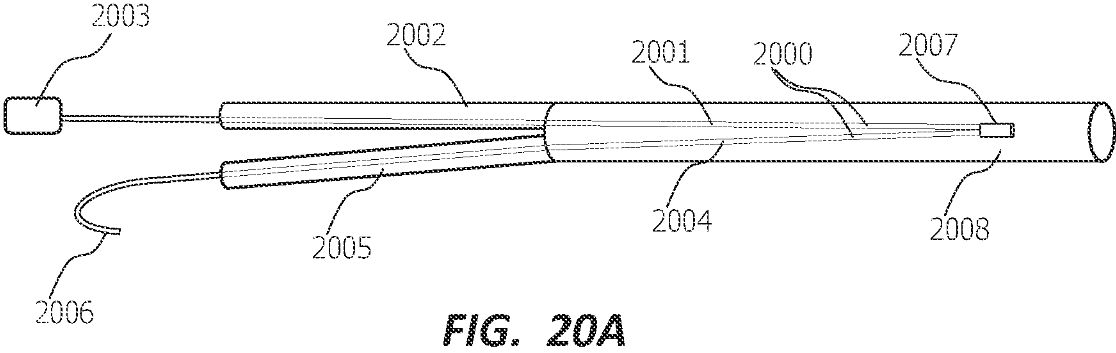
FIG. 20A illustrates a position of a contralateral guidewire assembly in a balloon catheter.
Figure 20B:
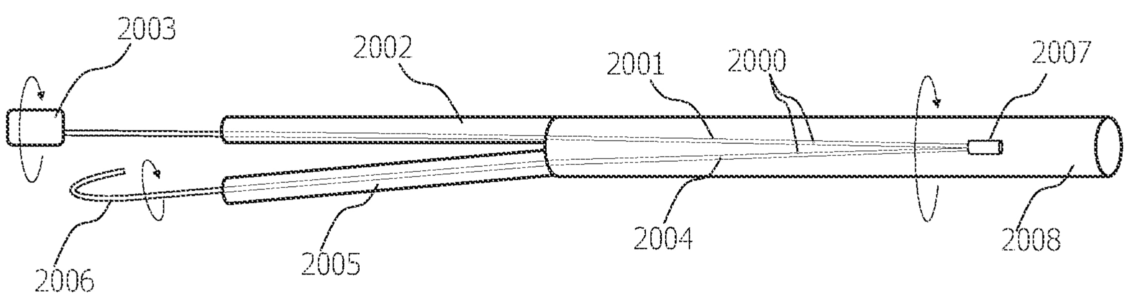
FIG. 20B illustrates rotation of the contralateral guidewire assembly of FIG. 20A.

FIGS. 20A-B further illustrate the rotation of contralateral guidewire (2000). Ipsilateral arm (2001) of the guidewire is passed through ipsilateral lumen (2002) and connected at its proximal end to guidewire handle (2003). Contralateral arm (2004) of the guidewire is passed through contralateral lumen (2005) and terminates at its proximal end in flexible guidewire tip (2006). The two distal ends of guidewire arms (2001, 2004) are joined together by guidewire connector (2007) in distal lumen (2008). Ipsilateral arm (2001) can be made from a metal wire, such as, but not limited to, stainless steel, Cobalt Chromium, Nitinol, or a combination thereof. The diameter of the wire can be at least 0.015" to provide a good torsion response. In other embodiments, ipsilateral arm (2001) can be made from a braided wire or a braid-reinforced polymeric tube or rod. The proximal section of contralateral arm (2004) can adopt the properties of guidewires used for aortoiliac interventions. In some embodiments, the proximal section of contralateral arm can comprise a solid or braided inner core, an outer coil, a radiopaque tip, and PTFE coating. The proximal end of contralateral arm (2004) can be straight, curved, or form a "J". The diameter of the proximal section of contralateral arm (2004) can be 0.015", 0.018", 0.035", 0.038", about 0.010", about 0.020", about 0.030", about 0.040", between about 0.010" and about 0.021", between about 0.015" to about 0.040", or any value in between these values.

Guidewire connector (2007) can further comprise a sleeve placed over and bonded to guidewire arms (2001, 2004). Guidewire connector (2007) can be a weld or crimp terminal. Rotating guidewire handle (2003) causes ipsilateral arm (2001) to twist around contralateral arm (2004) as shown in FIG. 20B. The twisting motion translates into a rotation of contralateral arm (2004) and guidewire tip (2006). In some embodiments, the number of rotations that can be achieved is limited. When guidewire connector (2007) is in close proximity to ipsilateral lumen (2002) and contralateral lumen (2005), rotation of contralateral guidewire (2000) may not be possible. In other embodiments, the number of rotations that can be achieved is not limited.

Figure 21:
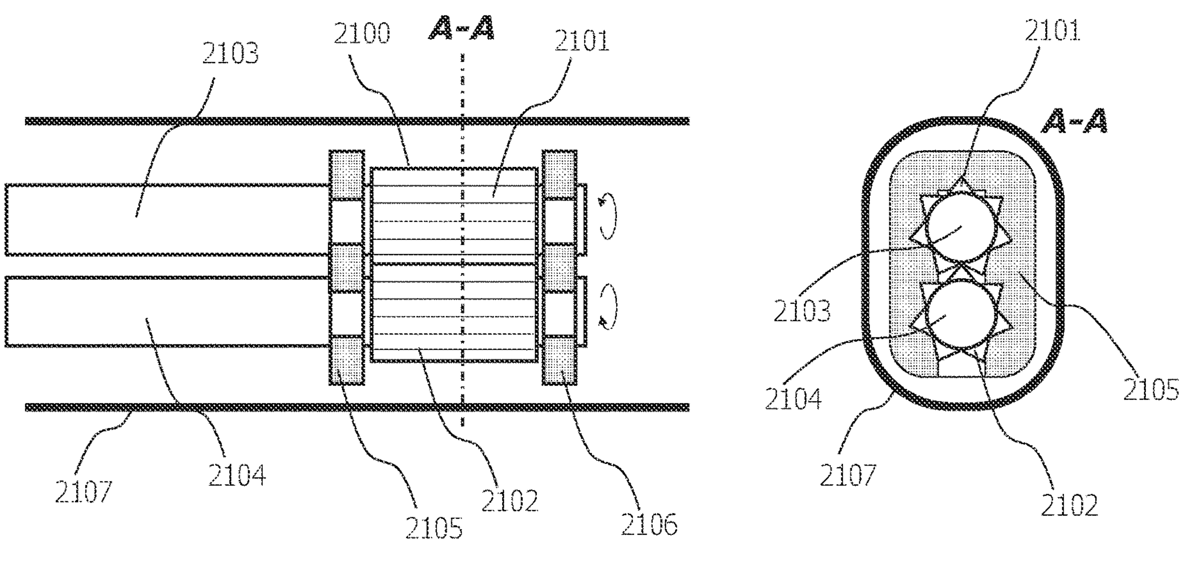
FIG. 21 illustrates an embodiment of a contralateral guidewire transmission.

FIG. 21 illustrates an embodiment of distal guidewire transmission (2100) to support transmission of rotational motion from the first guidewire arm to second guidewire arm without twisting of the guidewire arms. Gear wheels (2101, 2102) are mounted onto the distal ends of guidewire arms (2103, 2104) and are engaged with each other. The distal ends of guidewire arms (2103, 2104) are held in a parallel configuration by retaining clips (2105, 2106). Retaining clips (2105, 2106) allow guidewire arms (2103, 2104) to rotate, and at the same time, prevent axial movement of guidewire arms (2103, 2104) with respect to each other. Rotating first guidewire arm (2103) clockwise causes second guidewire arm (2104) to rotate counterclockwise. To avoid twisting of guidewire arms (2103, 2104), distal guidewire lumen (2107) is non-circular in shape preventing guidewire transmission (2100) from rotating within distal guidewire lumen (2107).

Figure 22:
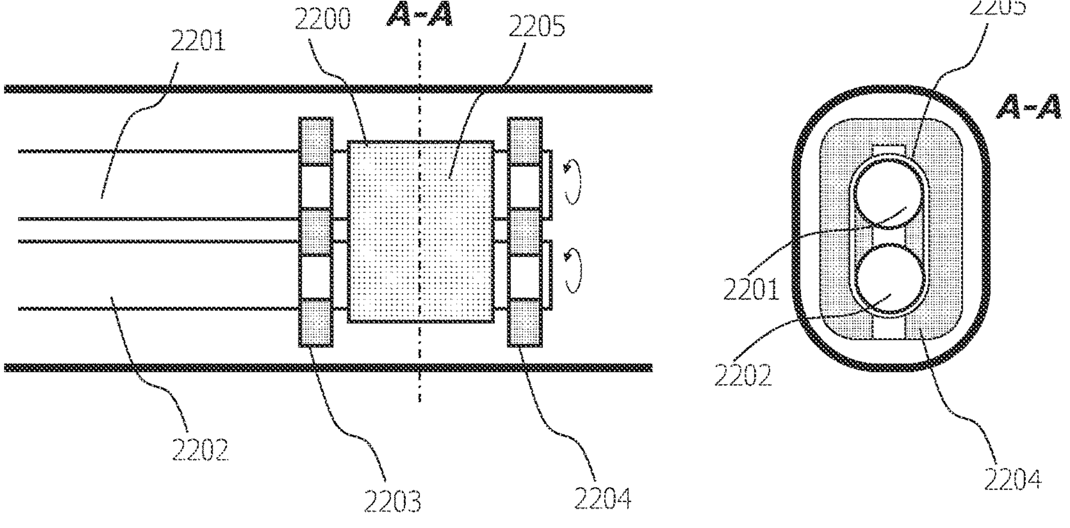
FIG. 22 illustrates another embodiment of a contralateral guidewire transmission.

FIG. 22 illustrates another embodiment of distal guidewire transmission (2200) to support transmission of rotational motion from one guidewire arm to the other. The distal ends of guidewire arms (2201, 2202) are held in a parallel configuration by retaining clips (2203, 2204). Retaining clips (2203, 2204) allow guidewire arms (2201, 2202) to rotate but not to move axially with respect to each other. In some embodiments, transmission belt (2205) is placed over the distal ends of guidewire arms (2201, 2202). Rotating first guidewire arm (2201) clockwise causes second guidewire arm (2202) to rotate clockwise. The other embodiments illustrated in FIGS. 21-22 allow for transmission of rotation from one guidewire arm to the other without twisting the guidewire assembly. The transmission of rotational motion described herein is not limited to gear wheels or belts. The transmission of rotation from one guidewire arm to the other can utilize other transmission means such as a chain, rope, magnets, a flexible torsion rod, or a combination thereof.

Figure 23:
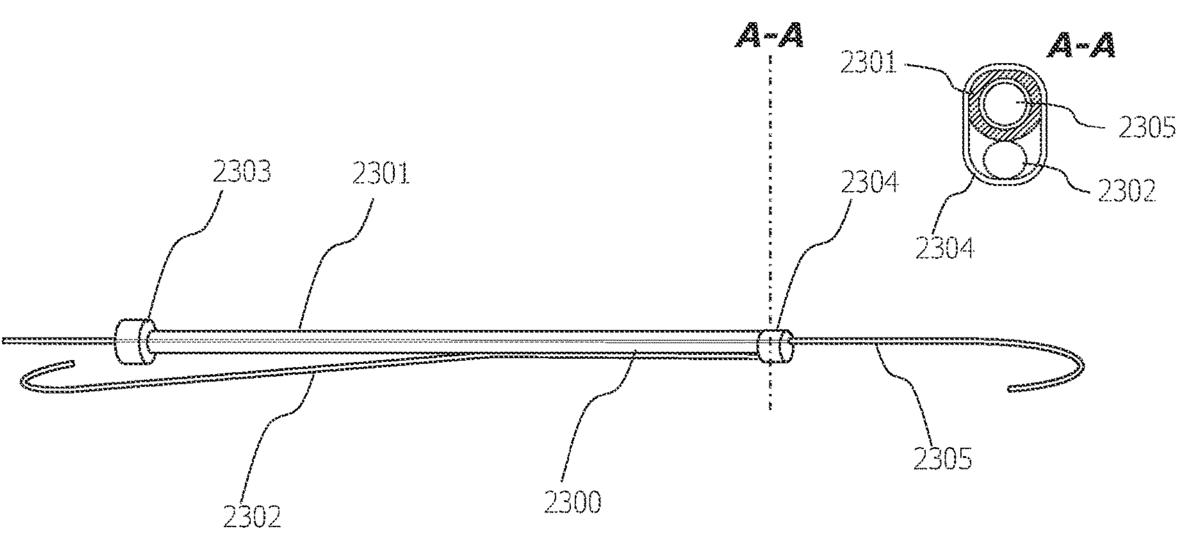
FIG. 23 illustrates an embodiment of a low-profile guidewire assembly.

FIGS. 23-24 illustrate further embodiments of the contralateral guidewire assembly designed to reduce the required outer diameter (also referred to as crossing profile) of the proximal shaft and the distal shaft to house the ipsilateral and contralateral guidewire. FIG. 23 shows contralateral guidewire assembly (2300) comprised of tubular ipsilateral arm (2301) and circular contralateral arm (2302). Tubular guidewire handle (2303) is connected to ipsilateral arm (2301) of contralateral guidewire assembly (2300). The distal ends of ipsilateral arm (2301) and contralateral arm (2302) are joined by crimp terminal (2304). The inner lumen of tubular ipsilateral arm (2301) is sufficiently large enough to house ipsilateral guidewire (2305). This coaxial arrangement reduces the cross-sectional area required to house guidewires (2300, 2305). Ipsilateral arm (2301) can be made from a metal tube or a polymeric extrusion. The polymeric extrusion can be reinforced by a wire braid. Ipsilateral arm (2301) can have slots cut perpendicular to its axis into the tube to increase its bending flexibility.

Figure 24A:
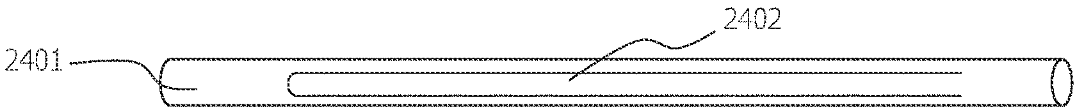
FIG. 24A illustrates another embodiment of a low-profile guidewire assembly with a tube and a flap.
Figure 24B:
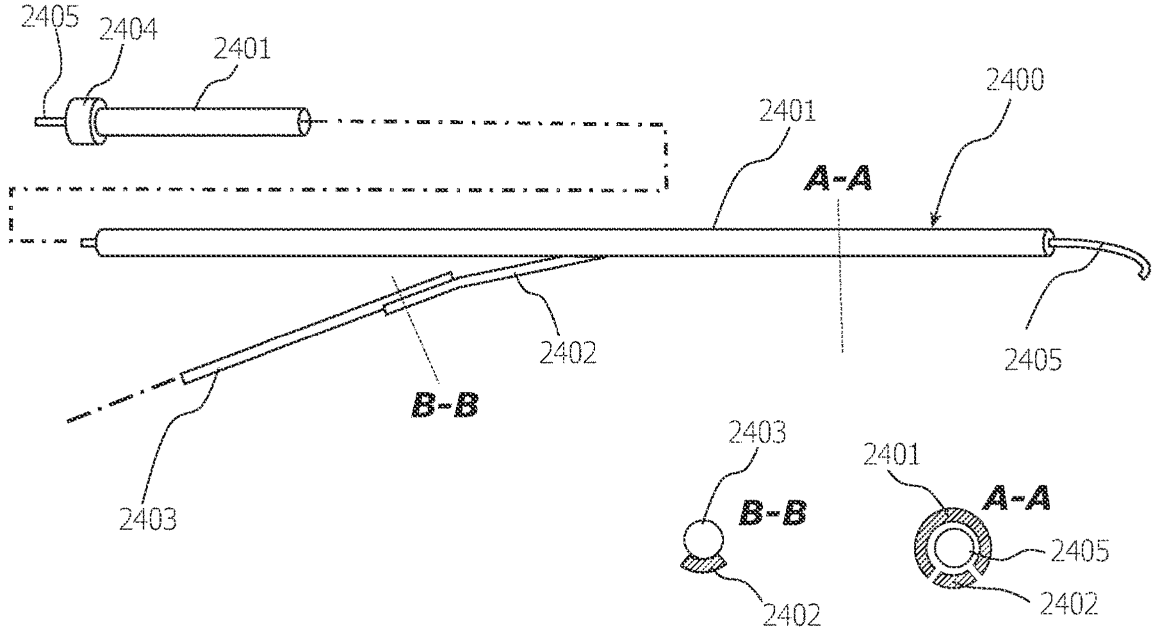
FIG. 24B illustrates the low-profile guidewire assembly of FIG. 24A with a ipsilateral arm integrated with the flap.

FIGS. 24A-B show another embodiment of the guidewire assembly designed to minimize the crossing profile of the balloon catheter. As shown in FIG. 24A, ipsilateral arm (2401) of contralateral guidewire assembly (2400) is comprised of a tube. Long flap (2402) is laser cut into the tube. FIG. 24B illustrates the integration of ipsilateral arm (2401) with flap (2402) into guidewire assembly (2400). Tubular guidewire handle (2404) is connected to the proximal end of ipsilateral arm (2401). The proximal end of flap (2402) is connected to contralateral arm (2403) of contralateral guidewire assembly (2400). Ipsilateral guidewire (2405) is coaxially arranged within tubular ipsilateral arm (2401). The guidewire assembly in FIG. 24 does not allow for rotation of the contralateral guidewire. However, it greatly minimizes the required crossing profile of the balloon catheter.

Figure 25A:
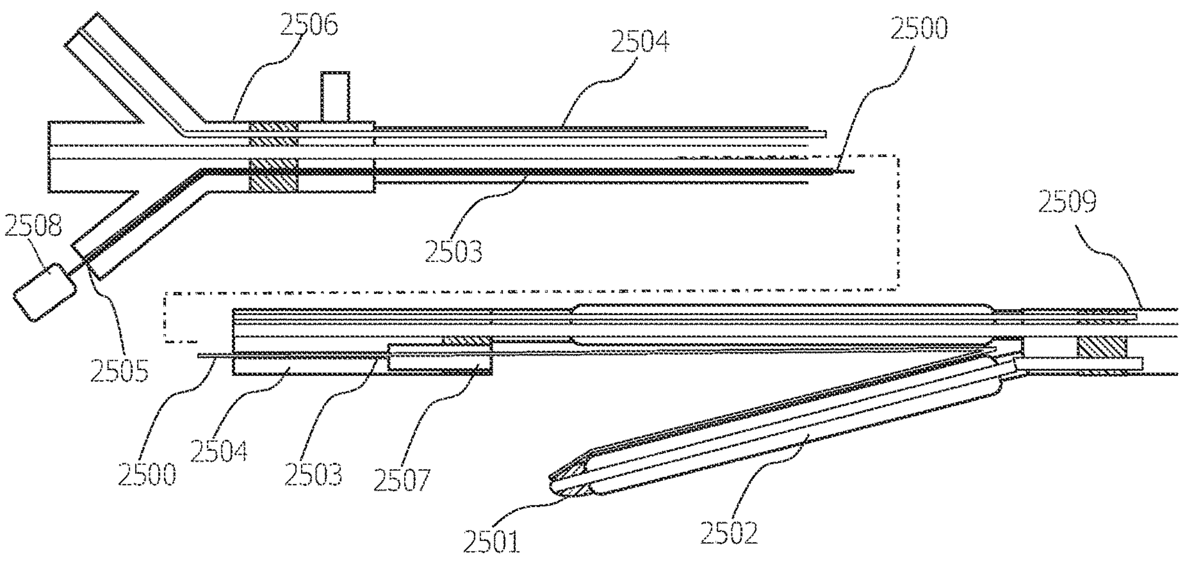
FIG. 25A illustrates a tether a pathway within a balloon catheter.
Figure 25B:
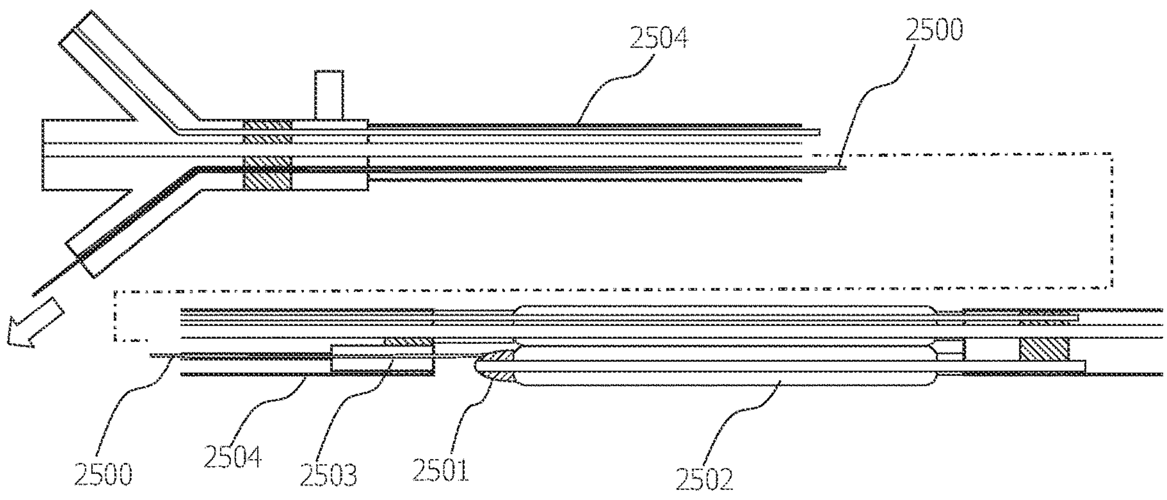
FIG. 25B illustrates the tether of FIG. 25A recapturing a contralateral balloon after deployment.

FIGS. 25A-B illustrate the tether for recapturing the contralateral balloon after stent deployment. The distal end of tether (2500) is connected to free end (2501) of contralateral balloon (2502). Tether (2500) passes through tether lumen (2503) in proximal shaft (2504) to tether port (2505) in proximal hub (2506). The distal end of tether lumen (2503) terminates in guidewire recess (2507). The proximal end of tether (2500) is connected to tether actuator (2508). Tether (2500) can be made from a braided wire, a superelastic wire, a polymeric monofilament, a fiber, a braided suture, or a combination thereof. In its undeployed configuration illustrated in FIG. 25A, tether (2500) is routed from free end (2501) of second balloon (2502) toward distal shaft (2509) and from there to guidewire recess (2507). When the bifurcated stent is crimped onto the balloon assembly, tether (2500) is passed through the contralateral branch stent over the bifurcation of the bifurcated stent and through the ipsilateral branch stent before entering guidewire recess (2507). Once the bifurcated stent is deployed, the balloon assembly is advanced into the aorta. In this position, tether (2500) is ready for deployment. FIG. 25B illustrates the deployed configuration of tether (2500). The tether actuator (not shown) is pulled proximally moving free end (2501) of contralateral balloon (2502) toward the proximal shaft (2504). In this configuration, the balloon catheter can be safely retracted into the ipsilateral iliac artery.

Figure 26A:
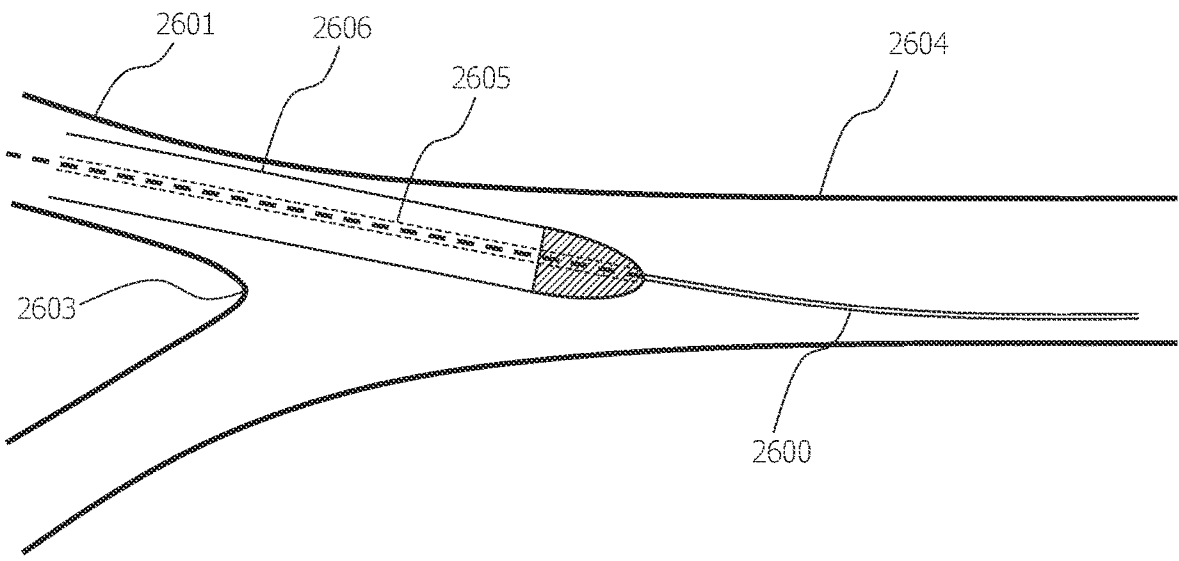
FIG. 26A illustrates advancing a balloon catheter over a guidewire to aortic bifurcation.
Figure 26B:
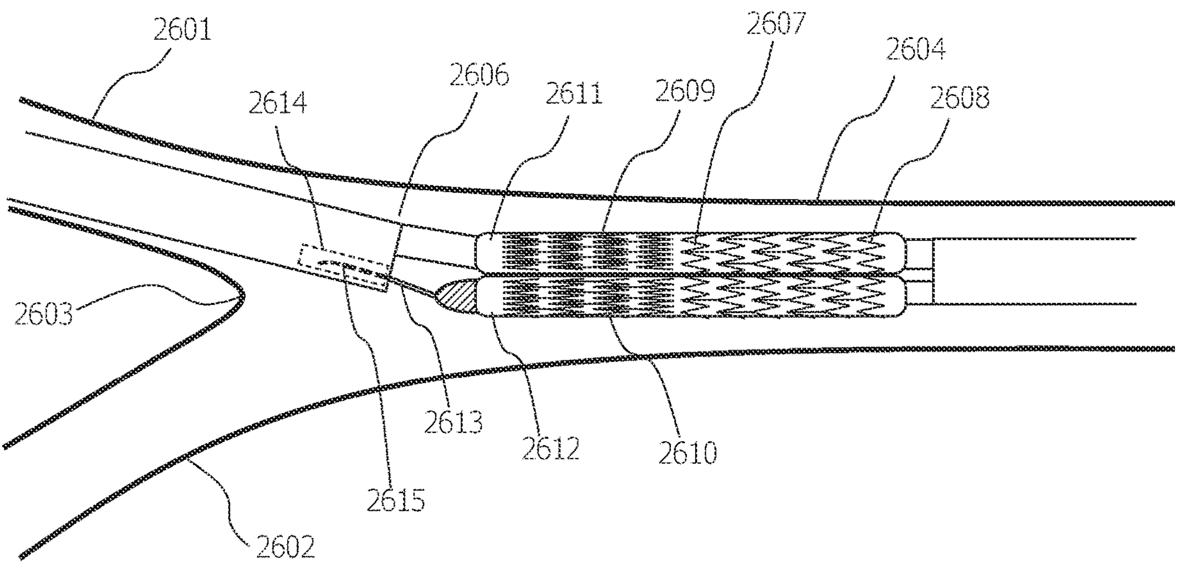
FIG. 26B illustrates a position of the balloon catheter of FIG. 26A prior to cannulation of a contralateral iliac artery.
Figure 26C:
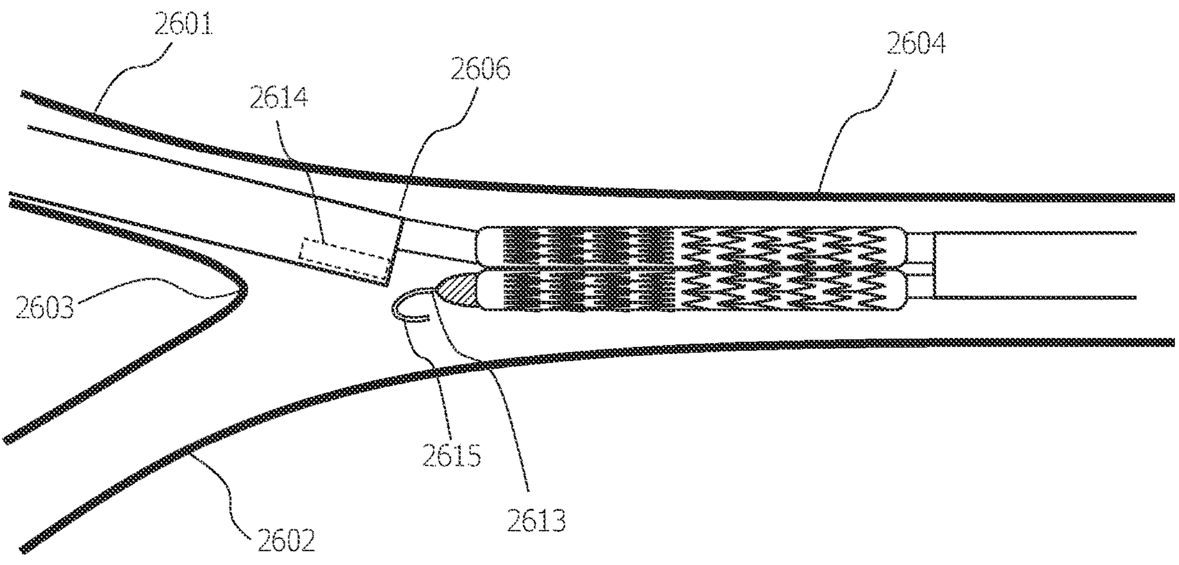
FIG. 26C illustrates advancing a contralateral guidewire of the balloon catheter of FIG. 26A to release a tip of the contralateral guidewire.
Figure 26D:
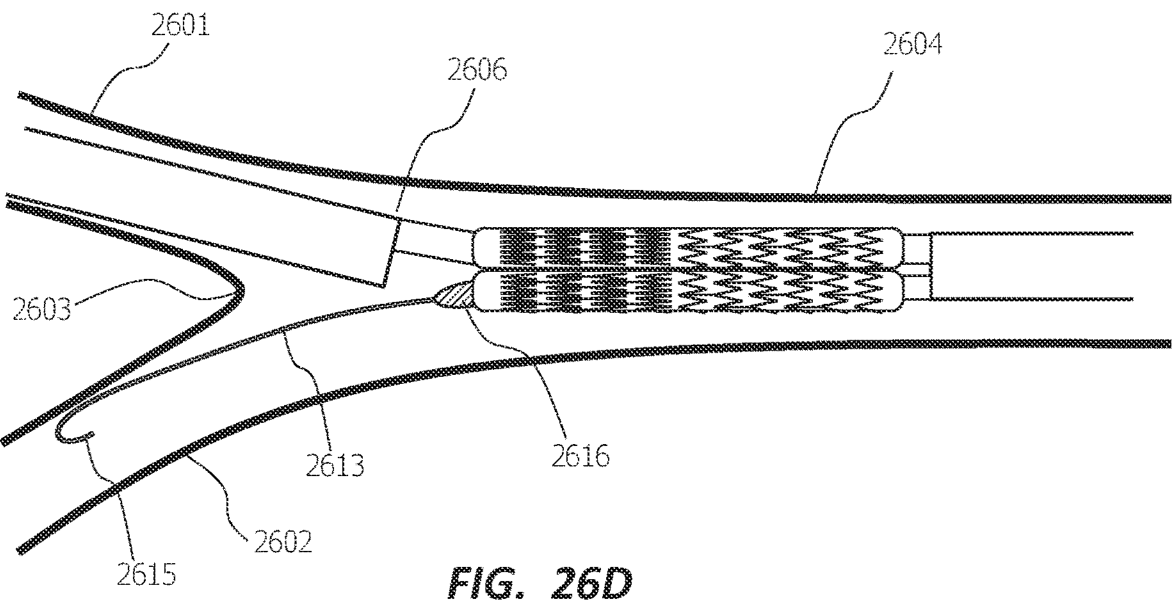
FIG. 26D illustrates advancing the contralateral guidewire of FIG. 26C into the contralateral iliac artery.
Figure 26E:
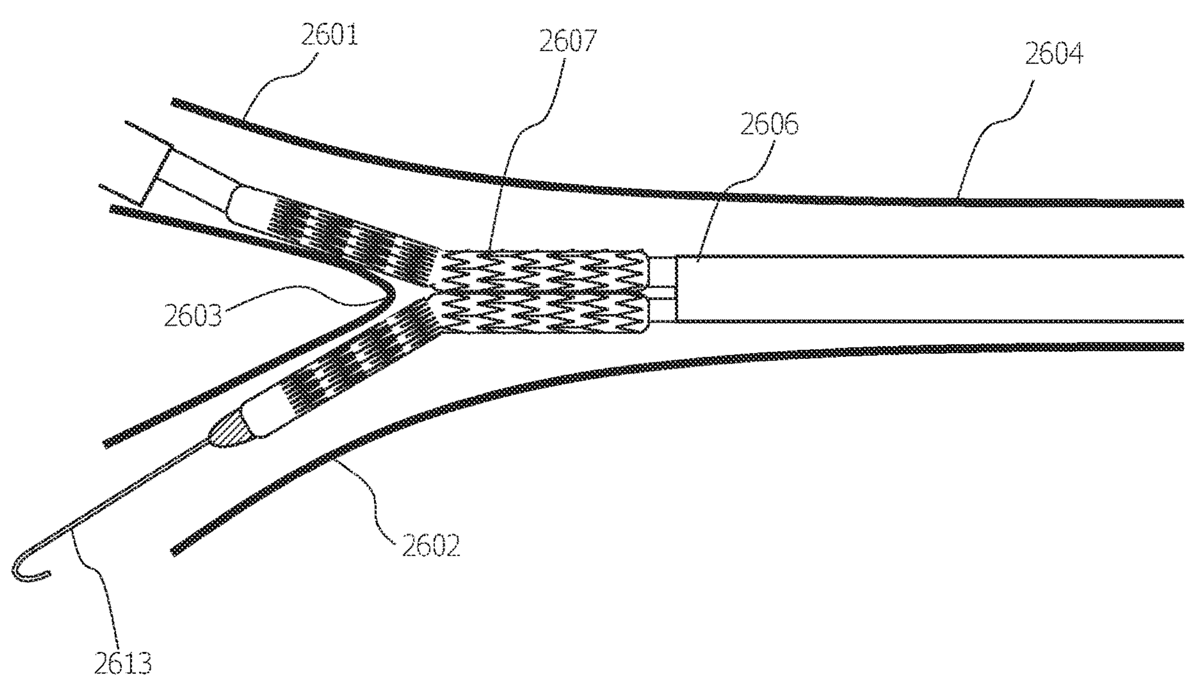
FIG. 26E illustrates advancing balloon catheter of FIG. 26A proximally until a bifurcated stent sits on the aortic bifurcation.
Figure 26F:
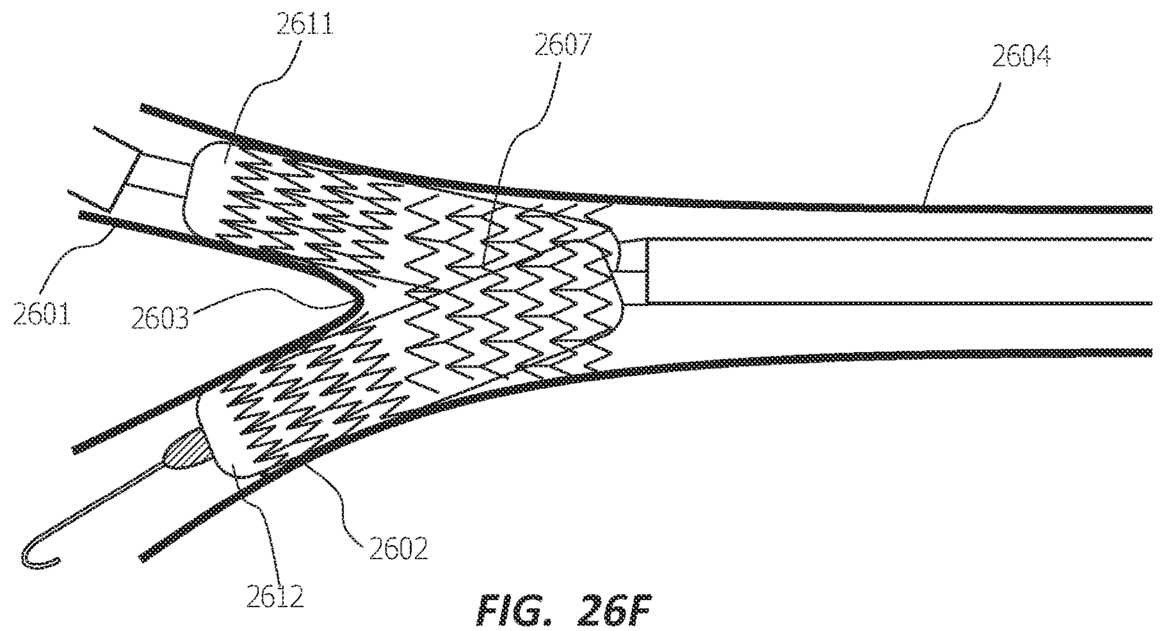
FIG. 26F illustrates inflating the balloons of the balloon catheter of FIG. 26A to expand the bifurcated stent.

FIGS. 26A-H illustrate a method of placing a bifurcated stent into the aortoiliac bifurcation using the embodiment of the balloon catheter from FIG. 1. Guidewire (2600) is inserted into the ipsilateral access vessel and advanced through ipsilateral iliac artery (2601) past aortic bifurcation (2603) into aorta (2604). The proximal end of guidewire (2600) is inserted into ipsilateral guidewire lumen (2605) of balloon catheter (2606), and balloon catheter (2606) is advanced over guidewire (2600) into aorta (2604) as shown in FIG. 26A. FIG. 26B shows the position of balloon catheter (2606) prior to cannulation of contralateral iliac artery (2602). Main body (2608) of bifurcated stent (2607) is crimped onto the distal segments of first balloon (2611) and second balloon (2612). First branch stent (2609) is crimped onto first balloon (2611), and second branch stent (2610) is crimped onto second balloon (2612). Balloon catheter (2606) is advanced distally into aorta (2604) until balloons (2611, 2612) are distal to aortic bifurcation (2603). Second balloon (2612) is oriented toward contralateral iliac artery (2602). Contralateral guidewire (2613) is in its locked position with contralateral guidewire tip (2615) retained in guidewire recess (2614). Once balloon catheter (2606) is in the correct position, contralateral guidewire (2613) is advanced distally to release contralateral guidewire tip (2615) from guidewire recess (2614) as illustrated in FIG. 26C. Contralateral guidewire (2613) is then advanced proximally and directed into contralateral iliac artery (2602) as illustrated in FIG. 26D. Contralateral guidewire (2613) may be rotated to direct contralateral guidewire tip (2615) into contralateral iliac artery (2602). Balloon catheter (2606) can be moved axially or rotated assist in directing contralateral guidewire (2613) into contralateral iliac artery (2602). To further assist in directing the contralateral guidewire (2613) toward contralateral iliac artery (2602), the contralateral arm of contralateral guidewire (2613) can have a curved proximal section to pull the contralateral arm of contralateral guidewire (2613) toward the contralateral side. In some embodiments, atraumatic tip (2616) can be curved outward to pull contralateral guidewire (2613) toward the contralateral side. In challenging anatomies, where it is difficult to advance contralateral wire (2613), a snare can be advanced from the contralateral side into contralateral iliac artery (2602) or aorta (2604). The snare can be used to capture contralateral guidewire (2603) and pull contralateral guidewire (2613) into contralateral iliac artery (2602). Once contralateral guidewire (2613) has been advanced into contralateral iliac artery (2602), balloon catheter (2606) is advanced proximally until bifurcated stent (2607) sits on aortic bifurcation (2603) as illustrated in FIG. 26E. Balloons (2611, 2612) are in a bifurcated configuration. Balloons (2611, 2612) are then inflated, and bifurcated stent (2607) is expanded and deployed into aortic bifurcation (2603) as illustrated in FIG. 26F.

Figure 26G:
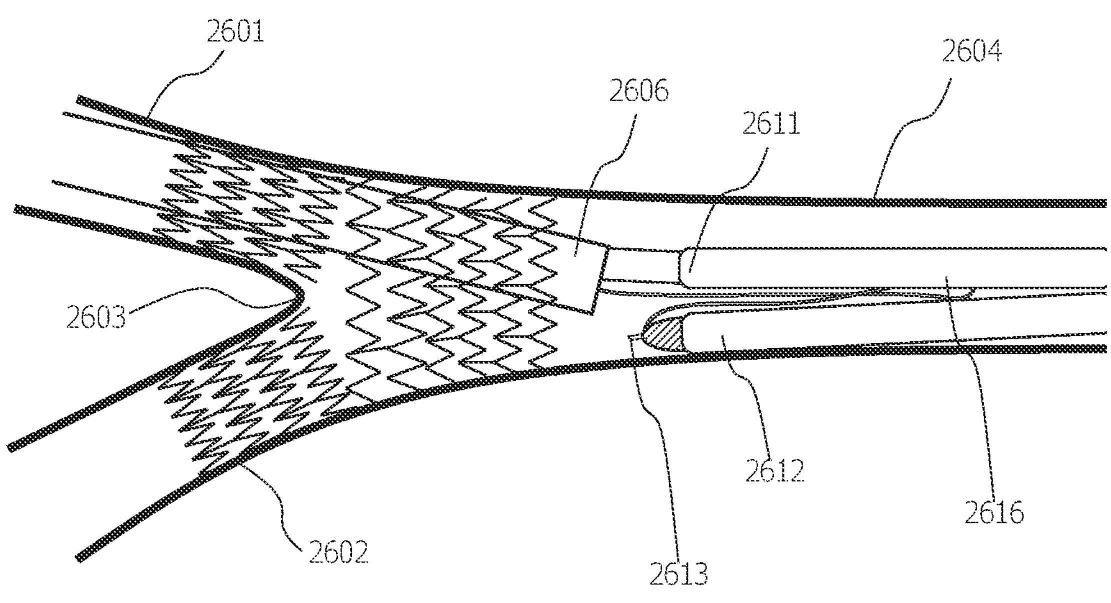
FIG. 26G illustrates the balloons of the balloon catheter of FIG. 26A deflated and the balloon catheter advanced proximally until the balloons clear the aortic bifurcation.
Figure 26H:
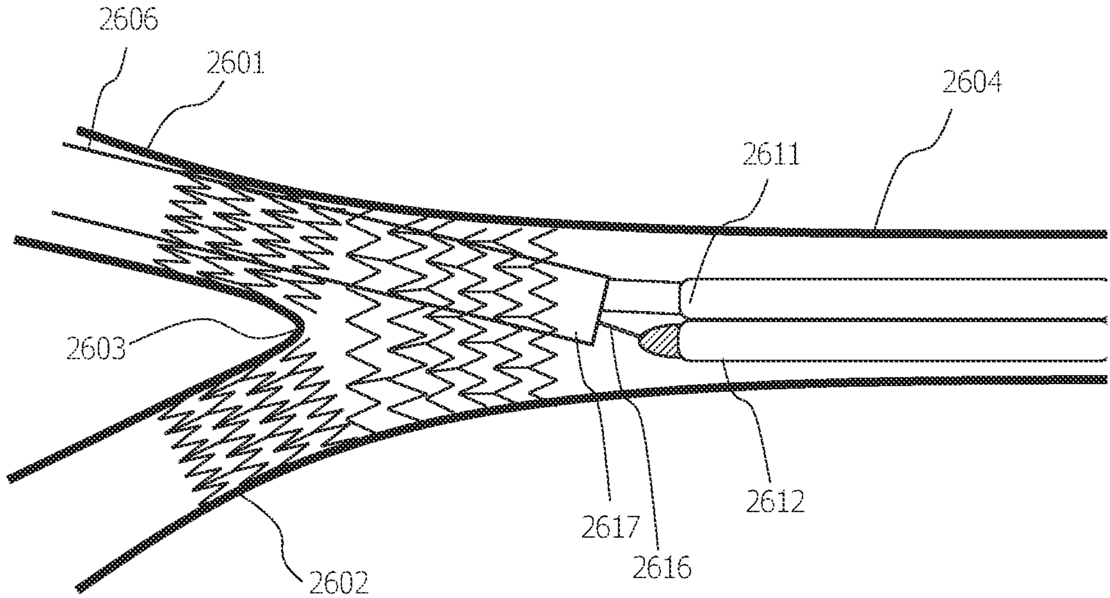

After stent deployment, balloons (2611, 2612) are deflated, balloon catheter (2606) is advanced distally until balloons (2611, 2612) clear aortic bifurcation (2603) as illustrated in FIG. 26G. Contralateral guidewire (2613) is retracted into the guidewire lumen within second balloon (2612). The distal section of tether (2616), which was sandwiched between bifurcated stent (2607) and balloons (2611, 2612) is no longer restrained. FIG. 26H shows tether (2616) retracted and the tip of second balloon (2612) moved toward the distal end of proximal shaft (2617). Balloons (2611, 2612) take on a parallel configuration. In this configuration, balloon catheter (2606) can be safely removed from the body through ipsilateral iliac artery (2601). It is understood the method of placing a bifurcated stent into the aortoiliac bifurcation can be modified by changing the sequence of steps or removing or adding steps. For example, the advancement and retraction of the balloon catheter through ipsilateral iliac artery (2601) can be facilitated by an introducer sheath through which balloon catheter (2606) is inserted. As another example, after stent deployment contralateral guidewire (2613) can be retracted into the guidewire lumen within second balloon (2612) before balloon catheter (2606) is advanced distally.

Figure 27A:
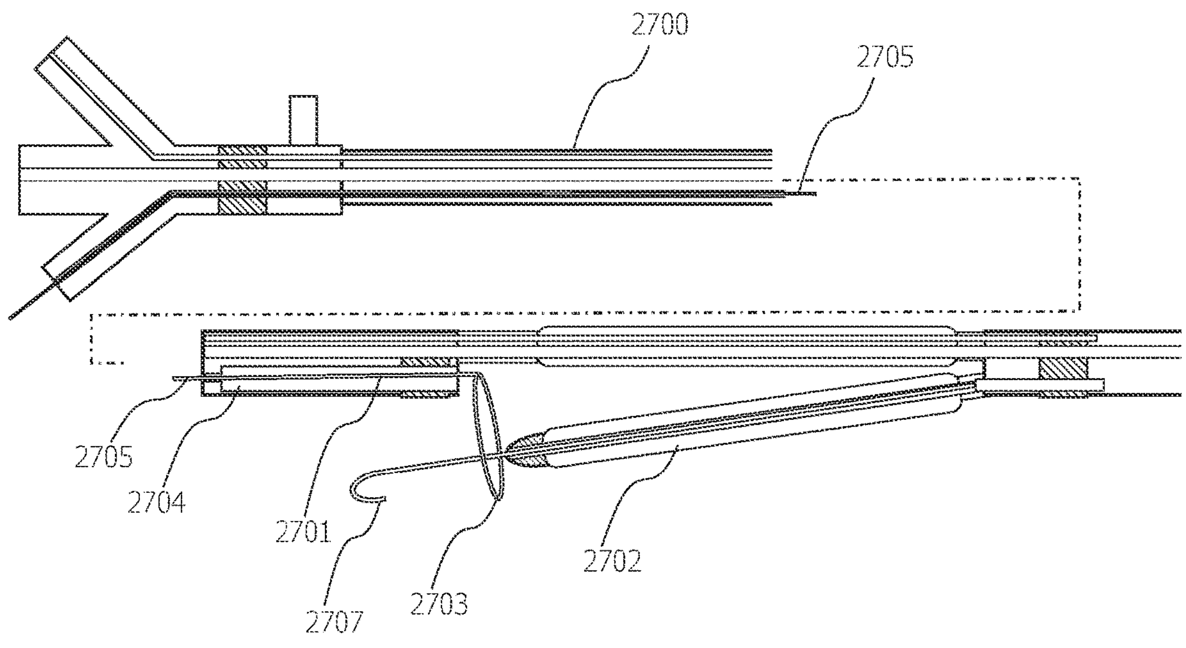
FIG. 27A illustrates another embodiment of a balloon catheter including a snare that captures an end of a balloon.
Figure 27B:
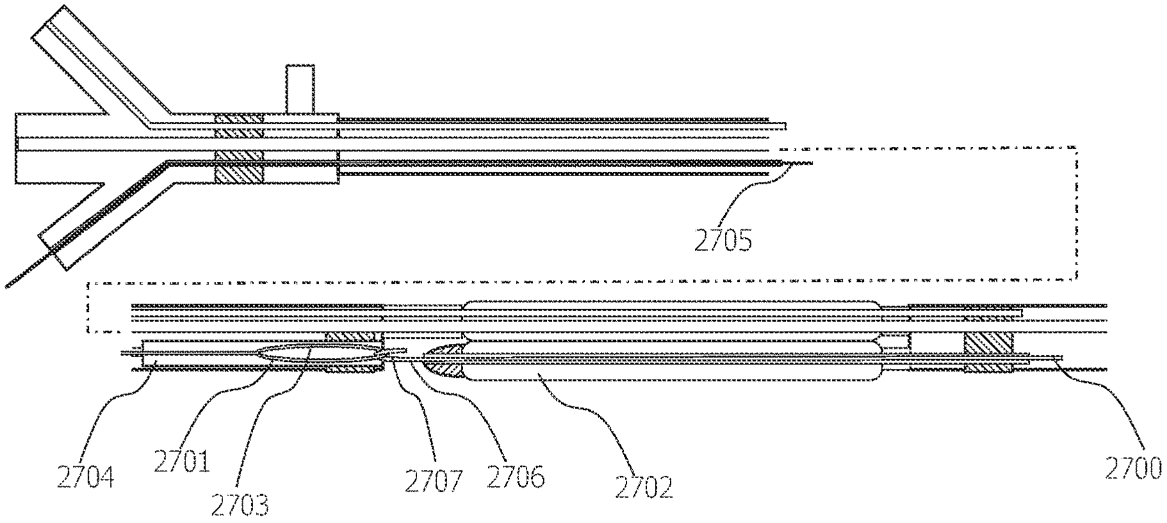
FIG. 27B illustrates the snare recaptured in a recess of the balloon catheter.

FIGS. 27A-B illustrate another embodiment of balloon catheter (2700). Instead of a tether, snare (2701) is used to recapture the free end of second balloon (2702). Snare loop (2703) is housed in extended contralateral recess (2704). Snare shaft (2705) is routed within balloon catheter (2700) similarly to tether (2500) in FIGS. 25A-B. To recapture the free end of second balloon (2702), snare loop (2703) is deployed from recess (2704) to capture contralateral guidewire (2706) as illustrated in FIG. 27A. Snare loop (2703) is arranged to form a loop substantially perpendicular to snare shaft (2705). Once contralateral guidewire (2706) is captured, snare loop (2703) and captured guidewire tip (2707) are retracted into recess (2704) as illustrated in FIG. 27B.

In another embodiment of the balloon catheter, the contralateral guidewire tip can be replaced by a snare loop. The snare loop is housed in the recess during device insertion. To position the contralateral balloon into the contralateral iliac artery, a guidewire is advanced from the contralateral side. The snare loop is removed from the recess and positioned to capture the guidewire. The snared guidewire is used to pull the second balloon into the contralateral iliac artery. After placement of the bifurcated stent, the guidewire is released from the snare loop, and the snare loop is retracted. The contralateral guidewire, the snare, and the tether described herein provide means for securing the two balloons into a first substantially parallel configuration for advancing the balloon catheter to the aortic bifurcation, releasing the contralateral balloon tip from the shaft to allow for positioning the balloons into a second bifurcated configuration for deploying the bifurcated stent, and recapturing the contralateral balloon tip for securing the balloons into a third substantially parallel configuration.

In challenging anatomies, stent delivery catheters are often advanced through a protective sheath or guide catheter to avoid the risk of stent dislodgement from the balloon. In case of AOID, the aortic bifurcation and contralateral common iliac artery can be narrow and calcified. To stent the aortic bifurcation without the risk of stent dislodgement, an introducer sheath (or guide catheter) can be advanced from the contralateral side across the lesion into the aorta. A snare can be passed through the introducer sheath to snare the contralateral guidewire of the balloon catheter described herein. With the help of the snare, the crimped contralateral branch stent is then directed into the introducer sheath and advanced into the target location protected by the sheath.

Figure 28A:
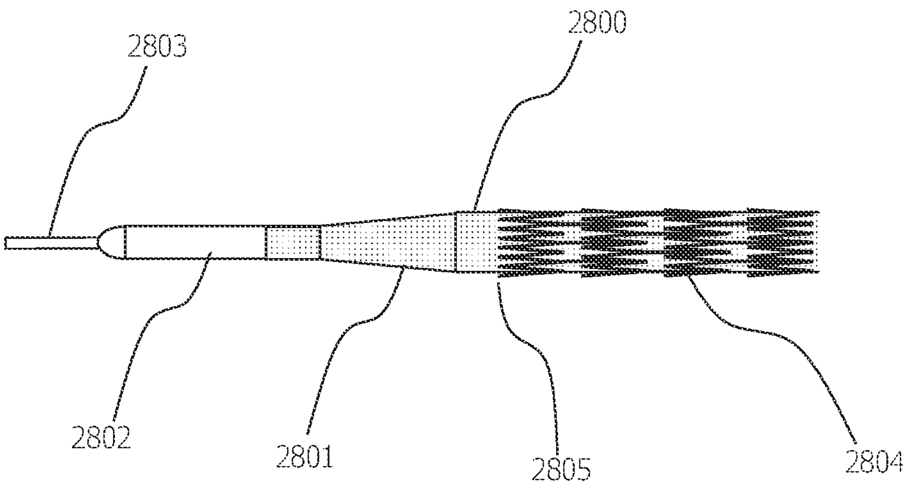
FIG. 28A illustrates an embodiment of a balloon catheter.
Figure 28B:
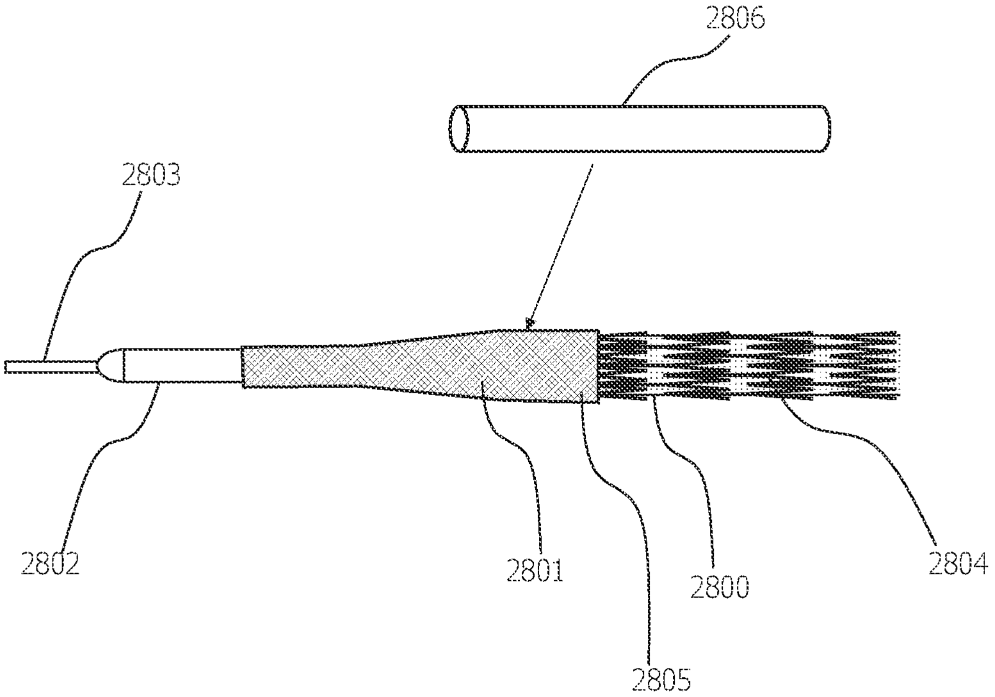
FIG. 28B illustrates the balloon catheter of FIG. 28A with a elastomeric sleeve.
Figure 28C:
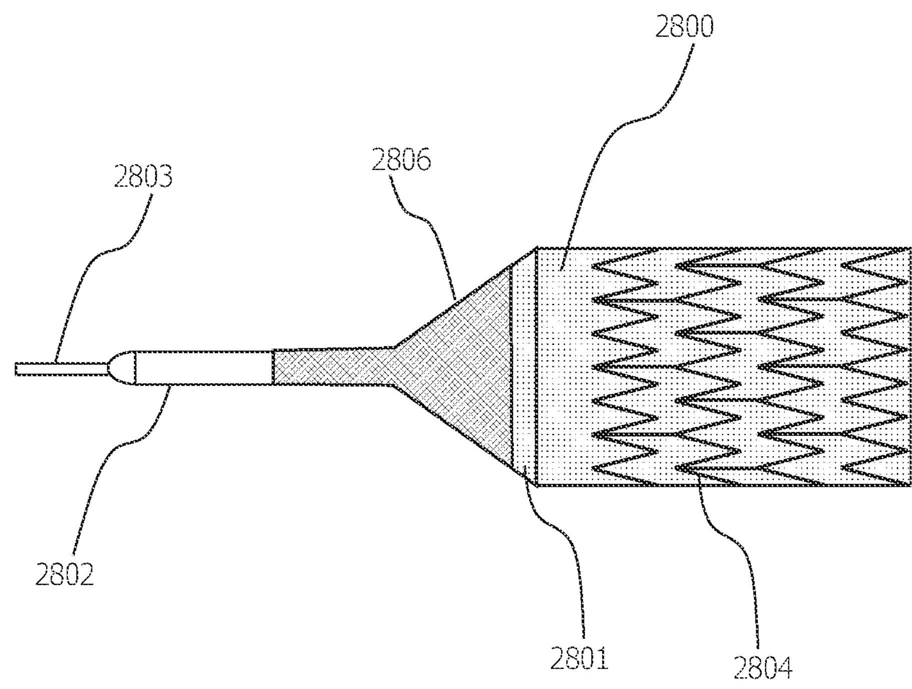
FIG. 28C illustrates a second balloon of the balloon catheter inflated with the elastomeric sleeve removed.

FIGS. 28A-C illustrate another approach to preventing stent dislodgement from the balloon. FIG. 28A illustrates the proximal end of second balloon (2800) with balloon shoulder (2801) and tip (2802), and contralateral guidewire (2803). Branch stent (2804) is crimped onto second balloon (2800). During insertion into the contralateral iliac artery, proximal end (2805) of branch stent (2804) can be pushed against calcium or plaque and become dislodged from second balloon (2800). FIG. 28B shows another embodiment comprising tubular elastomeric sleeve (2806) that is placed over the proximal end of branch stent (2804) and the proximal shoulder of second balloon (2801). The proximal end of elastomeric sleeve (2806) is bonded to contralateral tip (2802). In the crimped configuration shown in FIG. 28B, elastomeric sleeve (2806) protects proximal end (2805) of branch stent (2804) from being dislodged. When the balloon assembly is inflated to deploy the bifurcated stent, the section of elastomeric sleeve (2806) that sits on second balloon (2800) is expanded. The elastic recoil forces pull elastomeric sleeve (2806) off second balloon (2800). FIG. 28C shows the second balloon (2800) inflated. Elastomeric sleeve (2806) has slipped off balloon shoulder (2801). This self-deploying mechanism eliminates the need for an actuator to actively move the sleeve off the stent.

Figure 29A:
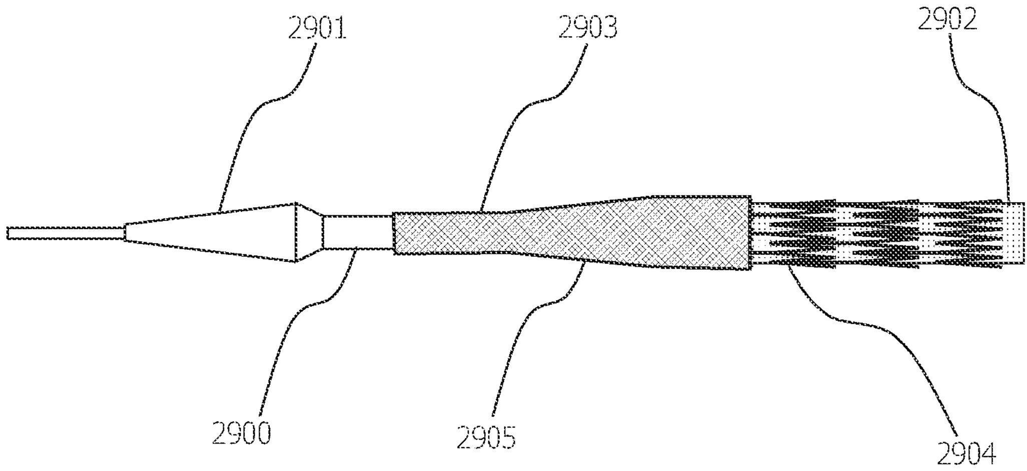
FIG. 29A illustrates another embodiment of a self-deploying sleeve.
Figure 29B:
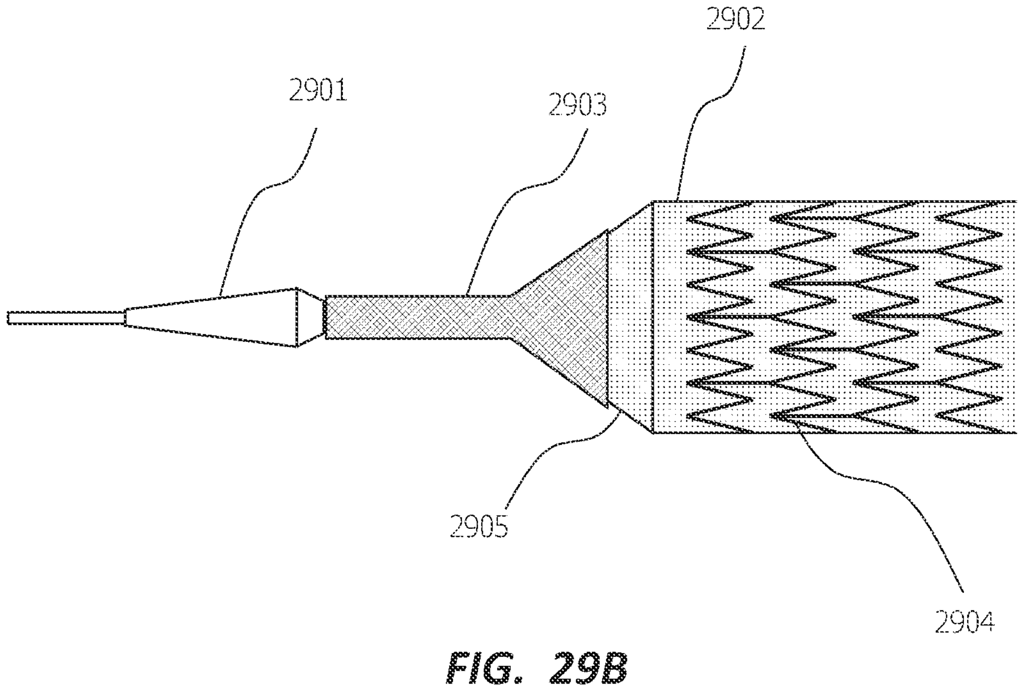
FIG. 29B illustrates the self-deploying sleeve of FIG. 29A removed off a second balloon of a balloon catheter.

FIGS. 29A-B show another embodiment of self-deploying sleeve (2903). Shaft (2900) between proximal tip (2901) and second balloon (2902) has a diameter smaller than proximal tip (2901) as illustrated in FIG. 29A. Elastomeric sleeve (2903) covers the proximal end of branch stent (2904) and second balloon shoulder (2905). Elastomeric sleeve (2903) is not bonded onto shaft (2900) and can move freely along shaft (2900). FIG. 29B shows second balloon (2902) inflated. Elastomeric sleeve (2903) has slipped off branch stent (2904) and moved toward tip (2901). The ability of elastomeric sleeve (2903) to move freely along shaft (2900) reduces the force that is required to slide elastomeric sleeve (2903) off second balloon (2902).

Figure 30:
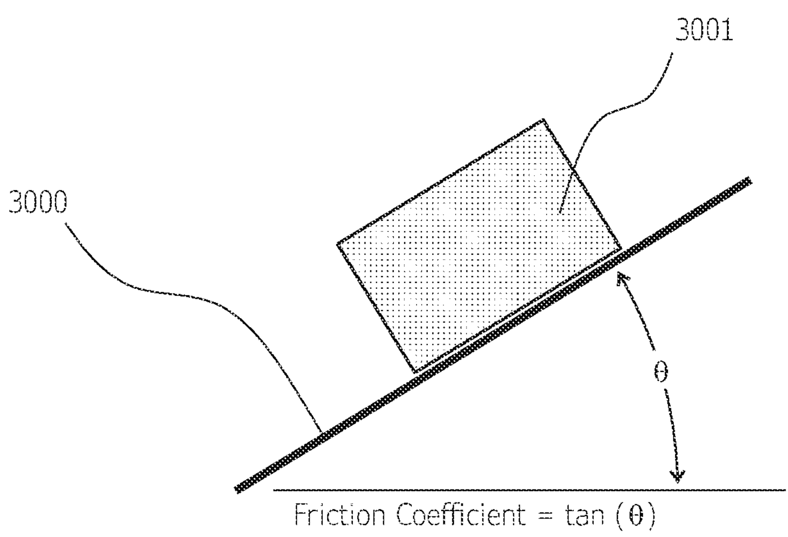
FIG. 30 illustrates the definition of a friction coefficient.
Figure 31A:
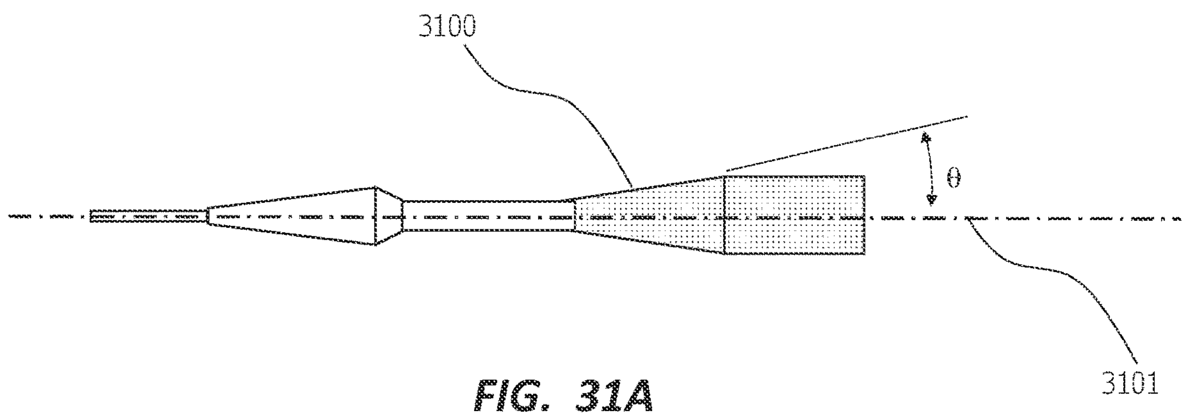
FIG. 31A illustrates a slope of a balloon shoulder in a crimped configuration.
Figure 31B:
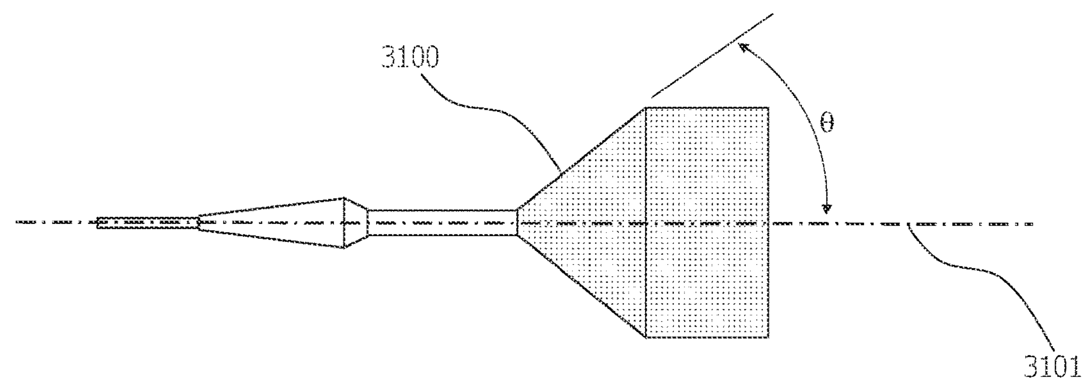

For the elastomeric sleeve to self-deploy, the friction between the sleeve and the shoulder of the balloon must be sufficiently low for the sleeve to slide down the balloon shoulder. As illustrated in FIG. 30, the friction coefficient is defined as the tangent of the slope angle 8, at which object (3001) starts sliding down ramp (3000). In case of an elastomeric sleeve mounted on a balloon, the slope angle 8 may be defined as the angle between balloon shoulder (3100) and balloon axis (3101) as shown in FIGS. 31A-B. In the crimped configuration as shown in FIG. 31A, the slope angle 8 is sufficiently small to prevent the sleeve from migrating off the balloon. The tangent of the slope angle tan(8) is less than the friction coefficient between the balloon and the elastomeric sleeve. When the balloon is inflated, the tangent of the slope angle tan(8) is greater than the friction coefficient between the balloon and the elastomeric sleeve. To ensure self-deployment of the sleeve, the friction coefficient can be lowered by using lubricous material for the balloon or sleeve or by applying a lubricant to the inner surface of the sleeve. In other embodiments, the length of the balloon shoulder can be reduced to increase the shoulder angle 8 of the inflated balloon. It is understood that the self-deploying sleeve can also be applied to the proximal end of the ipsilateral branch stent and the distal end of the main body stent. The self-deploying sleeve can be applied to the proximal or distal end of any balloon expandable stent for treating diseased vessels in the body.

Figure 32:
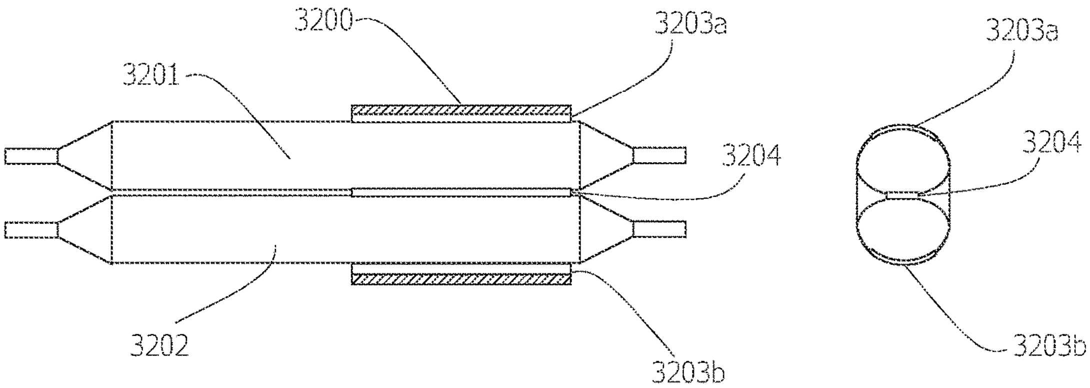
FIG. 32 illustrates the bonding of the constraining sleeve to the balloons.

In the following sections other embodiments of the bifurcated balloon assembly of the balloon catheter of the current invention are disclosed. FIG. 32 illustrates an embodiment of the balloon assembly including first balloon (3201), second balloon (3202), and constraining sleeve (3200). Constraining sleeve (3200) is bonded to first balloon (3201) and second balloon (3202) along contact lines (3203*a-b*), which are axially oriented. In addition, balloons (3201, 3202) can be bonded along their common contact line (3204) as previously described in FIG. 6B. Balloons (3201, 3202) and constraining sleeve (3200) can be bonded with an adhesive. In some embodiments, the balloons and constraining sleeve can be joined by thermo-fusion or other means.

Figure 33A:
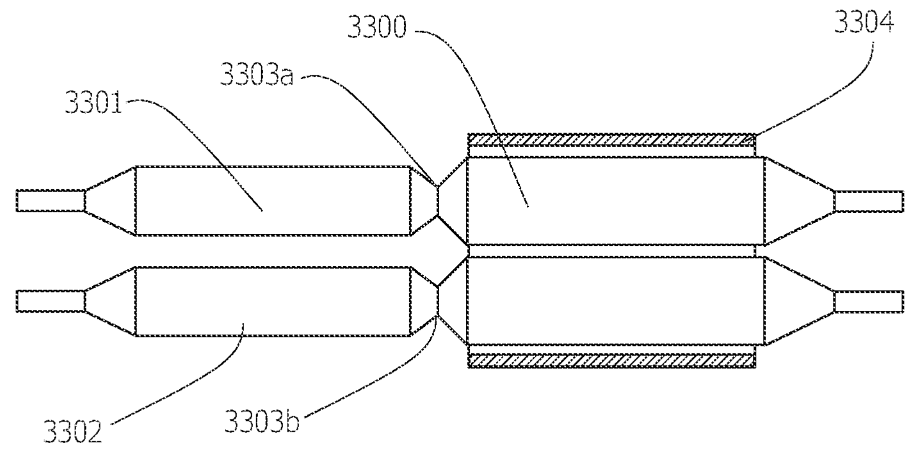
FIG. 33A illustrates an alternative shape of balloons of a bifurcated balloon assembly in a first position.
Figure 33B:
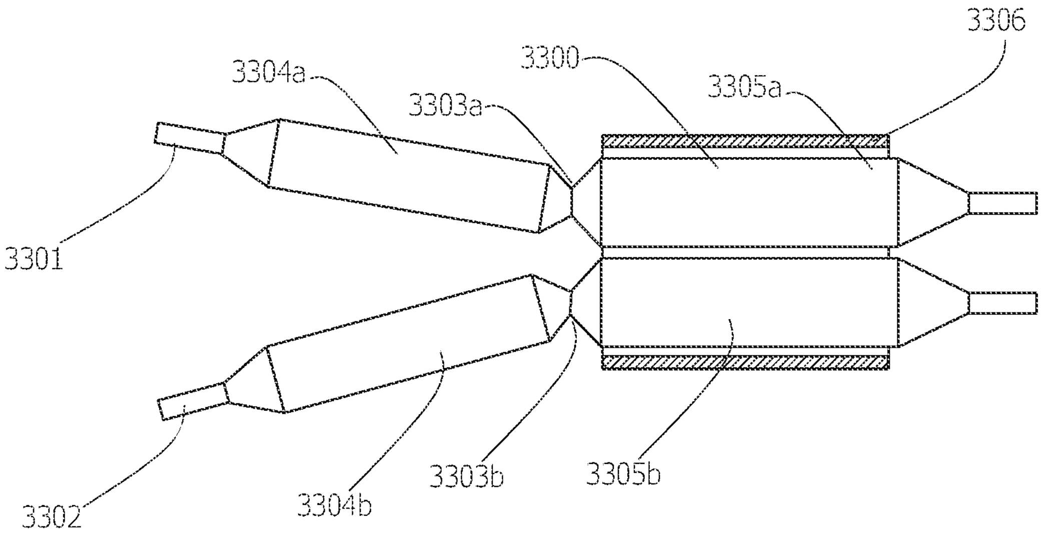
FIG. 33B illustrates the balloons of FIG. 33B in a second position.

FIGS. 33A-B illustrate another embodiment of a bifurcated balloon assembly. Bifurcated balloon assembly (3300) comprises first balloon (3301), second balloon (3302), and constraining sleeve (3304). Balloons (3301, 3302) have waists (3303*a-b*) proximal to constraining sleeve (3306). The diameter of the waists (3303*a-b*) is smaller than the diameter of the distal sections (3305*a-b*) and proximal sections (3304*a-b*) of balloons (3301, 3302). Waists (3303*a-b*) create a hinge or flex point in balloons (3301, 3302) improving the ability of the balloon assembly to conform to the angle between the iliac arteries and the aorta. In some embodiments, balloons (3301, 3302) can each comprise of two individual balloons mounted in series with the segment between the two serial balloons forming a flex point. The diameter of proximal balloon segments (3304*a-b*) can be selected to match the targeted diameters of the iliac arteries. The diameter of distal balloon segments (3305*a-b*) and sleeve (3306) can be selected to match the targeted diameter of the infrarenal aorta. For example, the non-diseased iliac arteries can be about 8 mm in diameter and the non-diseased infrarenal aorta can be about 12 mm in diameter. To conform bifurcated balloon assembly (3300) to the anatomy of the aortic bifurcation, proximal balloon segments (3304*a-b*) of a diameter of 8 mm and restraining sleeve (3306) of a diameter of 12 mm can be selected. To create a circular cross-section of restraining sleeve (3306) when bifurcated balloon assembly (3300) is inflated, the selected diameter of distal segments (3305*a-b*) can be about 9-10 mm (12 mm/1.2-12 mm/1.3). In some patients, the diameter of the aorta increases from the bifurcation toward the renal arteries. To better conform to a funnel-shaped infrarenal aorta, restraining sleeve (3306) can be tapered in shape with a larger diameter on the distal end than on the proximal end. It is understood that bifurcated balloon assembly (3300) can comprise various combinations of balloon and sleeve diameters. First balloon and the second balloon (3301, 3302) can have different diameters to individually conform to the diameters of the ipsilateral and contralateral iliac artery, respectively.

In some embodiments of the bifurcated balloon assembly, the constraining sleeve can be mounted onto the main body of the bifurcated stent. The sleeve can be mounted onto the external surface or the internal surface of the main body stent. The sleeve can comprise at least two layers with the stent sandwiched between the at least two layers. The sleeve can be made of woven PET, ePTFE, PTFE, thin-film Nitinol, polyurethane, or a combination thereof. The sleeve can comprise a netting. The sleeve can be non-complaint or semi-compliant when expanded by the two balloons. The significance of non-compliant and semi-compliant material properties is discussed below.

Figure 34:
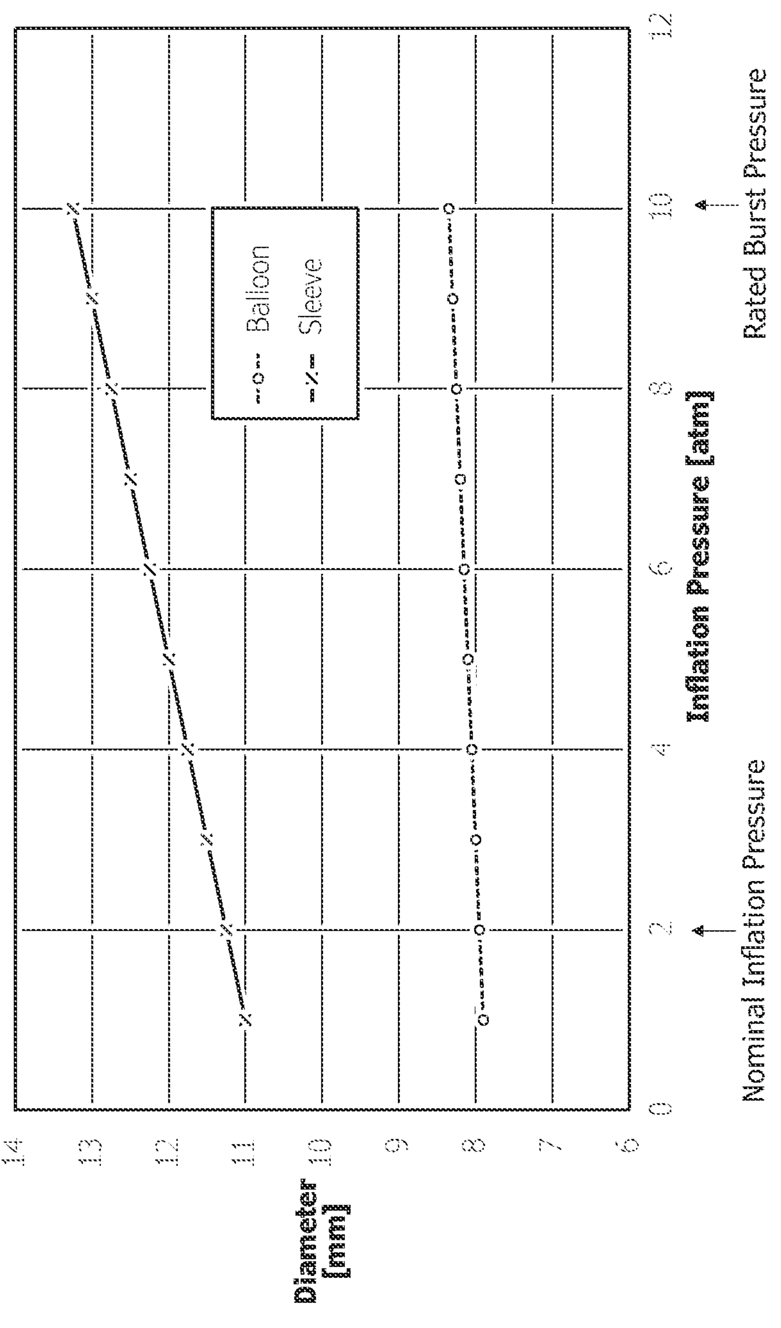
FIG. 34 illustrates compliance curves of the balloons and the sleeve of the balloon assembly.

The relationship between the diameter of the aorta and the diameter of the iliac arteries can vary from patient to patient. Providing dedicated bifurcated balloon assemblies for each possible anatomy can require a large number of balloon configurations. Described herein are embodiments of the bifurcated balloon assembly that can overcome the sizing constraints. In some embodiments of the bifurcated balloon assembly, the compliance (% change in diameter per atm) of the restraining sleeve is larger than the compliance of the two balloons. The two balloons can be non-compliant, whereas the constraining sleeve can be semi-compliant. The non-compliant balloons can be made from PET or Nylon material. The semi-compliant sleeve can be made from PEBAX or polyurethane. FIG. 34 illustrates the diameter of the two non-compliant balloons and the semi-compliant restraining sleeve as a function of the inflation pressure. Once the balloons are fully inflated to their nominal inflation pressure, the diameter of the balloons increase only marginally (<10%) when the pressure in the balloons is further increased. This is due to the non-compliant nature of the balloon material. In contrast, the diameter of the semi-compliant restraining sleeve increases substantially (>10%) with increasing pressure. In the example illustrated in FIG. 34, the restraining sleeve increases in diameter from 11.25 mm at 2 atm to 13.25 mm at 10 atm. The rate of expansion is a function of the compliance of the sleeve material.

Figure 35A:
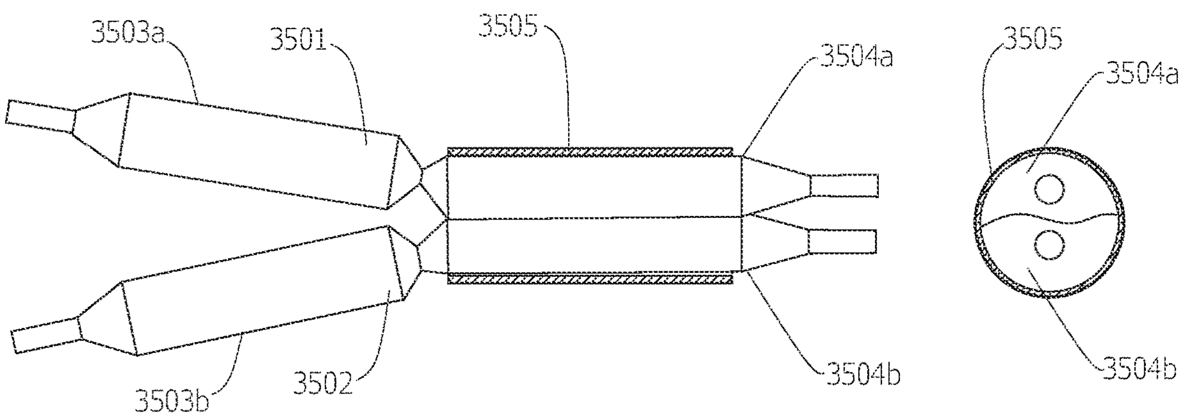
FIG. 35A illustrates a balloon assembly inflated to a first pressure.
Figure 35B:
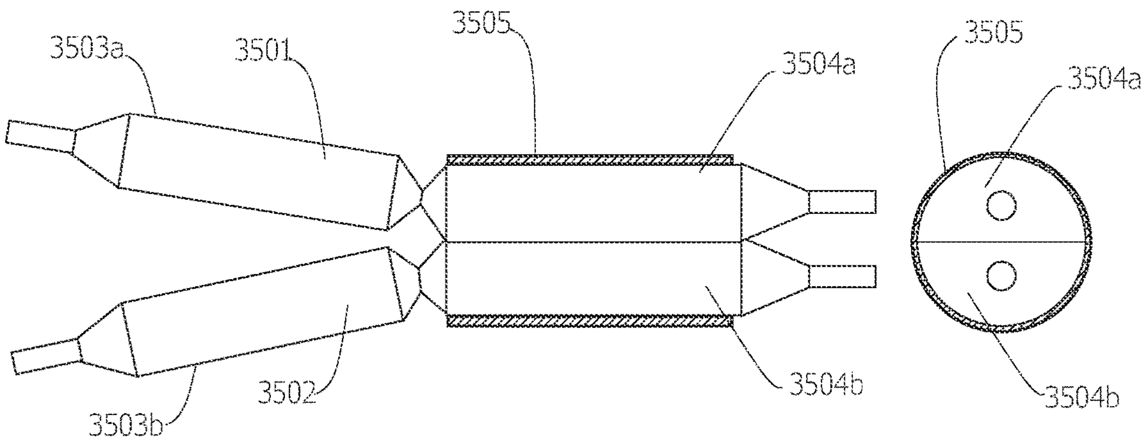
FIG. 35B illustrates the balloon assembly of FIG. 35A inflated to a second pressure.

The properties of the balloons do not influence the rate of expansion of the sleeve as long as the diameters of the balloon segments constrained by the sleeve are larger than about 13.25 mm/1.22~11 mm. This is further illustrated in FIGS. 35A-B. In FIG. 35A, balloons (3501, 3502) are inflated to their nominal pressure. Proximal segments (3503*a-b*) of balloons (3501, 3502) are expanded to their nominal diameter. Distal segments (3504*a-b*) of balloons (3501, 3502) are restrained by constraining sleeve (3505) and are under-expanded. Restraining sleeve (3505) is exposed to the full inflation pressure of balloons (3501, 3502). In FIG. 35B the inflation pressure is increased toward the rated burst pressure of balloons (3501,3502). Non-compliant proximal balloon segments (3503-*b*) closely maintain their nominal diameter. In contrast, semi-complaint sleeve (3505) expands to a larger diameter. Using a combination of non-compliant balloons and a semi-complaint sleeve, the diameter of the aortic segment of the bifurcated balloon assembly can be adjusted inter-operatively independent of the diameter of the iliac branch balloons and adapted to the diameter of the aorta. In some embodiments of the adaptive bifurcated balloon assembly, the diameter of the balloons increases by less than 10% and the diameter of the restraining sleeve increases by more than 10% when the inflation pressure is increased from the nominal inflation pressure to the rated burst pressure of the balloons. The bifurcated balloon assemblies described herein are not limited to threshold value of 10% to define non-complaint and compliant components. The threshold value for the diameter change can be about 4%, about 6%, about 8%, about 12%, about 14%, less than about 14%, or more than about 14%.

Figure 36:
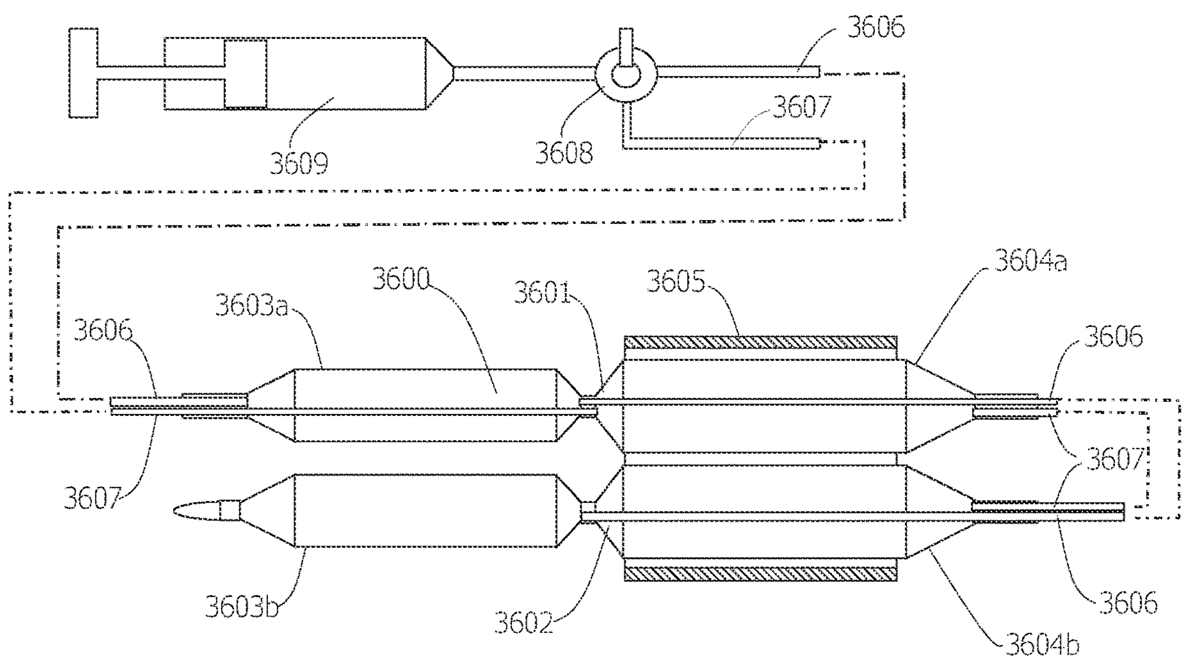
FIG. 36 illustrates an embodiment of a balloon assembly having separate inflation lumens for proximal and distal segments of balloons.

FIG. 36 illustrates another embodiment of adaptive bifurcated balloon assembly (3600) to control the diameter of the aortic balloon segment independent of the iliac branch segments. Proximal segments (3603*a-b*) of first balloon (3601) and second balloon (3602) are in fluid communication with first inflation lumen (3606), and distal segments (3604*a-b*) of first balloon (3601) and second balloon (3602) are in fluid communication with second inflation lumen (3607). Restraining sleeve (3605) is placed over distal balloon segments (3604*a-b*). Inflation lumens (3606, 3607) are connected to inflation device (3609) via three-way valve (3608). In a first step, three-way valve (3608) connects inflation device (3609) to first inflation lumen (3606) and second inflation lumen (3607). Inflation device (3609) inflates balloon assembly (3600) to the nominal inflation pressure of balloons (3601, 3602). In a second step, three-way valve (3608) connects inflation device (3609) only to second inflation lumen (3607). Distal balloon segments (3604_a-b_) are inflated to a higher pressure than the nominal inflation pressure to further expand semi-compliant sleeve (3605) to its desired diameter. Proximal balloon segments (3603_a-b_) remain inflated to their nominal diameters. These embodiments of the adaptive bifurcated balloon assembly allow for independent control of the iliac and aortic balloon pressures. If needed, the pressure in proximal balloon segments (3603_a-b_) can be further increased to treat local lesions in the iliac arteries without the risk of an aortic rupture.

Figure 37:
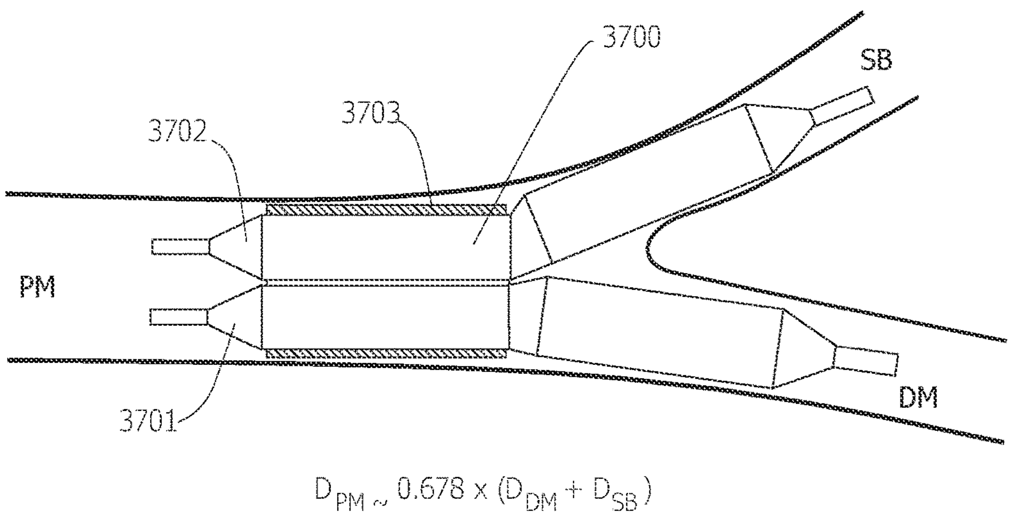
FIG. 37 illustrates a balloon assembly placed in a coronary artery bifurcation.

FIG. 37 illustrates another embodiment of the adaptive bifurcated balloon assembly. The bifurcated balloon assembly (3700) can be placed into a coronary artery bifurcation. The first balloon (3701) extends from the proximal main artery (PM) into the distal main artery (OM). The second balloon (3702) extends from the proximal main artery (PM) into the side branch (SB). The restraining sleeve is mounted onto the proximal segments of the two balloons (3701, 3702) within the PM. The diameter of the PM is about 0.678 times the sum of the diameters of the OM and SB. If the OM and SB are of similar diameter, the diameter of the PM is about 1.2-1.3 that of the OM or SB. This diameter relationship is similar to the diameter relationship between the balloons and the restraining sleeve of the bifurcated balloon assembly illustrated in FIG. 8. Thus, the bifurcated balloon assemblies described herein are well suited for treating coronary artery bifurcations. In some embodiments, first balloon (3701) and restraining sleeve (3703) are non-compliant, and second balloon (3702) is semi-compliant. This allows for adjustment of the balloon segment in the SB independent of the diameter of the main artery segments PM and OM.

Figure 38:
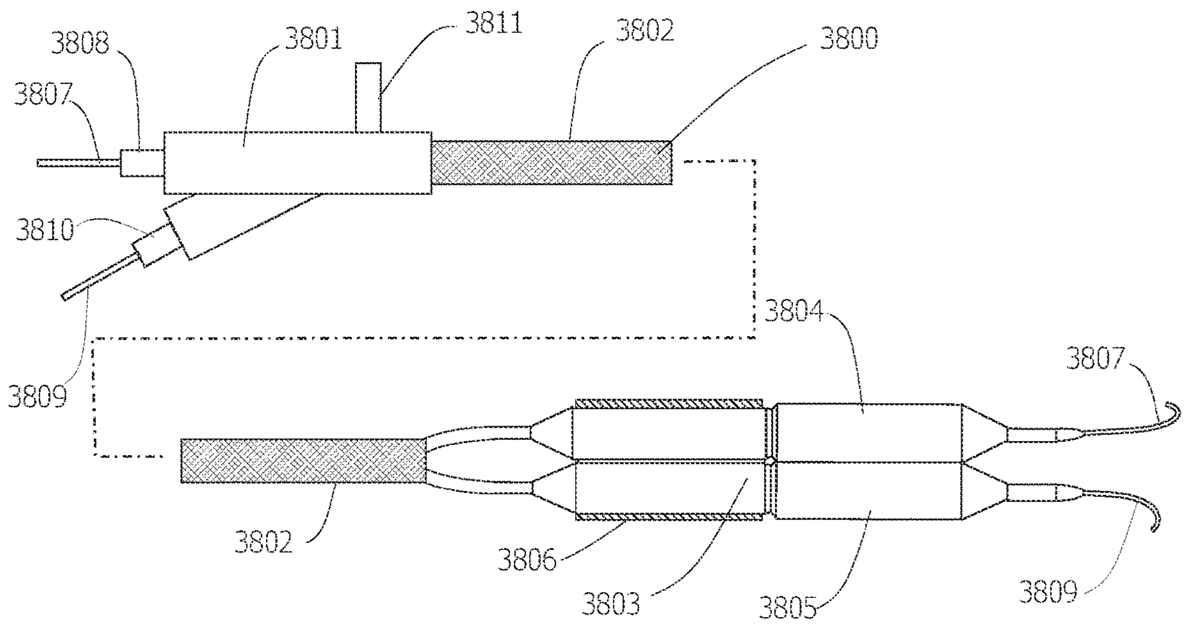
FIG. 38 illustrates a balloon catheter described herein for the treatment of a coronary artery bifurcation.

The exemplary embodiments of the balloon catheter described in the previous sections can be used for delivering a bifurcated balloon assembly from one branch vessel to the vessel bifurcation. FIG. 38 illustrates an embodiment of the balloon catheter described herein for delivering the bifurcated balloon assembly from the main vessel into the vessel bifurcation. For example, this approach is taken in coronary artery interventions. Balloon catheter (3800) comprises proximal hub (3801), catheter shaft (3802), and bifurcated balloon assembly (3803). Bifurcated balloon assembly (3803) is comprised of first balloon (3804) and second balloon (3805), and restraining sleeve (3806) mounted over the proximal segments of balloons (3804, 3805). Balloon catheter (3800) houses first guidewire (3807) that passes from first guidewire port (3808) in the proximal hub (3801) through the catheter shaft (3802) to the distal tip of first balloon (3804) and second guidewire (3809) that passes from second guidewire port (3810) in proximal hub (3801) through catheter shaft (3802) to the tip of second balloon (3805). Inflation port (3811) is in fluid communication with the first balloon and second balloon (3804, 3805). In case of coronary artery interventions, first guidewire (3807) can be advanced into distal main artery (OM), second guidewire (3809) can be advanced into side branch (SB). Balloon catheter (3800) is then advanced over guidewires (3807, 3809) into the coronary bifurcation.

It is understood that FIG. 38 only presents one possible embodiment of a catheter for placement of a bifurcated balloon assembly from a main vessel into a vessel bifurcation. The embodiment of the balloon catheter in FIG. 38 and the embodiment of the balloon catheter in FIG. 1 and FIG. 16 demonstrate that the balloon assembly described herein can be delivered into a vessel bifurcation from any of the three vessels that meet at the bifurcation. It is understood that the incorporation of the bifurcated balloon assembly into a catheter for the treatment of vessel bifurcation is not limited to the embodiments presented in FIG. 1, FIG. 16, and FIG. 38. It is further understood that the combination of non-compliant or semi-compliant balloons, non-complaint or semi-complaint restraining sleeves, and separate inflation lumens for the various balloon segments allow for the design of a wide range of adaptive bifurcated balloon assemblies. A bifurcated balloon assembly is considered adaptive if it at least comprises a first balloon, a second balloon arranged in part in parallel to the first balloon, a restraining sleeve partially placed over the first and the second balloon, wherein at least one of the three components is made from non-compliant material and at least one component is made from semi-compliant material.

Figure 39:
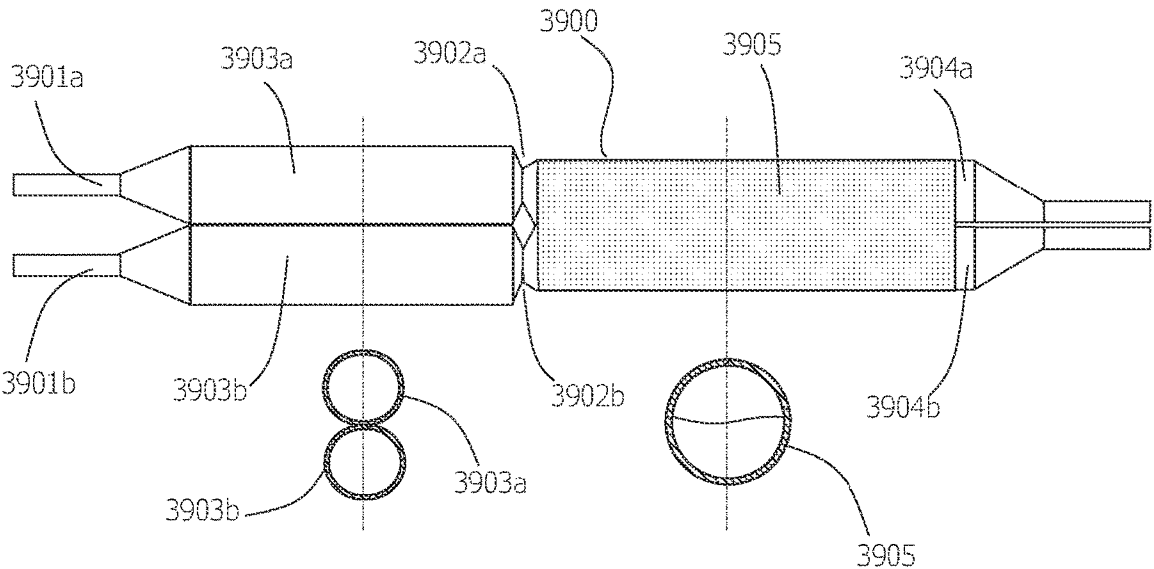
FIG. 39 illustrates another embodiment of a bifurcated balloon assembly.

FIG. 39 illustrates the inflated configuration of an embodiment of the bifurcated balloon assembly described herein for the deployment of a balloon-expandable bifurcated stent. Bifurcated balloon assembly (3900) comprises of cylindrical balloons (3901_a-b_) that are arranged substantially in parallel. Balloons (3901_a-b_) comprise of waists (3902_a-b_) that divide balloons (3901_a-b_) into proximal balloon segments (3903_a-b_) and distal balloon segments (3904_a-b_). Waists (3902_a-b_) create flex points in balloon assembly (3900) at the bifurcation. The flex points allow inflated proximal segments (3903_a-b_) to angle away distal segments (3904_a-b_). Tubular restraining sleeve (3905) covers both distal balloon segments (3904_a-b_). Restraining sleeve (3905) can have a diameter that is less than about 1.6 times the diameter of distal balloon segments (3904_a-b_) in order to restrain the expansion of distal balloon segments (3904_a-b_). When the diameter of restraining sleeve (3905) is between about 1.22 and about 1.6 times the diameter of distal balloon segments (3904_a-b_), restraining sleeve (3905) takes on an oval cross-sectional shape when balloons (3901_a-b_) are inflated. When the diameter of restraining sleeve (3905) is less than about 1.22 times the diameter of distal balloon segments (3904_a-b_), restraining sleeve (3905) takes on a substantially circular cross-section when the balloons (3901_a-b_) are inflated as shown in FIG. 39.

Figure 40:
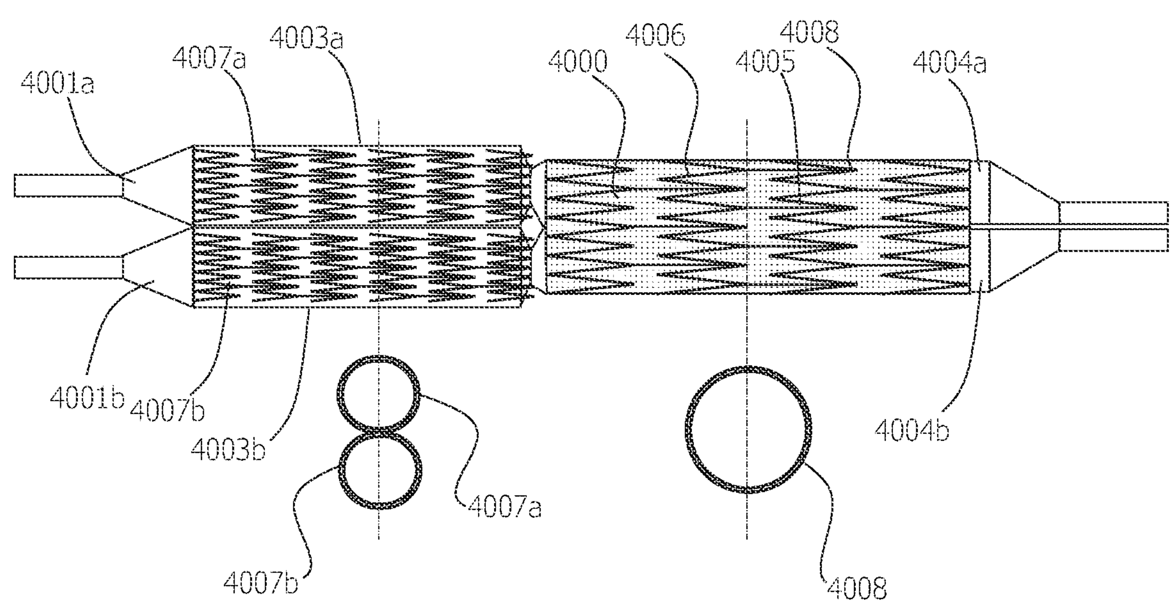
FIG. 40 illustrates a bifurcated stent placed onto a bifurcated balloon assembly of FIG. 39.

FIG. 40 illustrates bifurcated stent (4006) expanded by bifurcated balloon assembly (4000) of FIG. 39. Bifurcated stent (4006) comprises branch stents (4007_a-b_) and main body stent (4008). First branch stent (4007_a_) is crimped onto proximal segment (4004_a_) of first balloon (4001_a_) and second branch stent (4007_b_) is crimped onto proximal segment (4004_b_) of second balloon (4001_b_). Main body stent (4008) is crimped onto restraining sleeve (4005). Inflating balloons (4001_a-b_) expand branch stents (4007_a-b_) to the diameter of proximal balloon segments (4003_a-b_) and main body stent (4008) to the diameter of restraining sleeve (4005).

Figure 41:
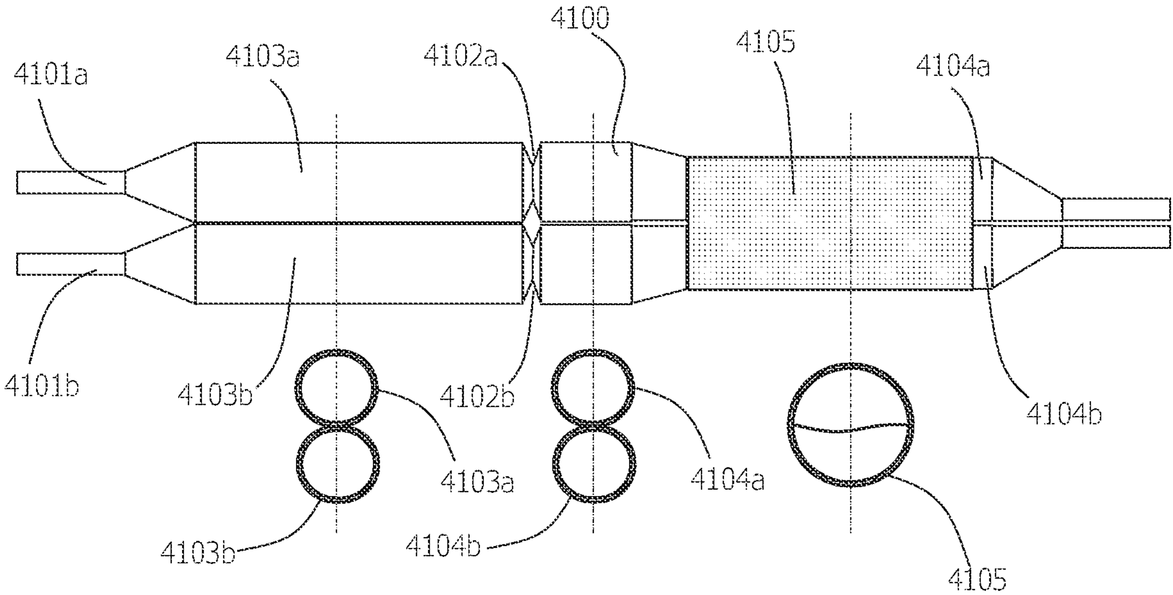
FIG. 41 illustrates another embodiment of a bifurcated balloon assembly.

FIG. 41 illustrates another embodiment of the bifurcated balloon assembly described herein. Bifurcated balloon assembly (4100) comprises cylindrical balloons (4101_a-b_) that are arranged substantially in parallel. Balloons (4101_a-b_) comprise waists (4102_a-b_) that divide the balloons (4101_a-b_) into proximal segments (4103_a-b_) and distal segments (4104_a-b_). In some embodiments, as illustrated in FIG. 41 tubular restraining sleeve (4105) only partially covers distal balloon segments (4104_a-b_). In other embodiments, the tubular restraining sleeve can substantially cover the distal balloon segments. In some embodiments, the tubular restraining sleeve can completely cover the distal balloon segments. The proximal ends of distal balloon segments (4104_a-b_) are not covered by restraining sleeve (4105). When the diameter of restraining sleeve (4105) is less than about 1.22 times the diameter of distal segments (4104*a-b*) of balloons (4101*a-b*), sleeve (4105) takes on a substantially circular shape when balloons (4101*a-b*) are inflated as shown in FIG. 41. The unrestrained proximal sections of distal balloon segments (4104*a-b*) form a double-barrel shaped cross-section.

Figure 42:
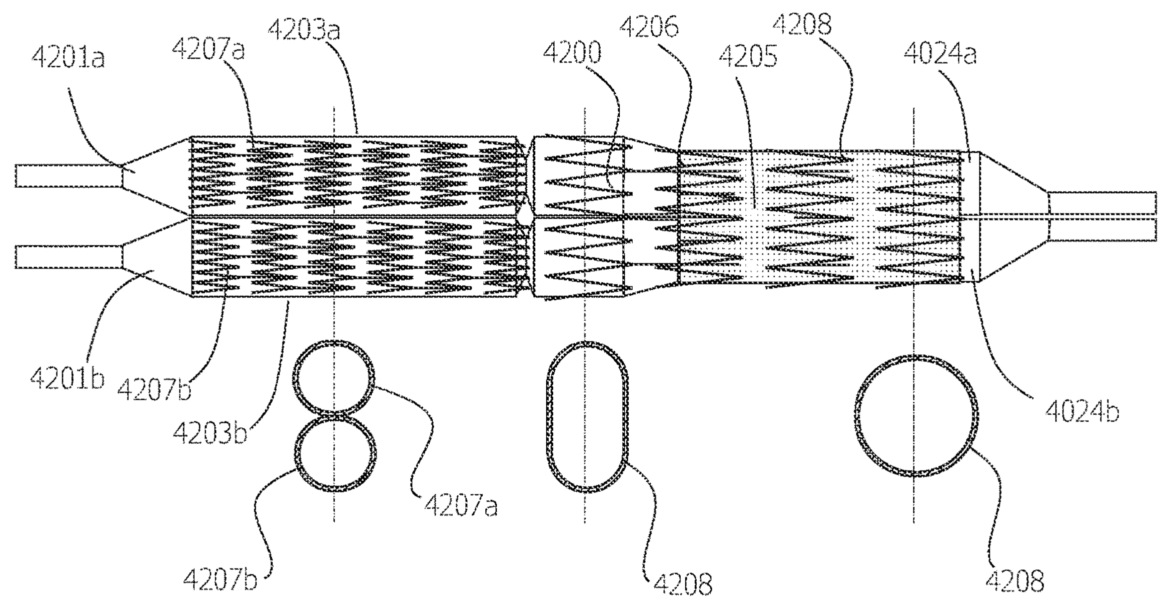
FIG. 42 illustrates a bifurcated stent placed onto the bifurcated balloon assembly of FIG. 41.

FIG. 42 illustrates bifurcated stent (4206) expanded by bifurcated balloon assembly (4200). Bifurcated balloon assembly (4200) is identical to bifurcated balloon assembly (4100) illustrated in FIG. 41. Bifurcated stent (4206) comprises branch stents (4207*a-b*) and main body stent (4208). First branch stent (4207*a*) is crimped onto proximal segment (4203*a*) of first balloon (4201*a*). Second branch stent (4207*b*) is crimped onto proximal segment (4203*b*) of second balloon (4201*b*). Main body stent (4208) is crimped onto distal balloon segments (4204*a-b*). Inflating balloons (4201*a-b*) expand branch stents (4207*a-b*) to the diameter of proximal balloon segments (4203*a-b*), the proximal end of main body stent (4208) into an oval shape and the mid-section and distal end of main body stent (4208) to the diameter of restraining sleeve (4205). In some embodiments, the bifurcated stent can be covered with a biocompatible material such as ePTFE. When deployed into the aortic bifurcation, the bifurcated stent creates a bifurcating flow channel for the blood passing from the aorta into the iliac artery. The flow channel created by expanding the covered bifurcated stent with bifurcated balloon assembly (4200) of FIG. 42 can provide improved flow conditions at the bifurcation and less flow stagnation and flow disturbances at the entry into the branch stent.

Figure 43:
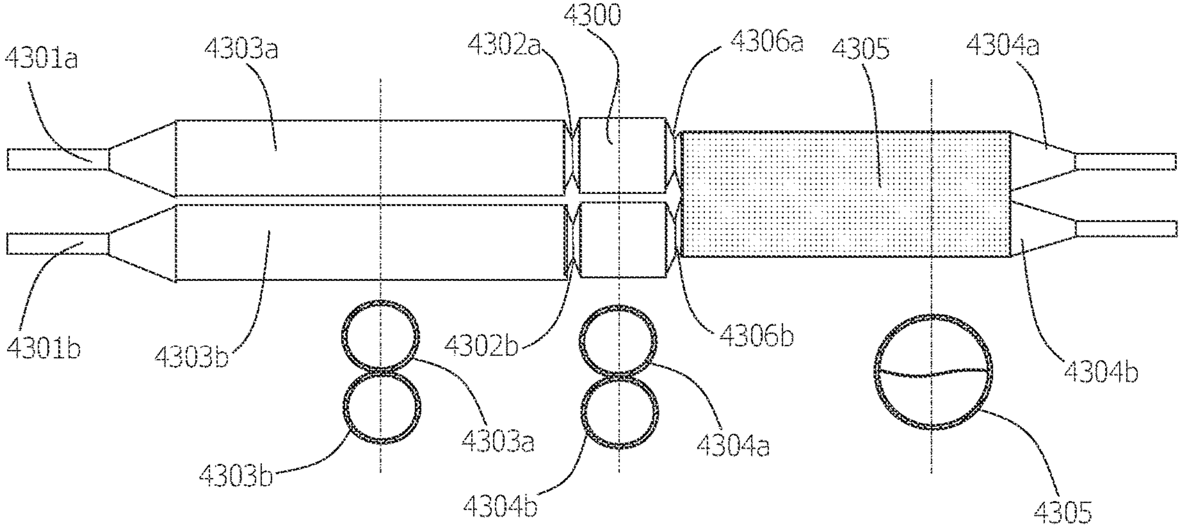
FIG. 43 illustrates another embodiment of a bifurcated balloon assembly as described herein.

FIG. 43 illustrates another embodiment of the bifurcated balloon assembly described herein. Bifurcated balloon assembly (4300) comprises cylindrical balloons (4301*a-b*) that are arranged substantially in parallel. Balloons (4301*a-b*) comprise first waists (4302*a-b*) that divide balloons (4301*a-b*) into proximal segments (4303*a-b*) and distal segments (4304*a-b*). Tubular restraining sleeve (4305) only partially covers distal balloon segments (4304*a-b*). Second waists (4306*a-b*) are placed between the unconstrained and the constrained sections of distal balloon segments (4304*a-b*). The embodiment of the bifurcated balloon assembly as illustrated in FIG. 43 reduces tensile strains in the proximal end of the sleeve and reduces balloon distortions at the transition from the unconstrained to the constrained sections of distal balloon segments (4304*a-b*). Distortions and high tensile strains can reduce the rated burst pressure of the bifurcated balloons assembly.

Figure 44:
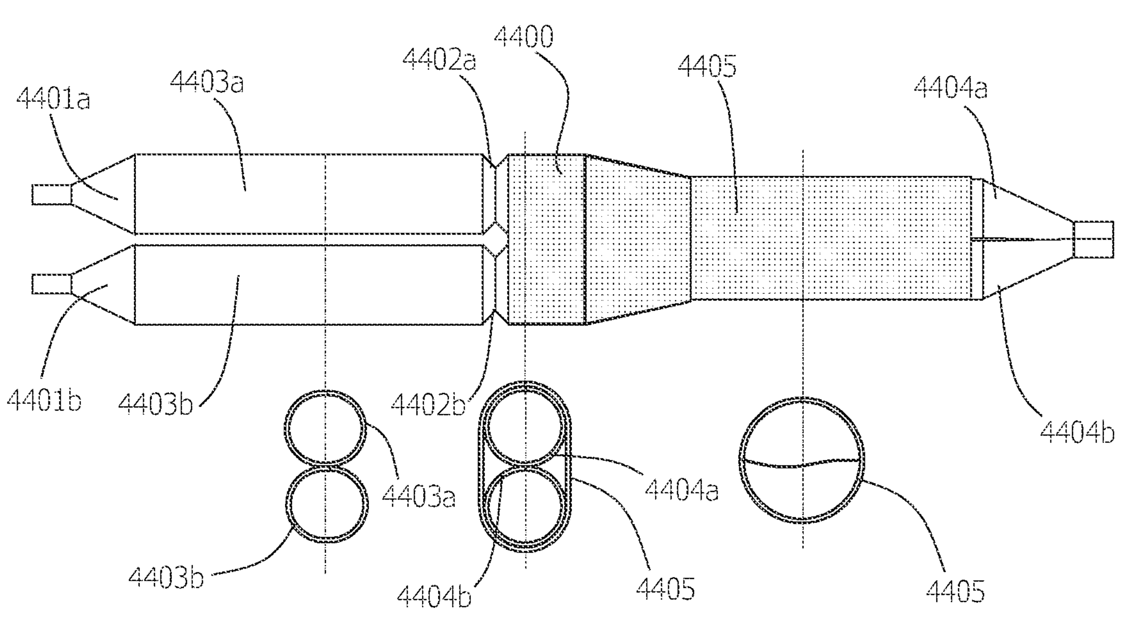
FIG. 44 illustrates another embodiment of a bifurcated balloon assembly.

FIG. 44 illustrates another embodiment of the bifurcated balloon assembly described herein. Bifurcated balloon assembly (4400) comprises cylindrical balloons (4401*a-b*) that are arranged substantially in parallel. Balloons (4401*a-b*) comprise waists (4402*a-b*) that divide balloons (4401*a-b*) into proximal segments (4403*a-b*) and distal segments (4404*a-b*). Restraining sleeve (4405) covers the entire length of distal balloon segments (4404*a-b*). The circumference of the proximal end of restraining sleeve (4405) can match the circumference created by unconstrained distal balloon segments (4404*a-b*), which form a double barrel. The diameter of distal end of restraining sleeve (4405) can be approximately between about 1.22 to about 1.6 times the diameter of distal balloon segments (4404*a-b*) to form an oval cross-section. The diameter of the distal end of restraining sleeve (4405) can be less than about 1.22 times the diameter of the distal balloon segments (4404*a-b*) to form a circular cross-section.

Figure 45:
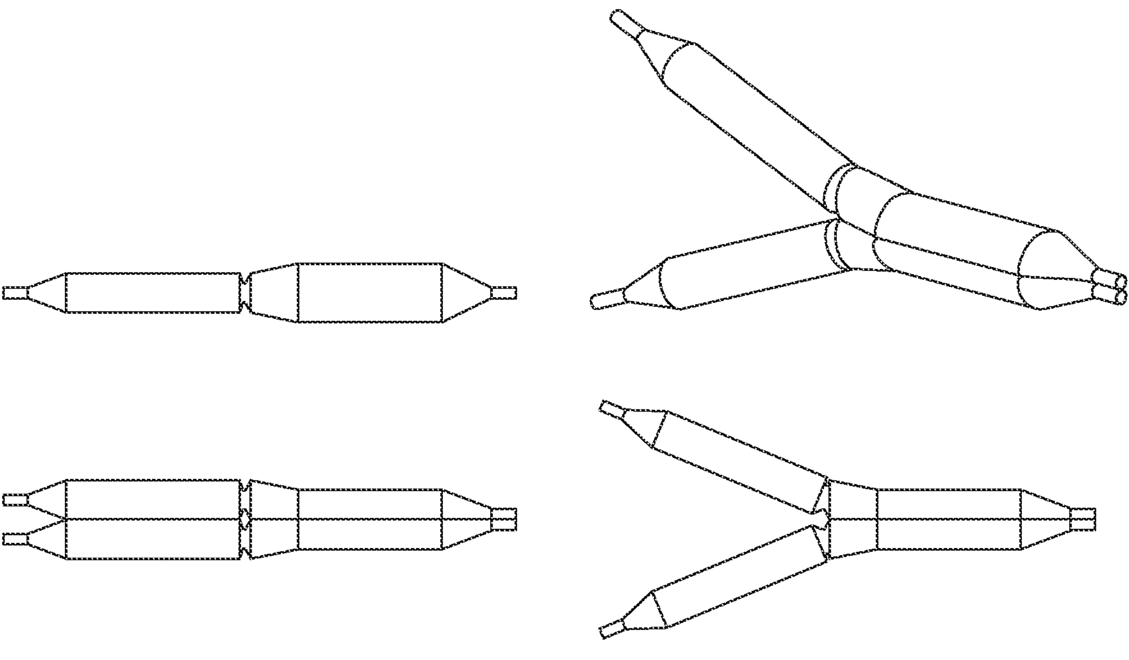
FIG. 45 illustrates perspective views of another embodiment of a bifurcated balloon assembly.
Figure 46:
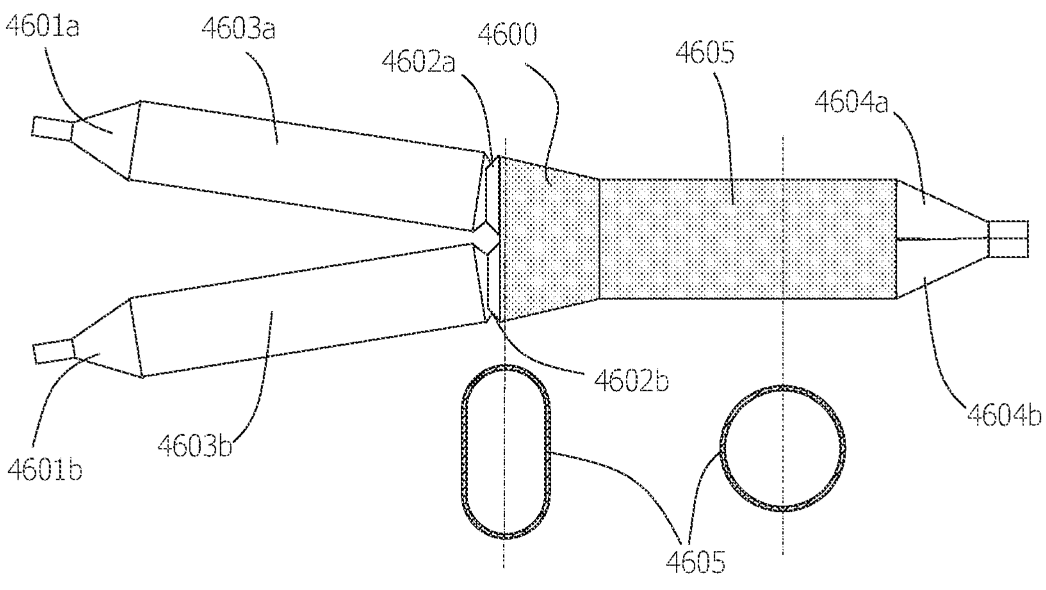
FIG. 46 illustrates a restraining sleeve placed on the bifurcated balloon assembly of FIG. 45.

FIGS. 45-46 illustrate another embodiment of the bifurcated balloon assembly. The balloons can have an asymmetric design that anticipates the desired inflated shape of the balloons in the bifurcated balloon assembly. The proximal balloons segments are axisymmetric and cylindrical in shape. The distal balloon segment features half-moon shaped cross-sections. FIG. 45 shows perspective views of the two balloons illustrating the bifurcated flow channel that is created by the balloon assembly during angioplasty or stenting. FIG. 46 shows a schematic of another embodiment of bifurcated balloon assembly (4600) comprising asymmetric balloons (4601*a-b*) with waists (4602*a-b*) separating proximal segments (4603*a-b*) and distal segments (4604*a-b*). Restraining sleeve (4605) covers distal balloon segments (4602*a-b*). The local circumference of the restraining sleeve can vary from the proximal end to the distal end to match the local circumference of the pair of asymmetric distal balloon segments (4604*a-b*). FIGS. 45-46 merely illustrate one embodiment of a bifurcated balloon assembly using asymmetric balloon designs. It is understood that a wide range of distal segments of the bifurcated balloon assembly can be created using asymmetric balloon designs and a tubular restraining sleeve. It is further understood that in some embodiments, the proximal and distal balloon segments may not be separated by a waist.

Figure 47:
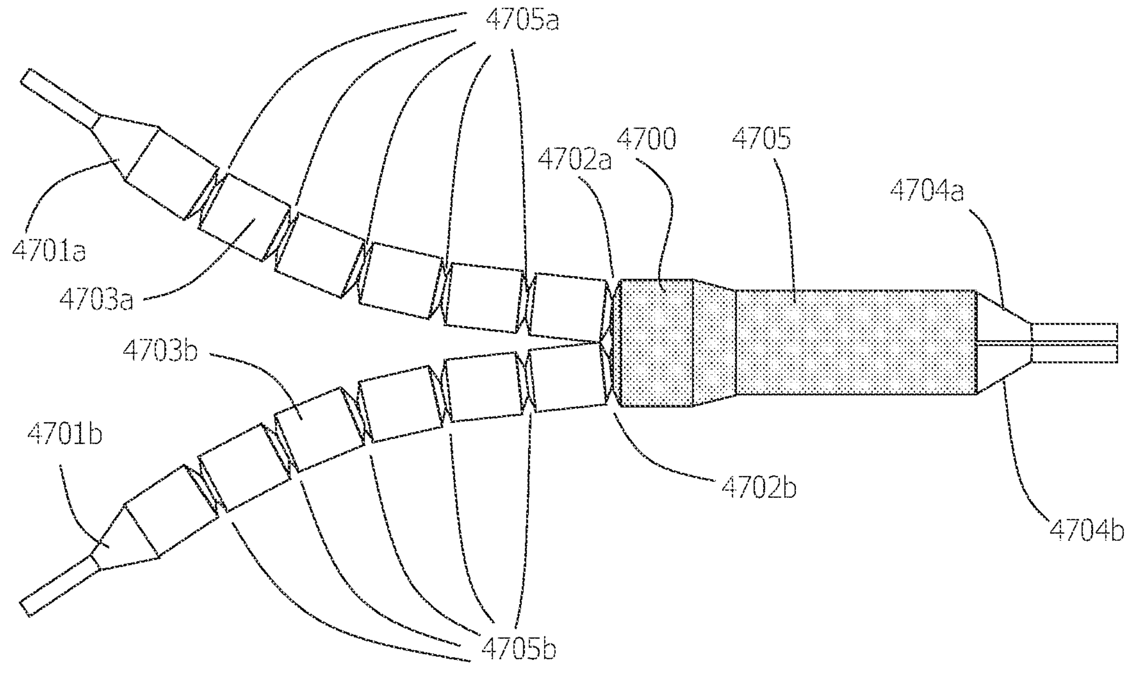
FIG. 47 illustrates another embodiment of a bifurcated balloon assembly with multiple waists in the proximal balloon segments.

FIG. 47 shows another embodiment of the bifurcated balloon assembly. Distal segments (4704*a-b*) and restraining sleeve (4705) of bifurcated balloon assembly (4700) are identical to distal segments (4404*a-b*) and restraining sleeve (4405) of balloon assembly (4400) of FIG. 44. Waists (4702*a-b*) separate proximal segments (4703*a-b*) and distal segments (4704*a-b*) of balloons (4701*a-b*). Proximal balloon segments (4703*a-b*) feature additional waists (4705*a-b*) spaced along the length of proximal balloon segments (4703*a-b*). Additional waists (4705*a-b*) increase the flexibility of proximal balloon segments (4703*a-b*) when balloon assembly (4700) is inflated. The embodiment of FIG. 47 can be considered for the treatment of bifurcated vessels with large take-off angles of the branch vessels from the main vessel or in case of tortuous branch vessels. Waists (4702*a-b*, 4705*a-b*) can cause a local reduction in the expanded vessel diameter in case of balloon angioplasty or can cause localized incomplete stent expansion in case of stenting. To overcome this potential short-coming, balloon assembly (4700) can be inflated in a first position into a bifurcating vessel, deflated and repositioned to move the waists away from the under-expanded vessel or stent sections, and reinflated to fully expand the under-expanded vessel or stent. The incorporation of a waist is not limited to bifurcated balloon assemblies. A balloon with one or more waists can also be incorporated into a single lumen angioplasty balloon catheter or a balloon catheter for the deployment of balloon-expandable single-lumen stents.

Figure 48:
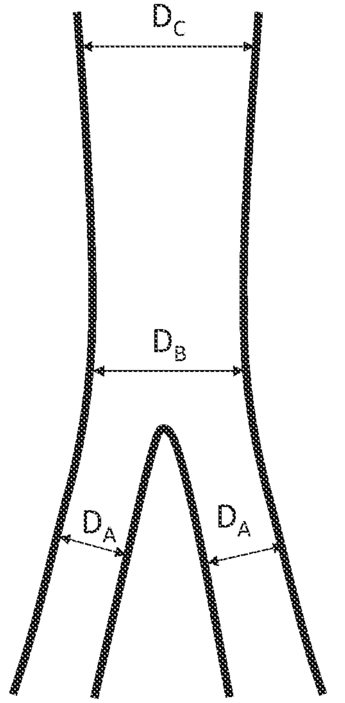
FIG. 48 shows exemplary dimensions of the human aortic bifurcation.
Figure 49:
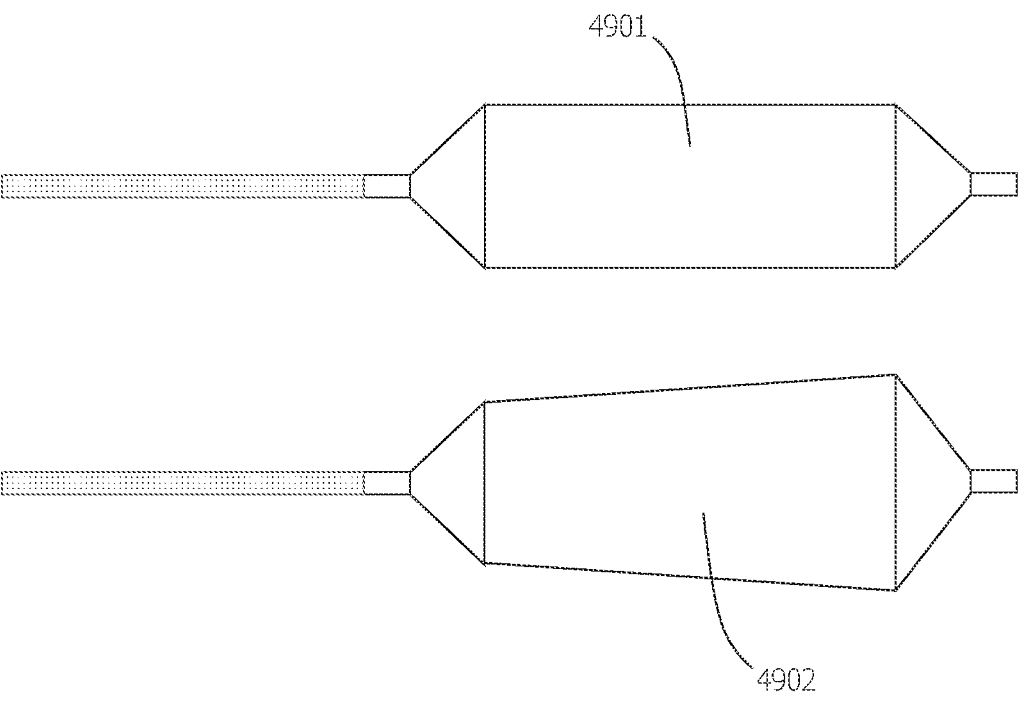
FIG. 49 illustrates example embodiments of a balloon catheter for expansion of the main body stent.

In another embodiment, a method of deploying a bifurcated stent into the aortic bifurcation is described. FIG. 48 illustrates the aortic bifurcation and provides exemplary diameters (DA) of the iliac arteries, exemplary diameters (Os) of the aorta close to the bifurcation, and exemplary diameters (De) of the aorta at the mid-level between the aortic bifurcation and the renal arteries, where the distal end of the bifurcated main body can be placed. Ideally, a bifurcated stent deployed in the aortic bifurcation should achieve wall opposition along its entire length. In the case of a balloon-expandable bifurcated stent, the diameter of the stent is determined by the diameter of the inflating balloon(s). Thus, a bifurcated balloon assembly that conforms to the respective dimensions DA, Ds, and De of the aortic bifurcation can be desirable. In some embodiments, it requires a large number of bifurcated balloon assembly sizes to treat all possible anatomies since the dimensions DA, Ds, and De can vary greatly among patients. To overcome the sizing constraints, a method of expanding a bifurcated stent into the aortic bifurcation using at least two expansion steps is described. In a first step, the bifurcated stent can be expanded by an embodiment of the bifurcated balloon assembly described in FIGS. 41, 43, 44, 45, 46, and 47. In a second step, the midsection and distal end of the main body of the bifurcated stent can be further expanded by a single balloon with a circular cross-section. Exemplary embodiments (4901, 4902) of a balloon catheter with a single circular cross-section are shown in FIG. 49. The balloon can have a constant diameter (4901) or can be tapered (4902) to anticipate the tapered shape of the infrarenal aorta. Balloons (4901, 4902) can be non-compliant or semi-compliant.

Figure 50A:
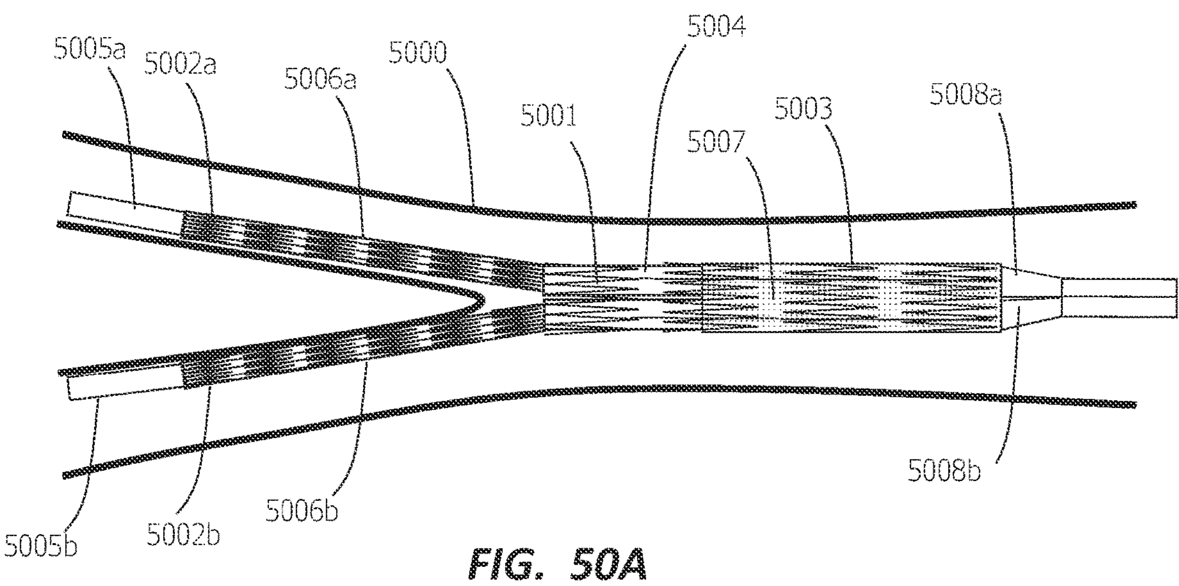
FIG. 50A illustrates a bifurcated stent crimped onto a bifurcated balloon assembly and positioned into an aortic bifurcation.
Figure 50B:
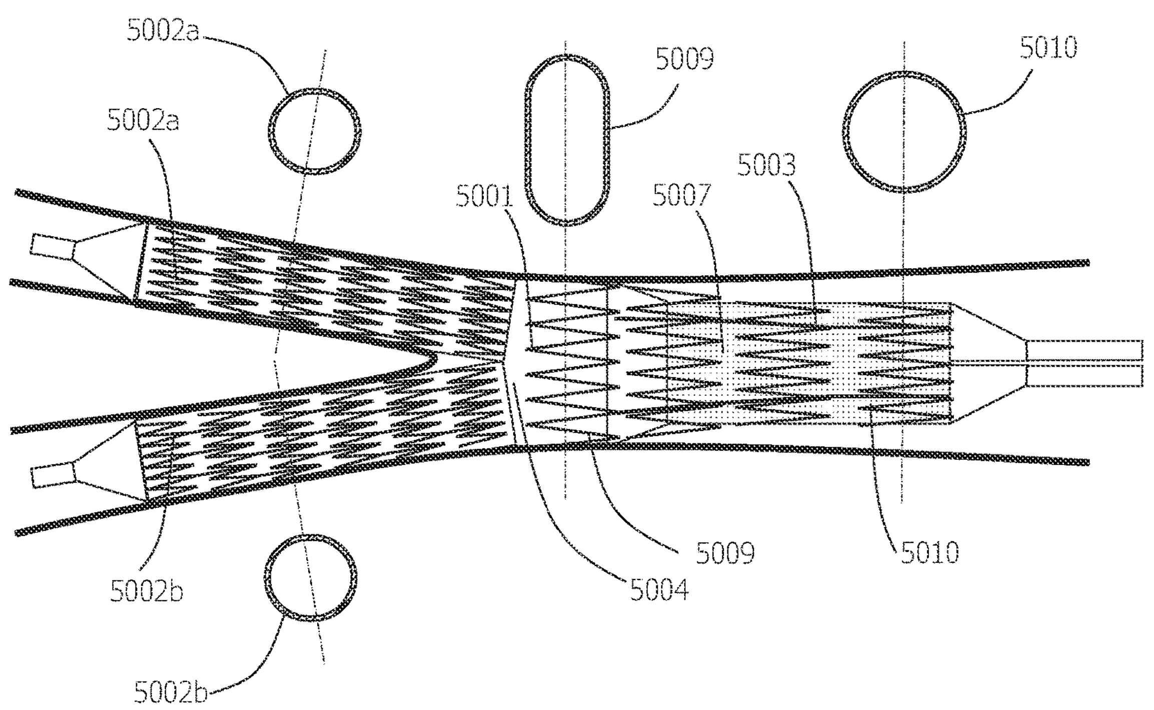
FIG. 50B illustrates the bifurcated balloon assembly of FIG. 50A inflated and the bifurcated stent expanded into a first configuration.
Figure 50C:
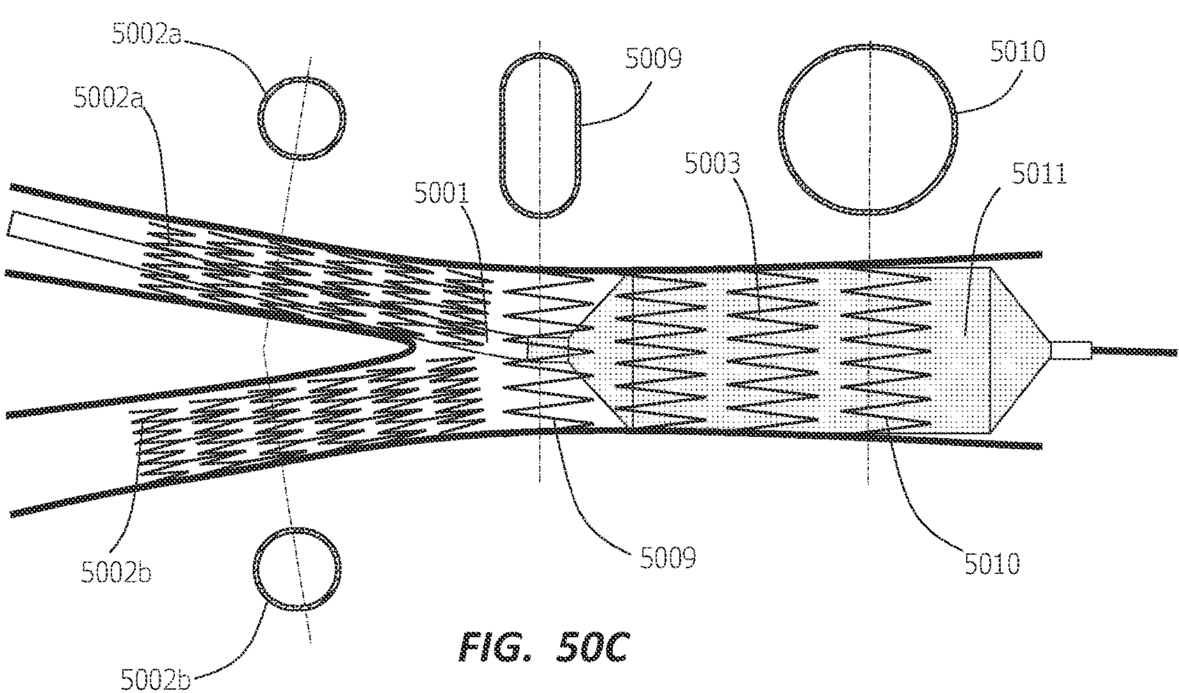
FIG. 50C illustrates the bifurcated balloon assembly of FIG. 50A and the bifurcated stent expanded in a second configuration.

FIGS. 50A-C illustrate the method of deploying a bifurcated stent into the aortic bifurcation using the embodiment of the bifurcated balloon assembly illustrated in FIG. 41 and the balloon catheter illustrated in FIG. 49. FIG. 50A shows bifurcated stent (5001) crimped onto bifurcated balloon assembly (5004) and positioned into aortic bifurcation (5000). Bifurcated stent (5001) comprises branch stents (5002*a*-*b*) and main body stent (5003). First branch stent (5002*a*) is crimped onto proximal segment (5006*a*) of first balloon (5005*a*), and second branch stent (5002*b*) is crimped onto proximal segment (5006*b*) of second balloon (5005*b*). Main body stent (5003) is crimped onto restraining sleeve (5007) and distal balloon segments (5008*a*-*b*). FIG. 50B shows bifurcated balloon assembly (5004) inflated and bifurcated stent (5001) expanded into a first configuration. In the first configuration, branch stents (5002*a*-*b*) are expanded to the iliac artery diameter DA. The proximal end of main body stent (5009) is expanded to an oval cross-section that provides a smooth flow transition into branch stents (5002*a*-*b*). Midsection and distal end (5010) of main body stent (5003) which are covered by restraining sleeve (5007) are inflated to the diameter of restraining sleeve (5007), which can be less or equal to the diameter of the aorta Ds and De. FIG. 50C illustrates the second deployment step. Circular balloon (5011) is inflated inside main body stent (5003) to expand mid-section and distal end (5010) of main body stent (5003) in order to achieve wall apposition of main body stent (5003) in the infrarenal aorta. In the second configuration, branch stents (5002*a*-*b*) are expanded to the iliac artery diameter DA, the proximal end of main body stent (5009) is expanded into an oval shape, and mid-section and distal end (5010) of main body stent (5003) are expanded to the respective diameters Ds and De of the infrarenal aorta. It is understood that the disclosed method of deploying a bifurcated stent can include additional steps. For example, additional balloon expansion steps can be performed to conform the branch stents and main body stent to the anatomy of the iliac artery and aorta respectively or to increase the stented vessel diameters. In some embodiments, the method of deploying a bifurcated stent does not include all the above steps.

Figure 51:
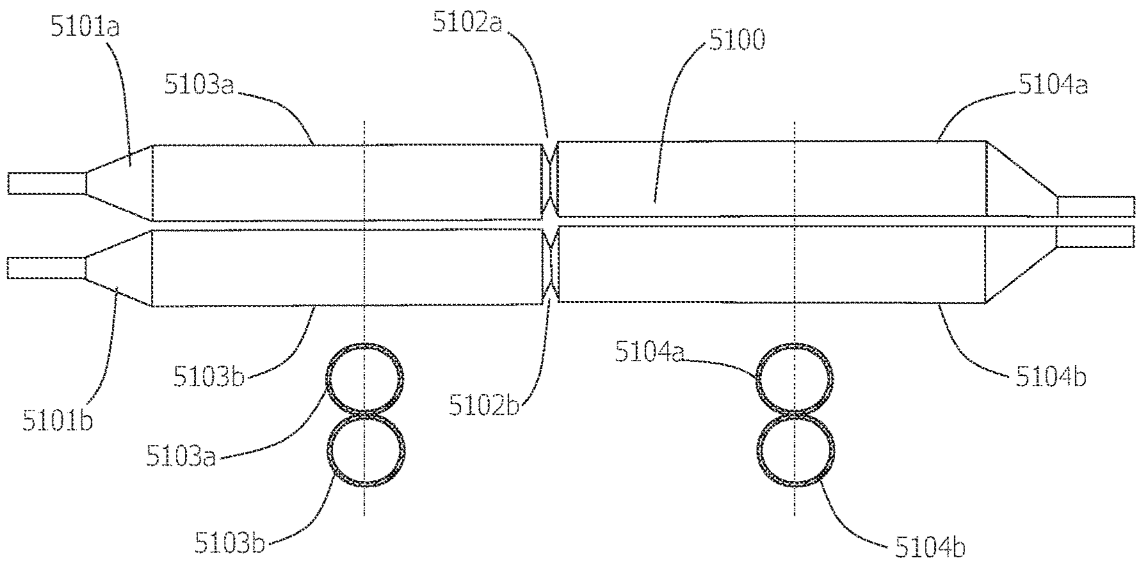
FIG. 51 illustrates an example embodiment of a bifurcated balloon assembly without a restraining sleeve.

In another embodiment, the deployment method comprises at least two steps, an another embodiment of the bifurcated balloon assembly is described herein. Since a circular cross-section of the main body stent does not have to be achieved in the first deployment step, a bifurcated balloon assembly without a restraining sleeve as shown in FIG. 51 can be considered for the first deployment step. Bifurcated balloon assembly (5100) comprises cylindrical balloons (5101*a*-*b*) that are arranged substantially in parallel. In some embodiments, balloons (5101*a*-*b*) can further comprise waists (5102*a*-*b*) that divide balloon (5101*a*-) into proximal balloon segments (5103*a*-*b*) and distal balloon segments (5104*a*-*b*). Distal balloon segments (5104*a*-*b*) are unconstrained and together form a double-barrel cross-section. Distal balloon segments (5104*a*-*b*) expand the main body stent into an oval cross-section. In the second deployment step, a cylindrical balloon as shown in FIG. 49 can be used to further expand the mid-section and distal end of the main body to its final circular cross-section.

Figure 52:
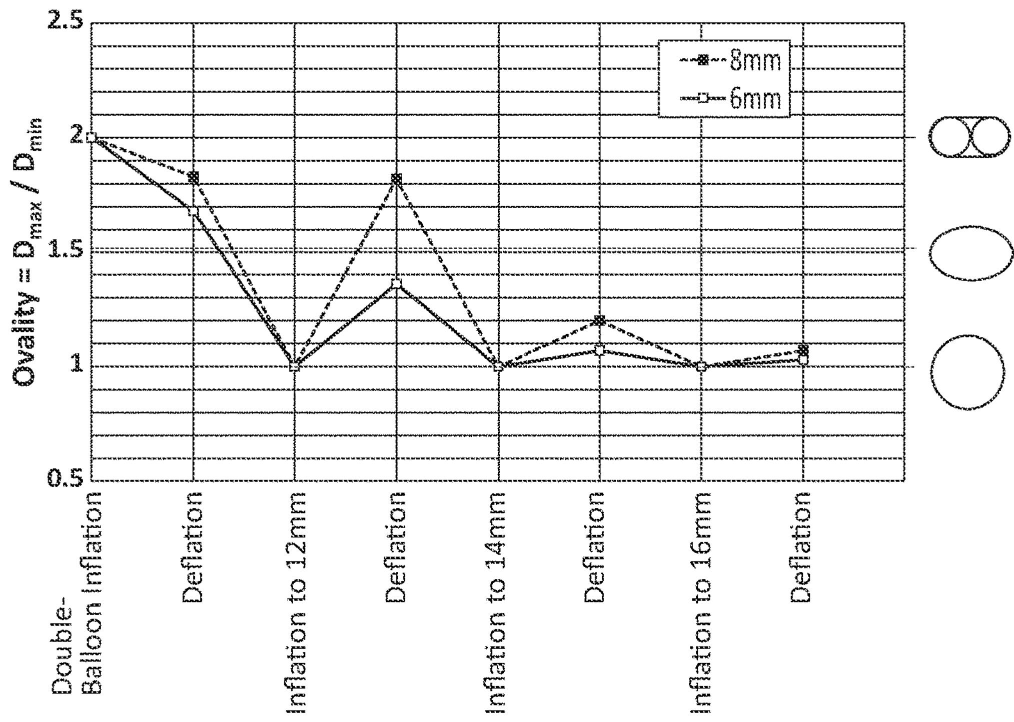
FIG. 52 shows the results of computer simulations of deploying the main body stent in two steps.

FIG. 52 displays graphically the results of a computational analysis of a main body stent made from stainless steel and expanded by a bifurcated balloon assembly comprising two parallel unconstrained balloons. The ovality of the cross-sectional area of the main body stent that is created during the deployment sequence is expressed as the largest diameter of the stent divided by the smallest diameter. For example, the ovality of a circular stent is 1. The ovality of an elliptical stent having a main axis length of 20 mm and a minor axis length of 10 mm is 2. In the first computer simulation, expansion of the main body stent by two parallel balloons of diameters of 8 mm (Step 1) followed by subsequent balloon expansion with a 12 mm, 14 mm, and 16 mm diameter single balloon (Step 2) is modelled. The black dots connected by the dotted line in the graph in FIG. 52 display the values of the ovality of the main body stent as it undergoes the deployment sequence. The two balloons expand the main body stent into an oval with an ovality of (2×8 mm)/8 mm=2. When the balloons are deflated, the main body stent slightly recoils into a more circular shape. The ovality of the recoiled stent is 1.82. In the next step, the main body stent is expanded by a cylindrical balloon of diameter of about 12 mm in accordance with the proposed two-step deployment method. When the cylindrical balloon is deflated, the stent does not maintain its circular shape but recoils back to an ovality close to 1.8. This is due to the fact that the two 8 mm diameter balloons expand the main body stent to a circumference of about 41 mm. Subsequent balloon expansion of the main body stent with the circular 12 mm balloon, which has a circumference of 37 mm, does not further expand the main body stent.

The main body stent mainly undergoes elastic deformations to accommodate the circular shape of the inflated 12 mm balloon and recoils back to its original oval shape when the balloon is deflated. Expanding the main body stent further to 14 mm and 16 mm as shown in the graph in FIG. 52 causes further expansion of the main body stent and introduces sufficient plastic deformations in the stent material to create a permanent shape change toward a more circular cross-section. FIG. 52 also displays the results of a computer simulation using two balloons of diameters of about 6 mm for the first deployment step as indicated by the open circles connected by a continuous line. The circumference of the oval created by the two 6 mm balloons is 31 mm, which is less than that the 39 m circumference of the 12 mm balloon. Expanding the main body stent with the two 6 mm diameter balloons in a first step and a 12 mm cylindrical balloon in a second step yields an ovality of 1.36. The ovality is further reduced with subsequent stent expansions using balloons of diameters 14 mm and 16 mm. Based on the results of the two computer simulations, it can be advantageous to under-expand the main body stent in the first deployment step to a circumference of less than π×Ds (=3.1418 Ds) and less than π×De (=3.1418 De). At the same time, the main body stent is expanded sufficiently in the first step to safely remove the balloon catheter through the bifurcated stent. Potential migration of the under-expanded bifurcated stent is not a concern since the bifurcated stent is sitting on the bifurcation with the branch stents fully expanded.

Figure 53:
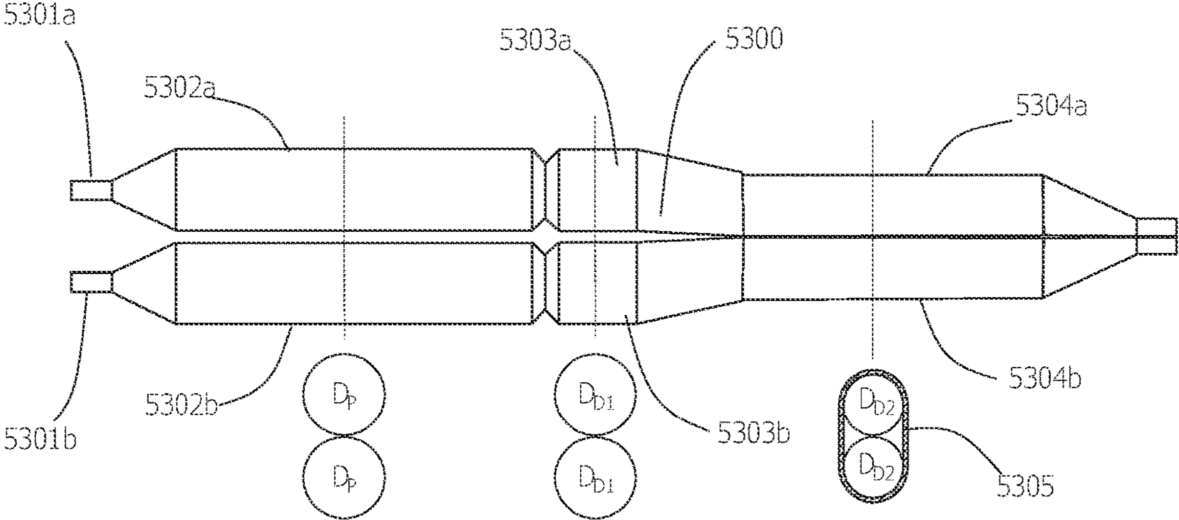
FIG. 53 illustrates another embodiment of a bifurcated balloon assembly without a restraining sleeve.
Figures 54, 55A:
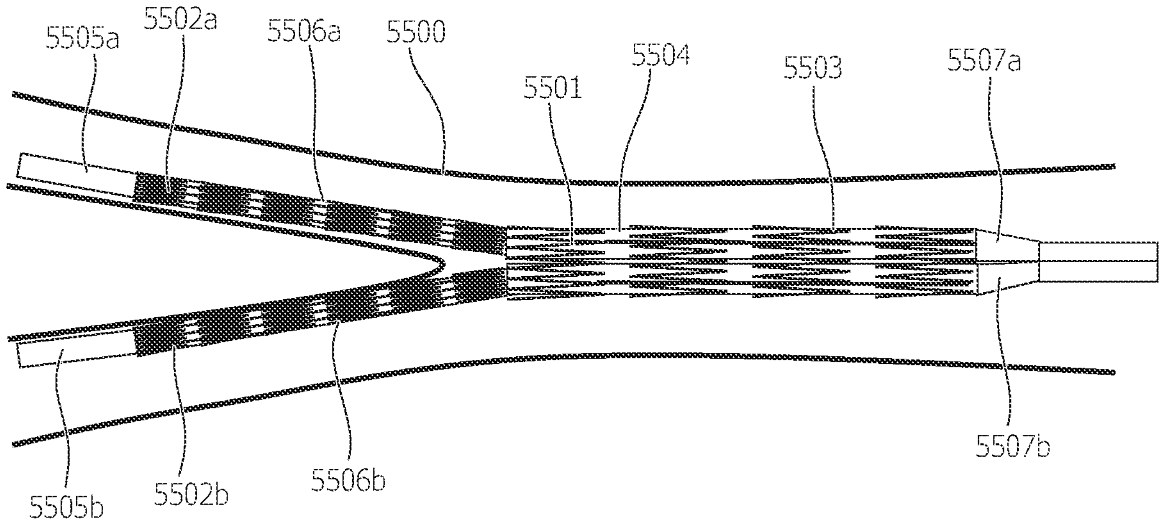
FIG. 54 shows exemplary diameters of the bifurcated balloon assembly without a sleeve.
FIG. 55A illustrates a bifurcated stent crimped onto a bifurcated balloon assembly and positioned into an aortic bifurcation.

FIG. 53 shows an example of bifurcated balloon assembly (5300) without a restraining sleeve designed for a two-step deployment of a bifurcated stent into the aortic bifurcation. Bifurcated balloon assembly (5300) comprises cylindrical balloons (5301*a-b*) arranged substantially in parallel. The proximal ends of distal balloon segments (5303*a-b*) and proximal balloon segments (5302*a-b*) have approximately the same diameter to minimize flow disturbances at the transition from the main body stent to the branch stents. The mid-section and distal ends of distal balloon segments (5304*a-b*) have a reduced diameter compared to proximal ends (5303*a-b*). Circumference (5305) of distal balloons segments (5304*a-b*) is less than the circumference of the aortic flow lumen. FIG. 54 provides exemplary dimensions of the balloon assembly of FIG. 53. It is understood that the balloons can take on any diameter within the listed range of diameters. It is further understood, the balloon dimensions are not limited to the diameters listed in FIG. 54.

Figure 55B:
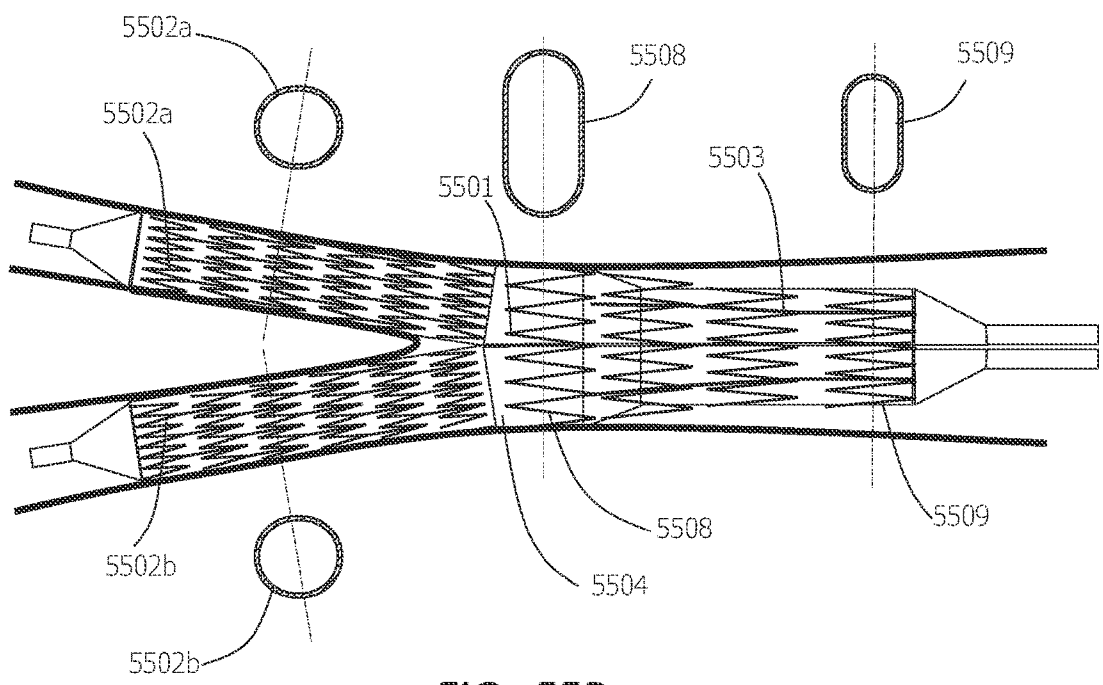
FIG. 55B illustrates the bifurcated balloon assembly of FIG. 55A inflated and the bifurcated stent expanded into a first configuration.
Figure 55C:
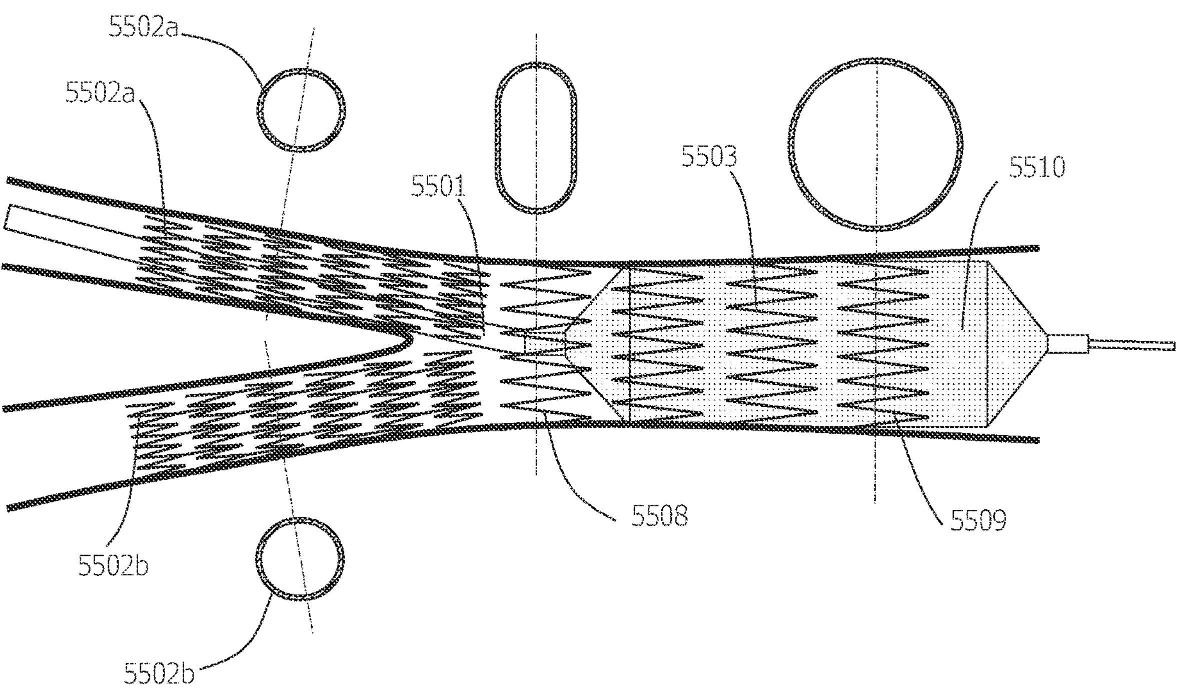
FIG. 55C illustrates the bifurcated balloon assembly of FIG. 55A inflated and the bifurcated stent expanded into a second configuration.

FIGS. 55A-C illustrate the method of deploying a bifurcated stent into the aortic bifurcation using the embodiment of the bifurcated balloon assembly from FIG. 53. FIG. 55A shows bifurcated stent (5501) crimped onto bifurcated balloon assembly (5504) and positioned into aortic bifurcation (5500). Bifurcated stent (5501) comprises branch stents (5502*a-b*) and main body stent (5503). First branch stent (5502*a*) is crimped onto proximal segment (5506*a*) of first balloon (5505*a*), and second branch stent (5502*b*) is crimped onto proximal segment (5506*b*) of second balloon (5505*b*). Main body stent (5503) is crimped onto distal balloon segments (5507*a-b*). FIG. 55B shows bifurcated balloon assembly (5504) inflated and bifurcated stent (5501) expanded into a first configuration. In the first configuration, branch stents (5502*a-b*) are expanded to the iliac artery diameter DA. The proximal end of main body stent (5508) is expanded to an oval shape of a first circumference that provides a smooth flow transition into branch stents (5502*a-b*). The midsection and distal end (5509) of main body stent (5503) is inflated to an oval of a second circumference. The second circumference is smaller than the first circumference and smaller than the circumference of the aorta. FIG. 55C illustrates the second deployment step. Circular balloon (5510) is inflated inside main body stent (5503) to expand mid-section and distal end (5509) of main body stent (5503) into a second configuration to achieve wall apposition in the infrarenal aorta. In the second configuration, branch stents (5502*a-b*) are expanded to the iliac artery diameter DA, proximal end (5508) of main body stent (5503) is expanded into an oval shape, and mid-section and distal end (5509) of main body stent (5503) is expanded to the respective diameters Ds and De of the infrarenal aorta. In some embodiments, the main body stent does not take on a perfect circular shape after the second deployment step. As illustrated in FIG. 52, expansion of main body stent (5503) reduces the ovality of mid-section and distal end (5509) of main body stent (5503), but main body stent (5503) does not reach an ovality of 1. In some embodiments, the main body stent does reach an ovality of 1. Although distal end (5509) of main body stent (5503) can be oval after completion of the second deployment step, distal end (5509) of main body stent (5503) has a smaller ovality than after the first deployment step. The ovality of the distal end (5509) of main body stent (5503) can be between about 1.5 and about 2.0 after the first deployment step and between about 1.0 and about 1.5 after the second deployment step. After completion of the second deployment step, the distal end (5509) of main body stent (5503) can have a smaller ovality than proximal end (5508). It is further understood that the disclosed method of deploying a bifurcated stent can include additional steps. For example, additional post-ballooning can be performed to conform the branch stents and main body stent to the anatomy of the iliac artery and aorta respectively or to increase the stented vessel diameters.

The embodiments of the bifurcated balloon assemblies described in FIGS. 8, 9, 32, 33, 35, 36, 37, 38, 39, 41, 43, 44, 45, 46, 47, 51, and 53 are exemplary embodiments of the bifurcated balloon assemblies described herein. It is understood that the proximal and distal balloon segments can be of different diameters and that the diameters of the individual sections can vary along their respective length. It is further understood that in some embodiments the proximal and distal balloon segments are not separated by a waist. The restraining sleeve can fully or only partially cover the distal balloon segments. The restraining sleeve can vary in diameter along its length. The sleeve can have sections that restrain the expansion of the distal balloon segments and sections that do not restrain the expansion of the distal balloon segments. In some embodiments, the bifurcated balloon assembly does not comprise a restraining sleeve. The aortic bifurcation is used as an example of a branching or bifurcated vessel in the body that can be treated with a bifurcated balloon assembly described herein. It is understood that the bifurcated balloon assemblies can also be used to treat any other branch point or bifurcation in the body including, but not limited to, arterial bifurcations, venous bifurcations, and bifurcations of the airways. This can also include asymmetric bifurcations. Examples of asymmetric bifurcations are the iliac artery bifurcations, carotid artery bifurcations, and coronary artery bifurcations. For the treatment of asymmetric bifurcations, the bifurcated balloon assembly can feature an asymmetric design. The first proximal balloon segment can differ in diameter, length, and shape from the second proximal balloon segment. The first distal balloon segment can differ in diameter, length, and shape from the second distal balloon segment.

Figure 56:
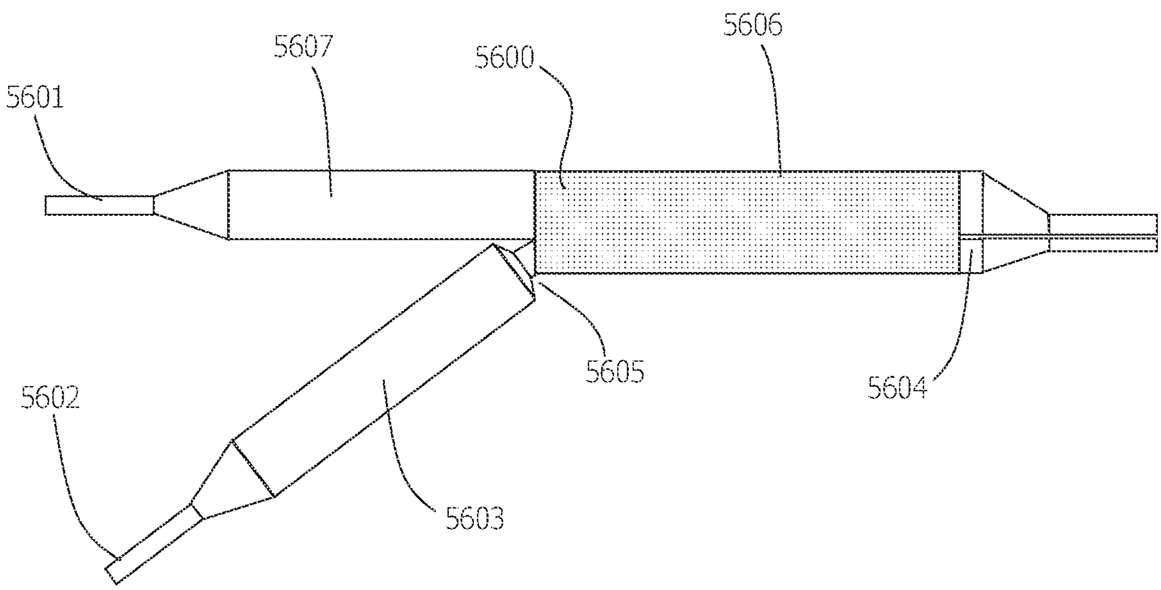
FIG. 56 illustrates an asymmetric embodiment of the bifurcated balloon assembly.

In some embodiments, a waist only separates the distal and proximal balloon segments of one balloon. The restraining sleeve can be asymmetric in shape. If the bifurcated balloon assembly is placed into a bifurcated vessel from the main vessel, the term "proximal" can refer to the direction toward the two branching vessels and the term "distal" can refer to the direction toward the main vessel. FIG. 56 illustrates an asymmetric embodiment of bifurcated balloon assembly (5600). This embodiment can be considered for the treatment of the iliac bifurcation where the common iliac artery branches into the external and internal iliac artery. Bifurcated balloon assembly (5600) comprises balloons (5601, 5602) and restraining sleeve (5606). First balloon (5601) is constant in diameter and does not have a waist. Second balloon (5602) comprises of proximal segment (5603) of a first diameter, distal segment (5604) of a second diameter that is less than the first diameter, and waist (5605). In some embodiments, proximal segment (5603) can be placed into the internal iliac artery, unrestrained section (5607) of first balloon (5601) can be placed into the external iliac artery, and restrained sections (5606) of balloons (5601, 5602) can be placed into the common iliacartery.

Figure 57A:
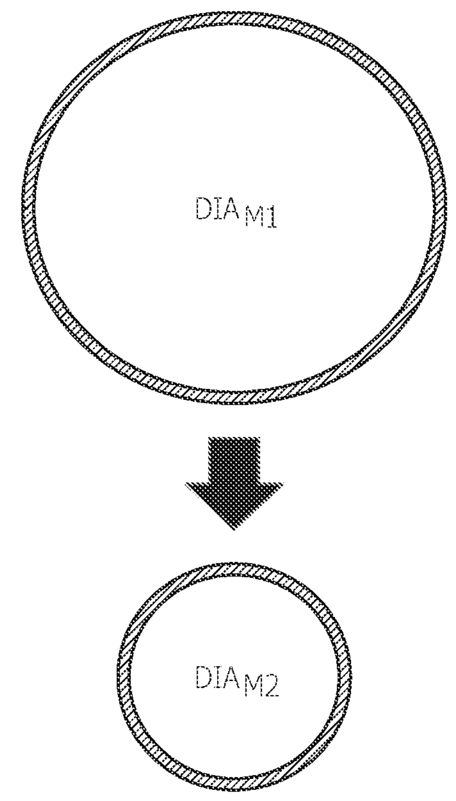
FIG. 57A illustrates a first step of crimping a main body of a bifurcated stent onto a bifurcated balloon assembly.
Figure 57B:
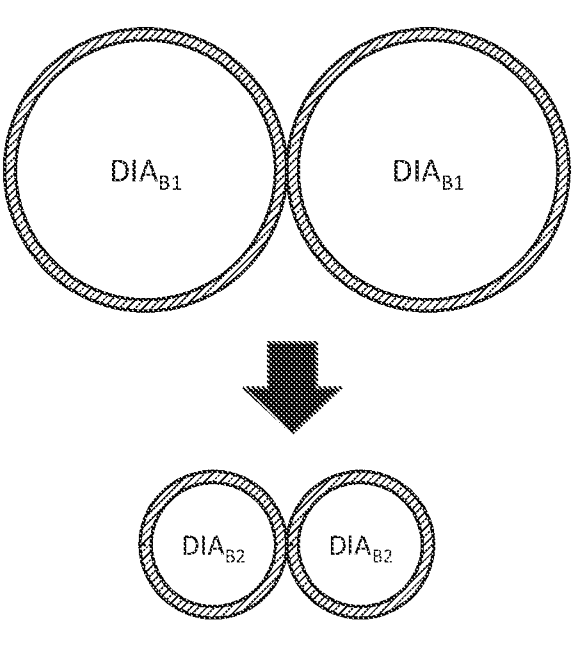
FIG. 57B illustrates a first step of crimping branch stents of the bifurcated stent of FIG. 57A onto the bifurcated balloon assembly.
Figure 58A:
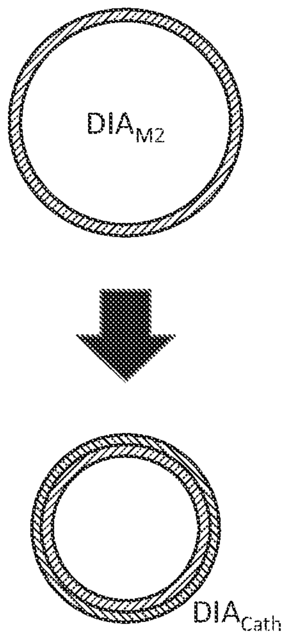
FIG. 58A illustrates a second step of crimping the main body of a bifurcated stent of FIG. 57A onto the bifurcated balloon assembly.
Figure 58B:
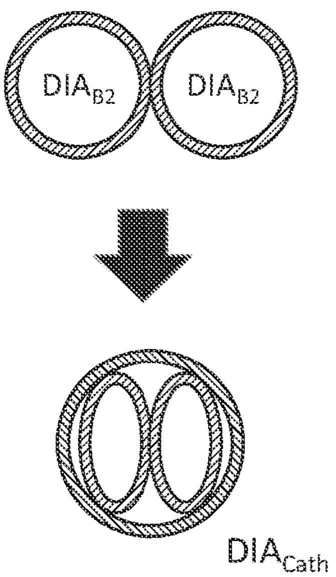
FIG. 58B illustrates a second step of crimping branch stents of the bifurcated stent of FIG. 58B onto the bifurcated balloon assembly.

In other embodiments, methods of crimping a bifurcated stent onto a bifurcated balloon assembly are described. In some embodiments, the objective of the crimping process described herein is to compress the bifurcated stent to a diameter that is equal to or smaller than the targeted crossing profile of the stent delivery system. Exemplary embodiments of bifurcated stent delivery systems are shown in FIG. 1 and FIG. 16. FIGS. 57A-B illustrate a first step of crimping a bifurcated stent onto a bifurcated balloon assembly. FIG. 57A shows the cross-section of the main body stent. In the first step of the crimping process, the main body stent is compressed radially inward from a first diameter DIAM1 to a second diameter DIAM2 wherein DIAM2 is smaller than DIAM1. FIG. 57B shows the cross-sections of the branch stents. In the first step of the crimping process, the branch stents are compressed radially inward from a first diameter DIAs1 to a second diameter DIAs2 wherein DIAs2 is smaller than DIAs1. FIGS. 58A-B illustrate a second step of crimping a bifurcated balloon onto a bifurcated balloon assembly. FIG. 58A illustrates the second step of crimping the main body stent. The main body stent is radially compressed from the second diameter DIAM2 to a diameter equal or smaller than the crossing profile diameter DIAcath of the balloon catheter. In the second step of the crimping process, the branch stents are compressed from diameter DIAs2 to an oval shaped cross-section as shown in FIG. 58B. The cross-sections of the oval branch stents are smaller than the cross-sections of the branch stents at a diameter of DIAs2. The two oval-shaped branch stents fit into the desired circular crossing profile of the balloon catheter of diameter DIAcath—The main axis diameter of the branch stent is equal to or less than DIAcath—The minor axis diameter of the branch stent is equal to or less than 0.5× DIAcath—

Figure 59A:
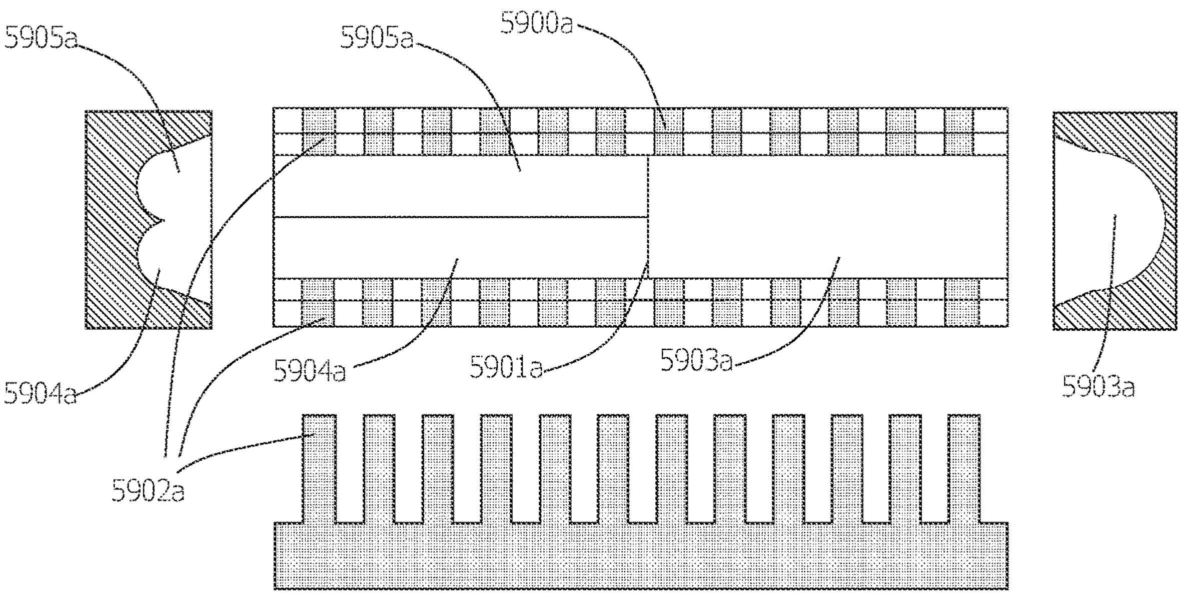
FIG. 59A illustrates part A of an embodiment of a bifurcated crimping tool.
Figure 59B:
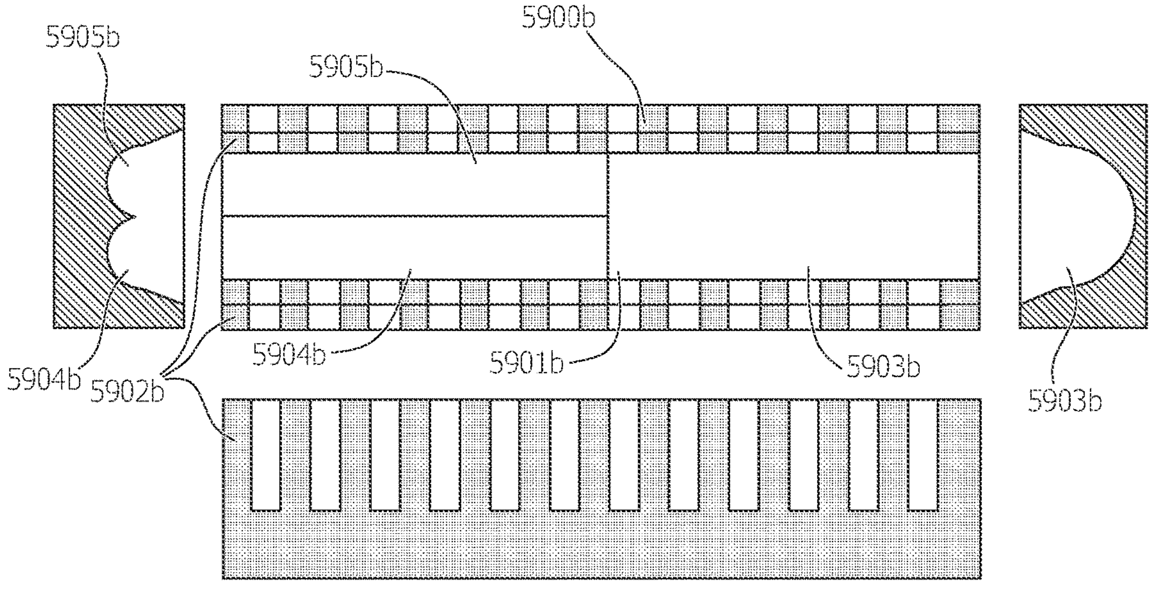
FIG. 59B illustrates part B of an embodiment of a bifurcated crimping tool.
Figure 60:
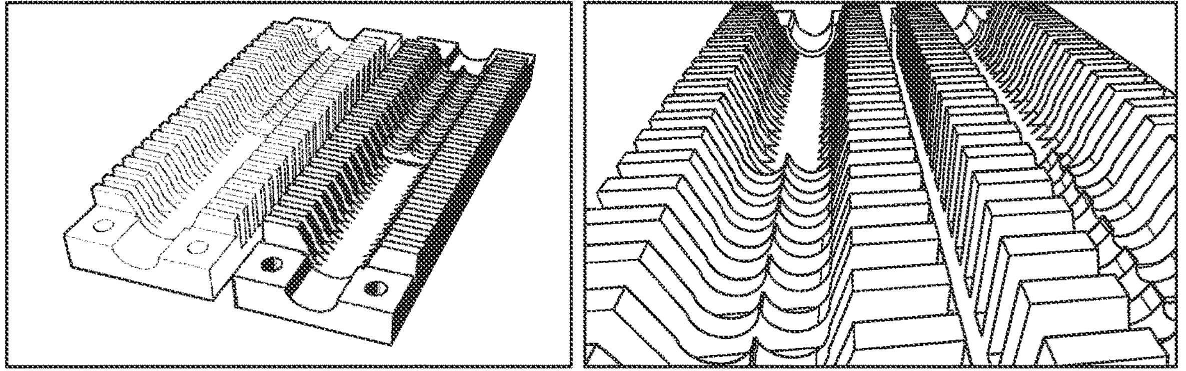
FIG. 60 illustrates perspective views of the bifurcated crimping tool.
Figure 61:
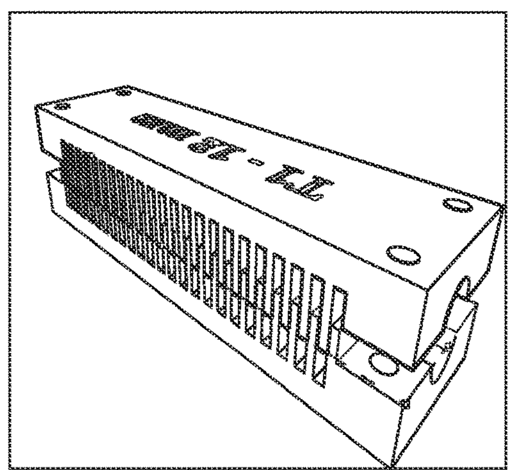
FIG. 61 illustrates the bifurcated crimping tool in an interlaced configuration.
Figure 61:
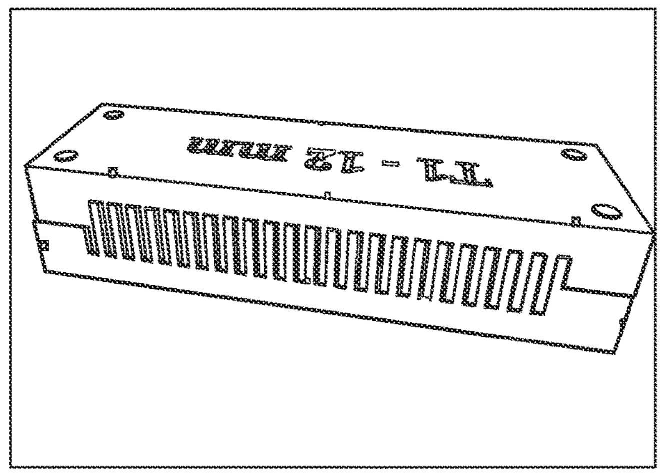
Figure 62A:
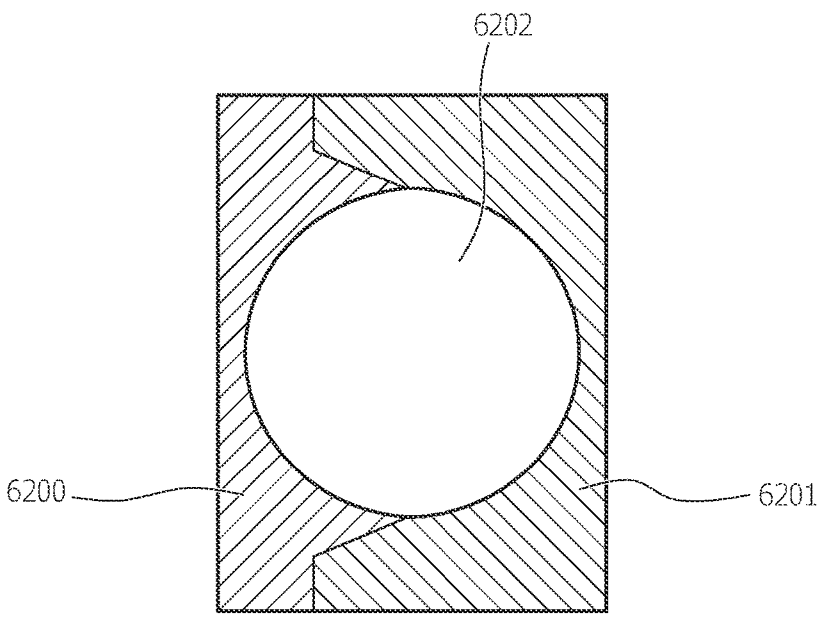
FIG. 62A illustrates a cross-section of the bifurcated crimping tool in an interlaced configuration.
Figure 62B:
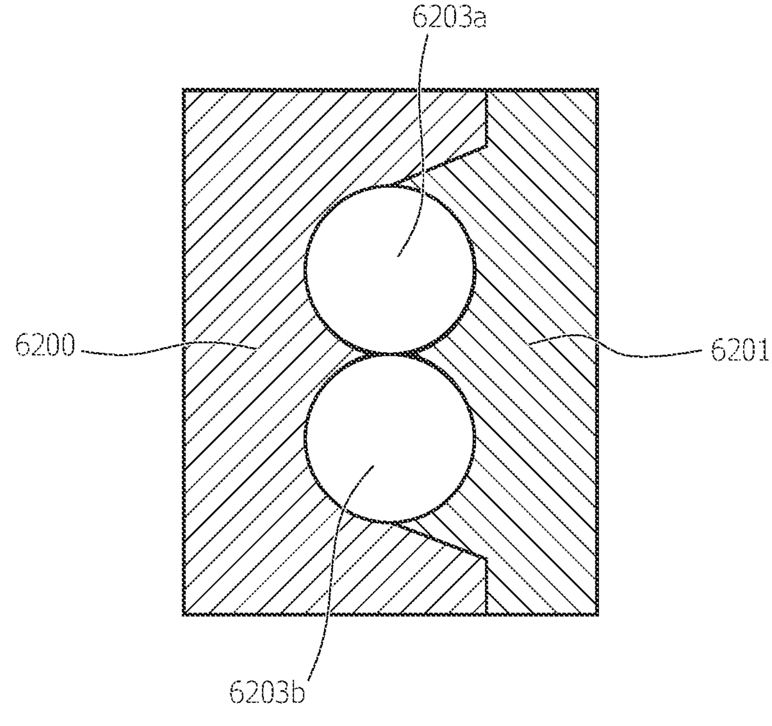
FIG. 62B illustrates a cross section of the bifurcated crimping tool in an interlaced configuration.

FIGS. 59A-B illustrate an embodiment of a crimping tool that can be used to perform the first crimping step. In some embodiments, the crimping tool comprises two interlacing parts, Part A (FIG. 59A) and Part B (FIG. 59B). Parts A and B (5900*a-b*) comprise bifurcated channels (5901*a-b*) arranged parallel to the main axis of parts (5900*a-b*) and a series of ribs (5902*a-b*) arranged perpendicular to the main axis of parts (5900*a-b*). Bifurcated channels (5901*a-b*) comprise of main channels (5903*a-b*) and branch channels (5904*a-b*, 5905*a-b*). The floors of channels (5903*a-b*, 5904*a-b*, 5905*a-b*) are half-circular in shape. Sloped shoulders form a funnel into the half-circular shaped floors. FIG. 60 illustrates perspective views of the two interlacing parts further illustrating the shape of the channels and the ribs. FIG. 61 displays 3-dimensional renderings of the two parts of the crimping tool interlaced with each other. FIGS. 62A-B show cross-sections of the interlaced Parts A and B of the crimping tool. The opposing half-circular channels of Part A and Part B form circular lumens. FIG. 62A shows lumen (6202) formed by the two main channels of interlaced Part A (6200) and Part B (6201). FIG. 62B shows parallel lumens (6203*a-b*) formed by the branch channels of interlaced Part A (6200) and Part B (6201).

Figure 63A:
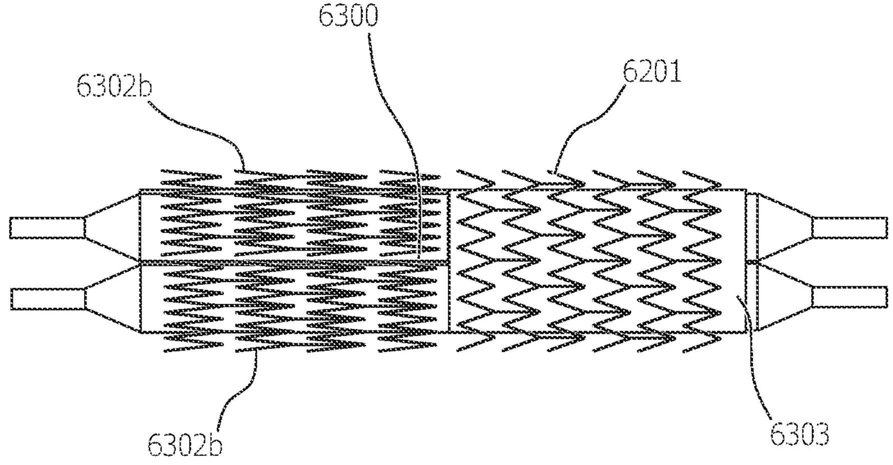
FIG. 63A illustrates an uncrimped bifurcated stent placed onto a bifurcated balloon assembly.
Figure 63B:
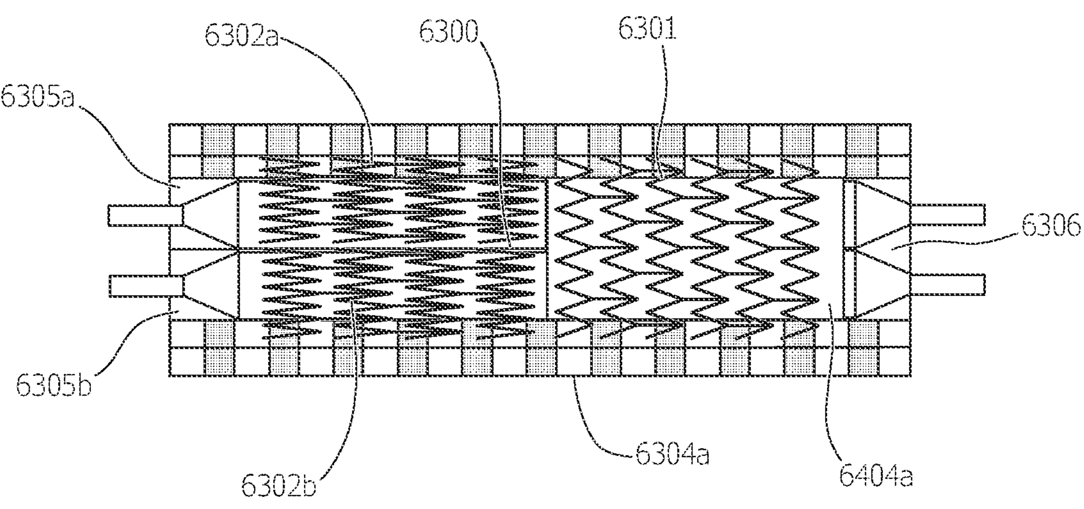
FIG. 63B illustrates the bifurcated stent and the bifurcated balloon assembly of FIG. 63A placed onto part A of the bifurcated crimping tool.
Figure 64A:
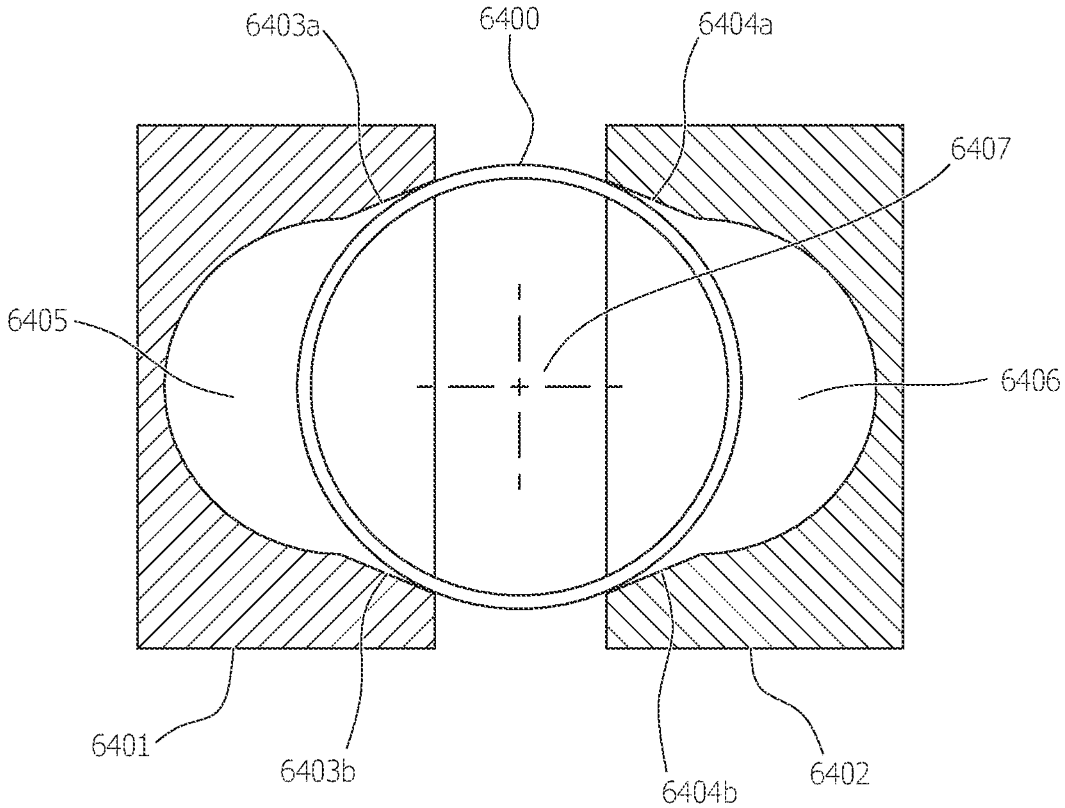
FIG. 64A illustrates crimping a main body of a bifurcated stent.
Figure 64B:
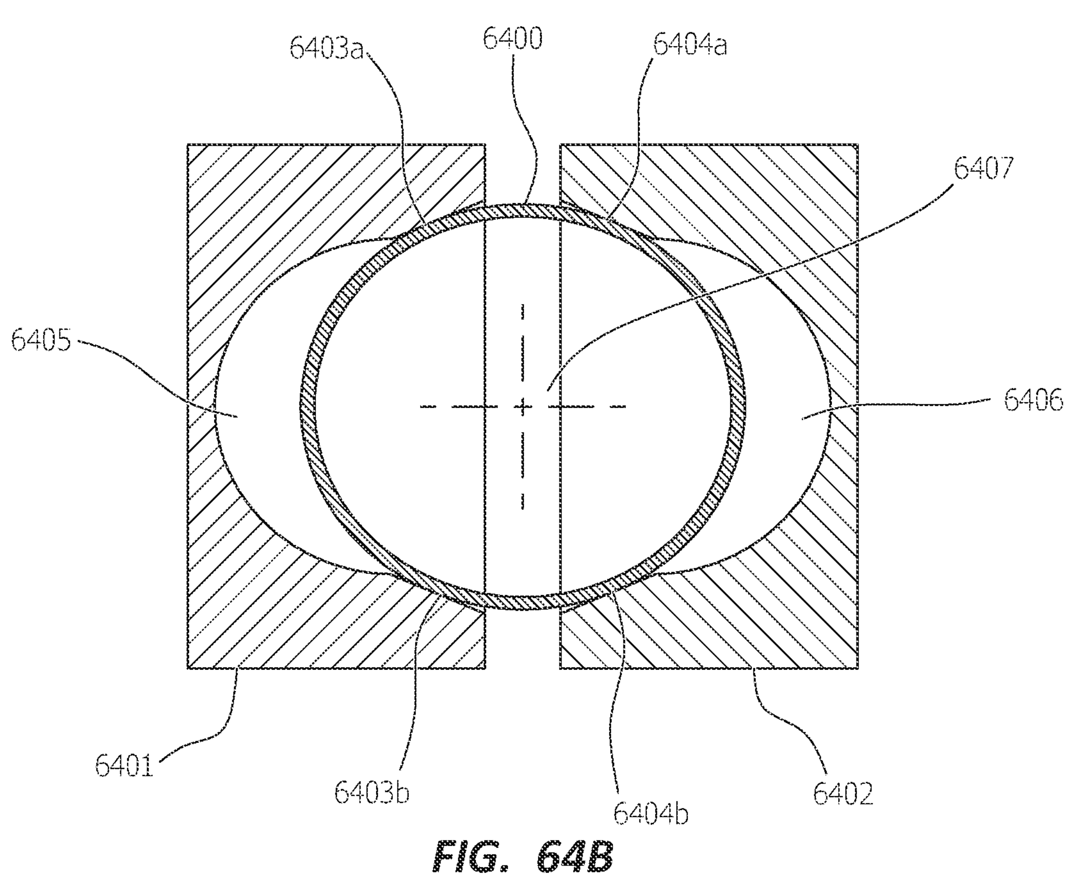
FIG. 64B illustrates further crimping the main body of the bifurcated stent of FIG. 64A.
Figure 64C:
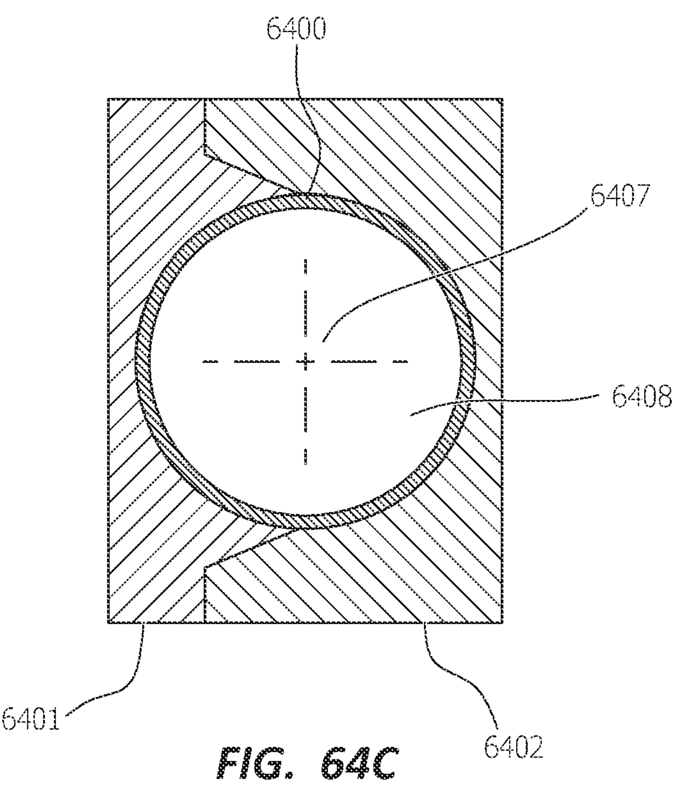
FIG. 64C illustrates further crimping the main body of the bifurcated stent of FIG. 64A.
Figure 65A:
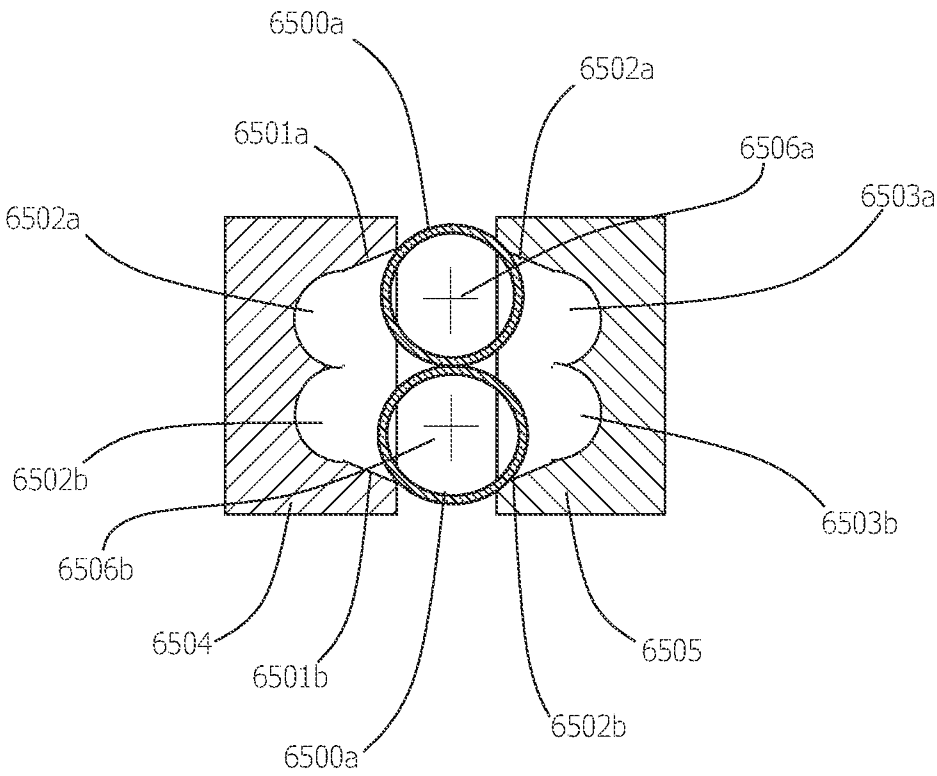
FIG. 65A illustrates crimping branches of a bifurcated stent.
Figure 65B:
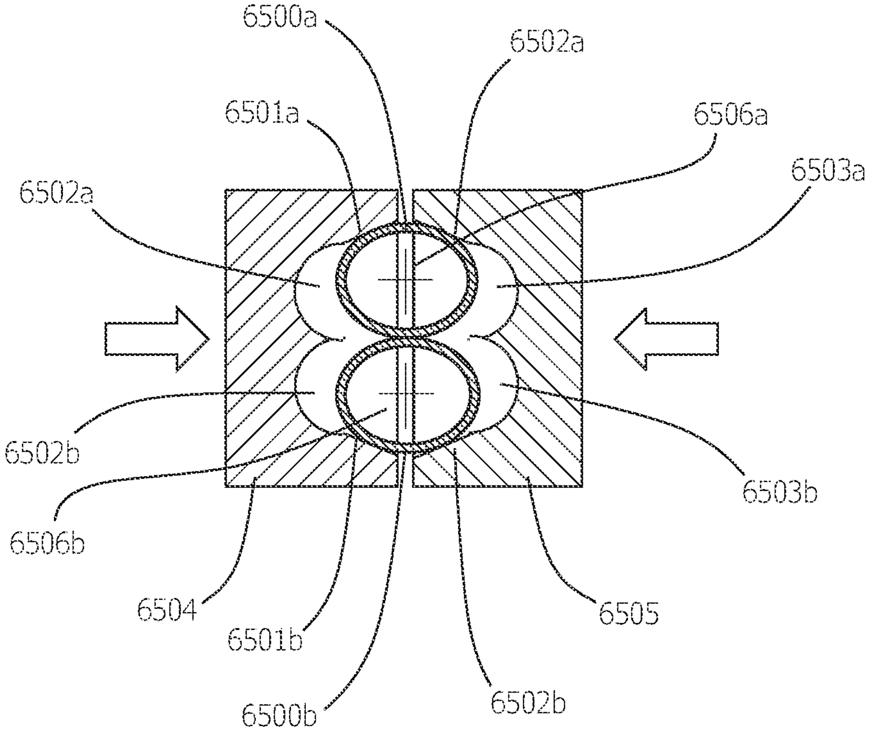
FIG. 65B illustrates further crimping of the branches of the bifurcated stent of FIG. 65A.
Figure 65C:
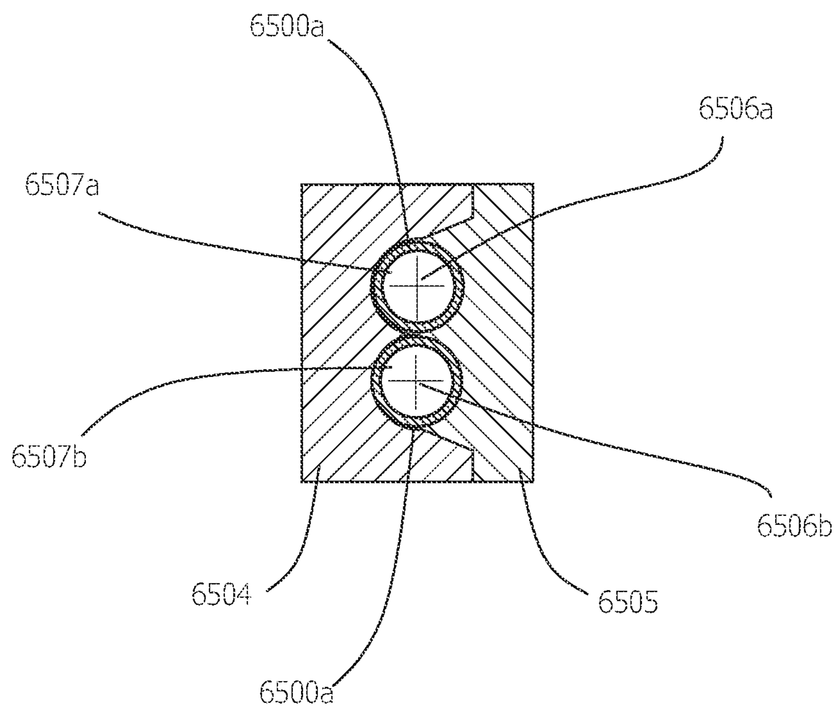
FIG. 65C illustrates further crimping of the branches of the bifurcated stent of FIG. 65A.

FIGS. 63-65 illustrate the mechanism of crimping a bifurcated stent onto a bifurcated balloon assembly using the crimping tool described herein. FIG. 63A shows uncrimped bifurcated stent (6300) placed onto bifurcated balloon assembly (6303). Bifurcated stent (6300) comprises main body stent (6301) and branch stents (6302*a-b*). FIG. 63B shows bifurcated stent (6300) and bifurcated balloon assembly (6303) of FIG. 63A placed into Part A (6304) of the bifurcated crimping tool. Branch stents (6302*a-b*) sit in branch channels (6305*a-b*), and main body stent (6301) sits in main channel (6306) of crimping tool (6304). FIGS. 64A-C illustrate the crimping process for the main body stent. At the start of the crimping process, uncrimped main body stent (6400) rests on shoulders (6403*a-b*, 6404*a-b*) of main channels (6405, 6406) of Part A (6401) and Part B (6402) as shown FIG. 64A. Moving Part A (6401) and Part B (6402) of the crimping tool toward each other forces main body stent (6400) to take on an oval shape and slide along shoulders (6403*a-b*, 6404*a-b*) into the floor of main channels (6405, 6406) as shown in FIG. 64B. FIG. 64C shows Part A (6401) and Part B (6402) fully interlaced. Main body stent (6400) is crimped radially toward its centerline (6407) into a circular cross-section conforming to circular channel (6408) formed by Part A (6401) and Part B (6402) of the crimping tool. FIGS. 65A-C illustrate the crimping process for branch stents (6500*a-b*). At the start of the crimping process, uncrimped branch stents (6500*a-b*) rest on outer shoulders (6501*a-b*, 6502*a-b*) of branch channels (6502*a-b*, 6503*a-b*) and contact each other at the center as shown in FIG. 65A. Moving Part A (6504) and Part B (6505) of the crimping tool toward each other forces branch stents (6500*a-b*) against each other and at the same time along outer shoulders (6501*a-b*, 6502*a-b*) into the floor of branch channels (6502*a-b*, 6503*a-b*) as shown in FIG. 65B. FIG. 65C shows Part A (6504) and Part B (6505) fully interlaced. Branch stents (6500*a-b*) are compressed radially inward toward their respective centerlines (6506*a-b*) into circular cross-sections conforming to circular channels (6507*a-b*) formed by Part A (6504) and Part B (6505) of the crimping tool. The crimping tool can be made from a polymer or a metal. The crimping tool can be made from polyethylene, nylon, ABS, aluminum, stainless steel, or a combination thereof. The crimping tool can be 3D printed, machined, or molded. The crimping tool can comprise heating elements to control the temperature of the crimping tool. The crimping tool can comprise additional openings to pass air for heating or cooling into the channels. The balloon assembly can be heated during the crimping process to increase the compliance of the balloon material. The balloon assembly can be heated to temperatures of between about 40° C. to about 60° C. The balloon assembly may be inflated during the crimping process to conform the balloon assembly to the crimped bifurcated stent.

Figure 66A:
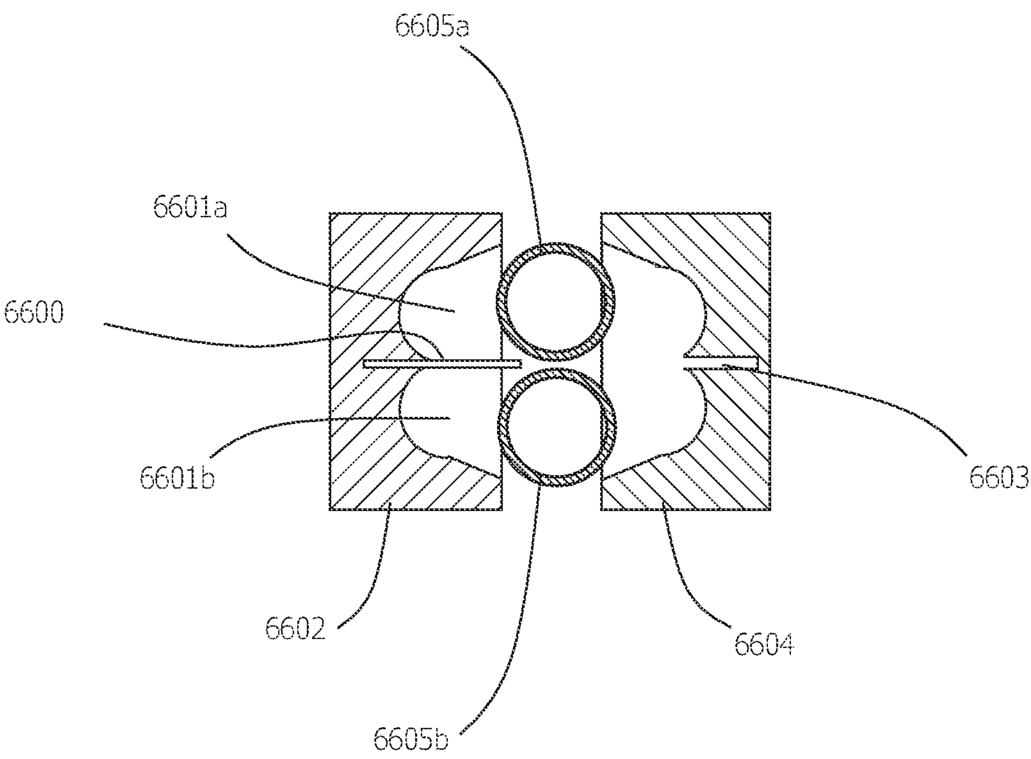
FIG. 66A illustrates crimping branches of a bifurcated stent with another embodiment of a crimping tool.
Figure 66B:
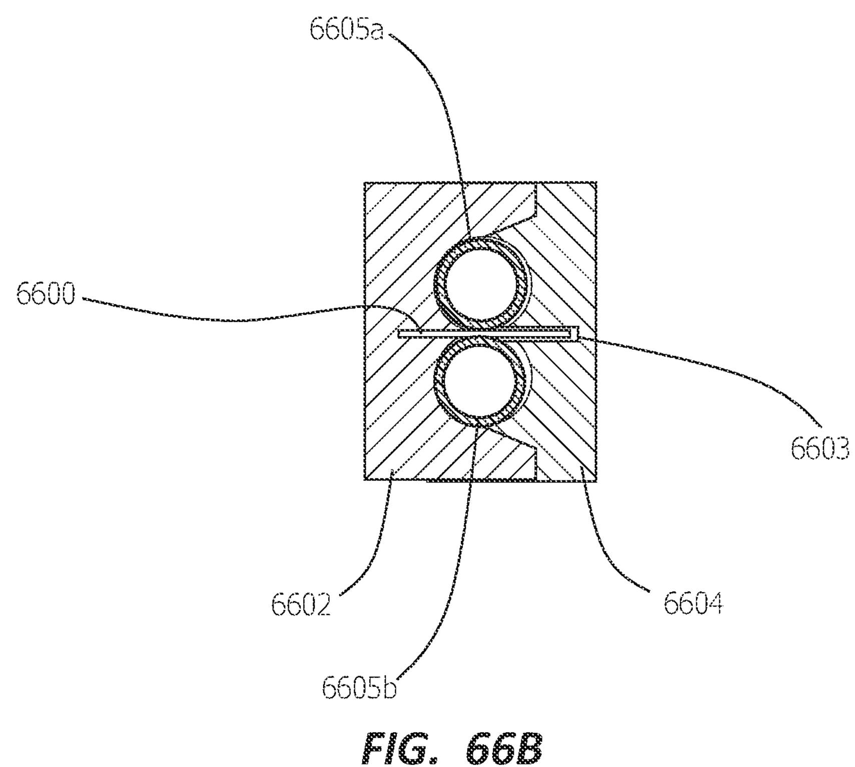
FIG. 66B illustrates further crimping of the branches of the bifurcated stent with the crimping tool of FIG. 66A.
Figure 67:
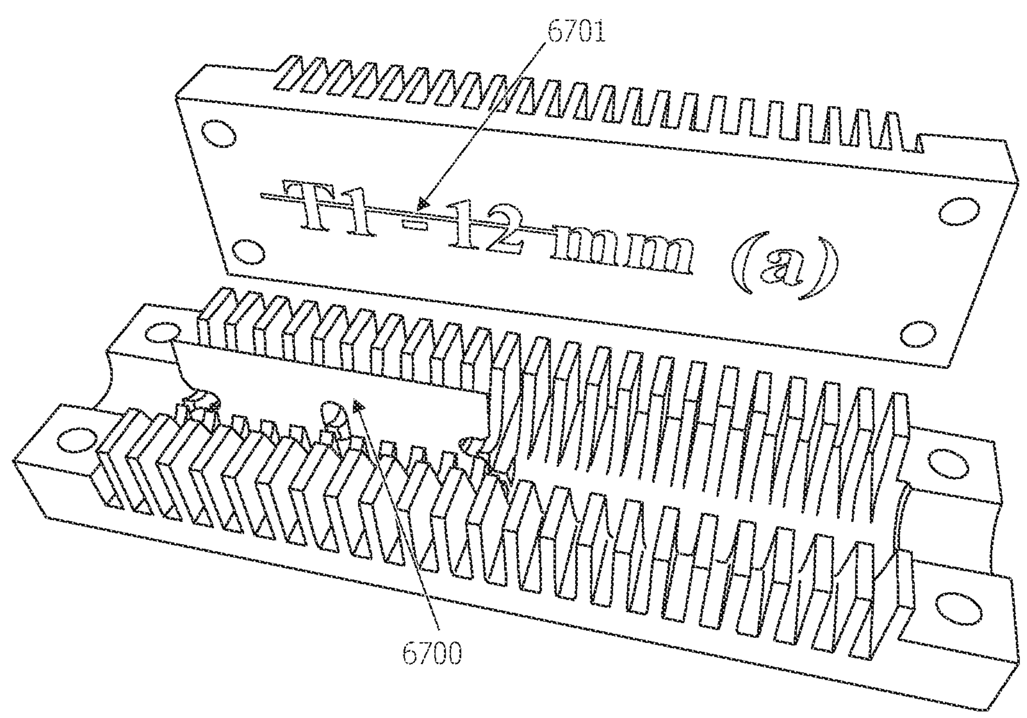
FIG. 67 shows a perspective view of another embodiment of a bifurcated crimping tool.
Figure 68:
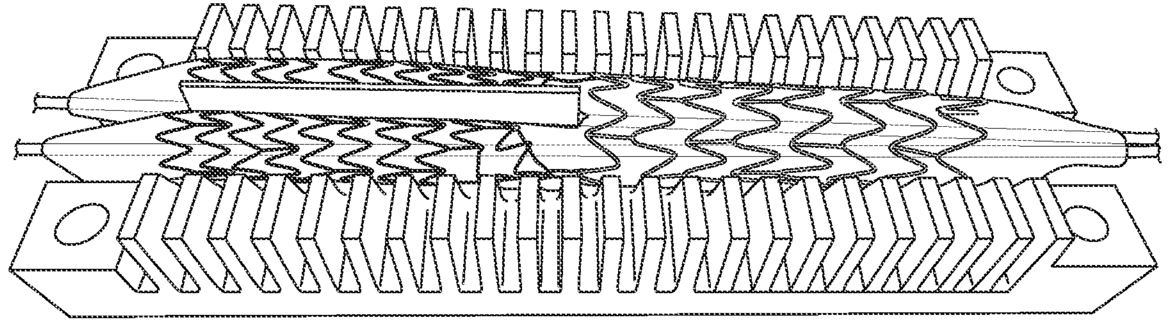
FIG. 68 shows a perspective view of a bifurcated stent system placed in another embodiment of a bifurcated crimping tool.

FIGS. 66A-B illustrate another embodiment of the crimping tool described herein. Septum (6600) is placed between branch channels (6601*a-b*) of Part A (6602) as shown in FIG. 66A. Septum (6600) slides into receiving slot (6603) in Part B (6604) when parts (6602, 6604) are interlaced as shown in FIG. 66B. Septum (6600) keeps branch stents (6605*a-b*) separated during the crimping process preventing branch stents (6605*a-b*) from crossing the centerline and interfering with each other. FIG. 67 shows a 3D printed crimping tool with septum (6700) in Part A and receiving slot (6701) in Part B. FIG. 68 shows a bifurcated stent on a bifurcated balloon assembly placed into Part A of FIG. 67.

Figure 69:
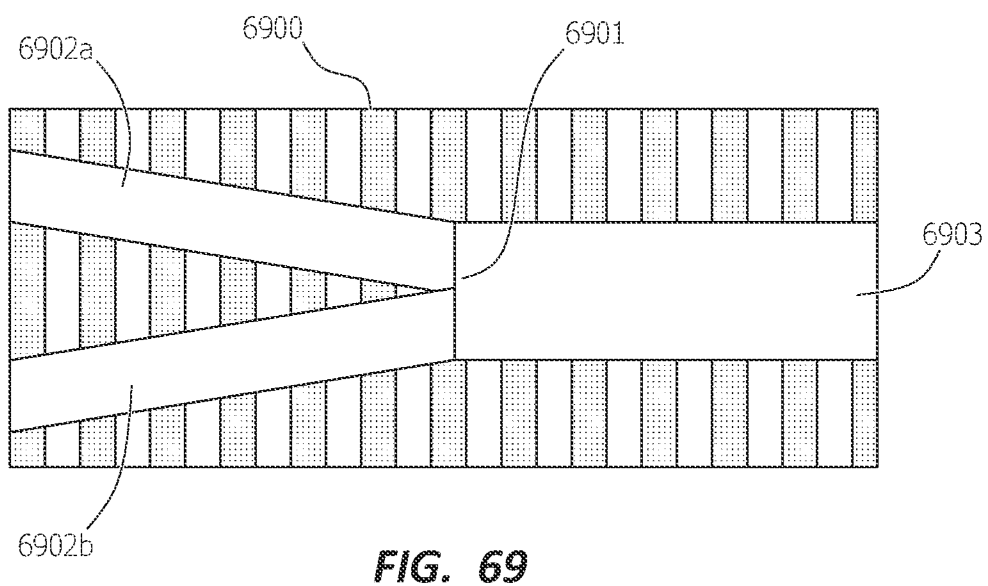
FIG. 69 illustrates another embodiment of bifurcated channels in a crimping tool.
Figure 70:
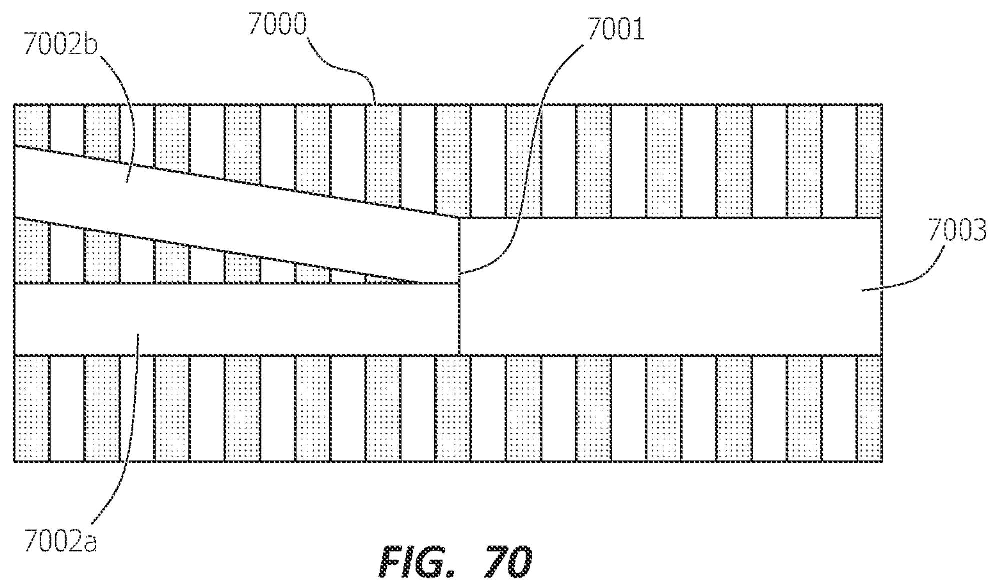
FIG. 70 illustrates yet another embodiment of bifurcated channels in a crimping tool.

FIGS. 69-70 illustrate other embodiments of the crimping tool described herein. FIG. 69 shows crimping tool (6900) comprising bifurcated flow channel (6901) with branch channels (6902*a-b*) that are arranged at an angle to the axis of main channel (6903). FIG. 70 shows crimping tool (7000) comprising asymmetric bifurcated channel (7001). Second branch channel (7002*b*) is oriented at an angle to first branch channel (7002*a*) and main channel (7003).

Figure 71:
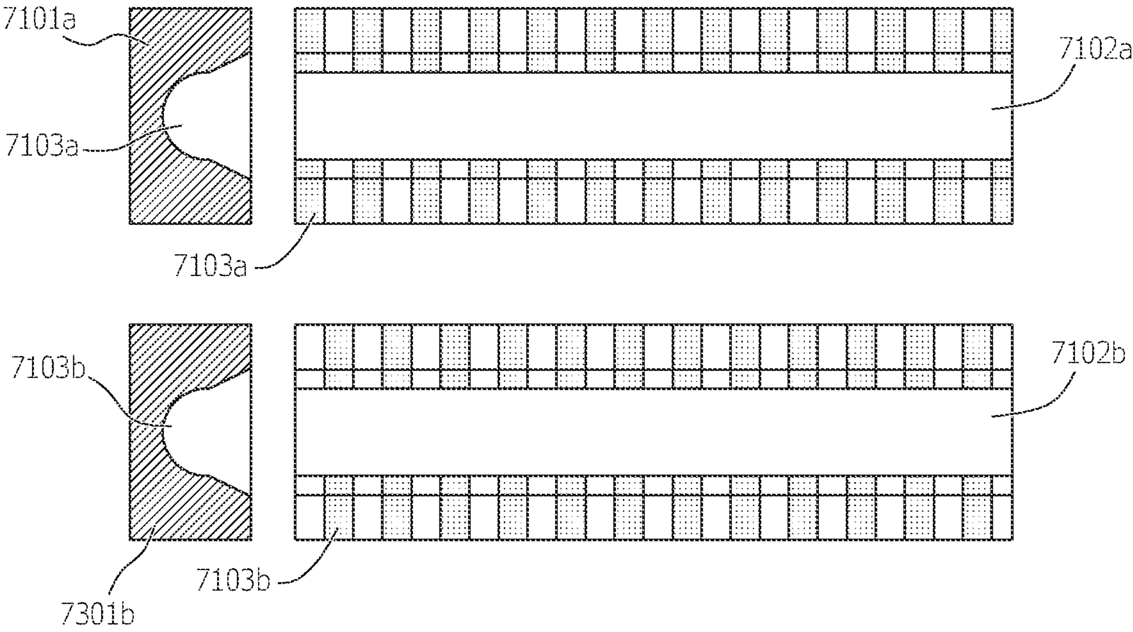
FIG. 71 illustrates a single-channel crimping tool described herein.
Figure 72:
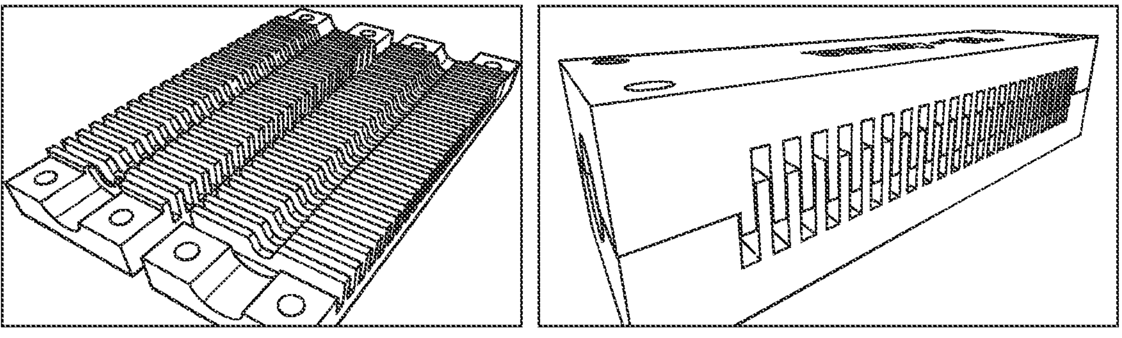
FIG. 72 illustrates a perspective view of a single-channel crimping tool.
Figure 73A:
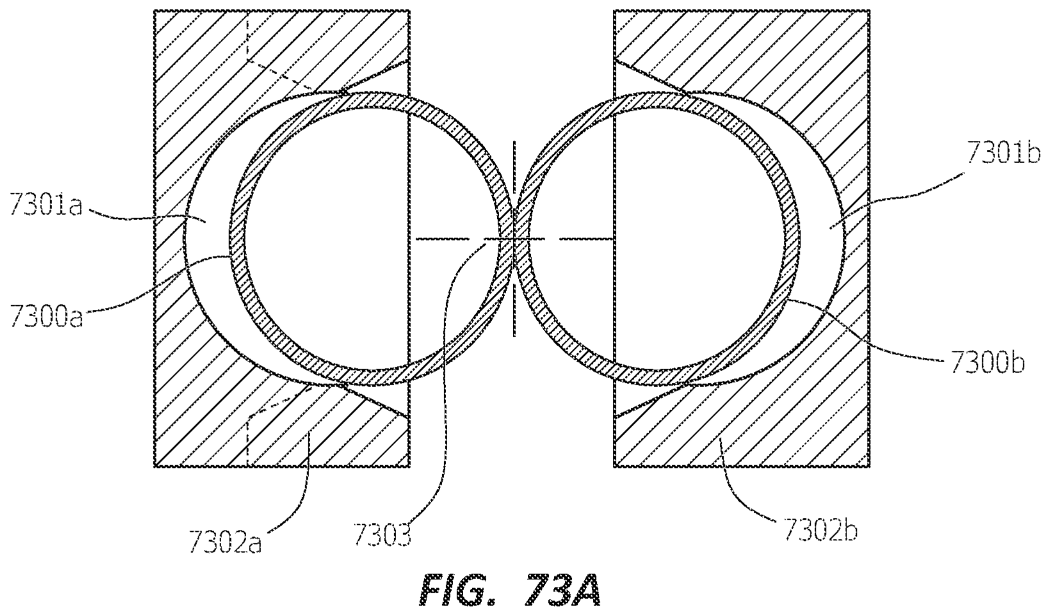
Figure 73B:
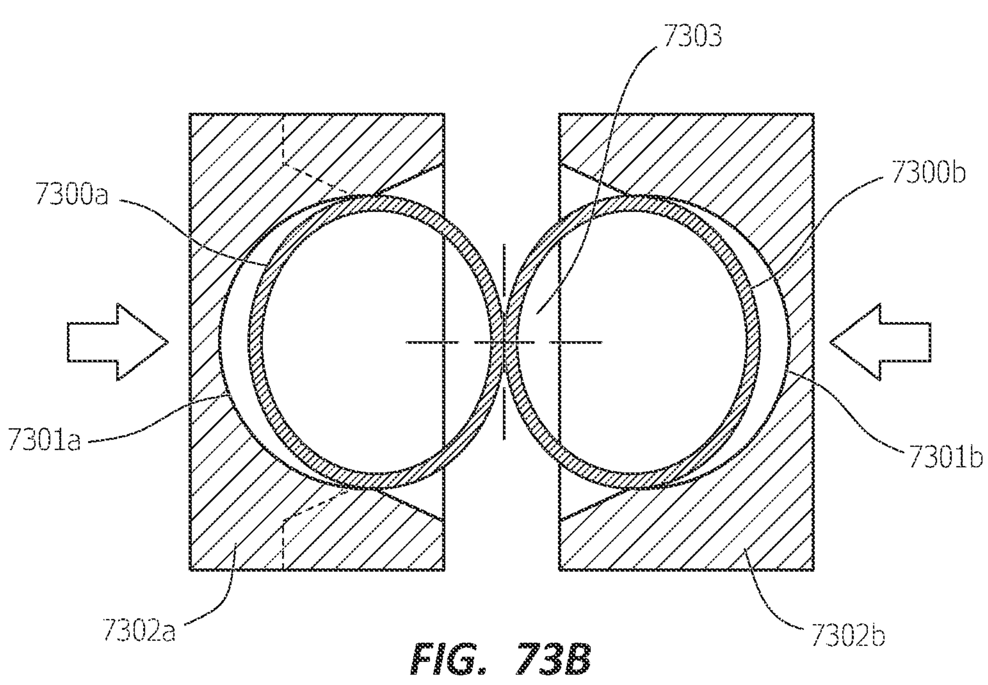
Figure 73C:
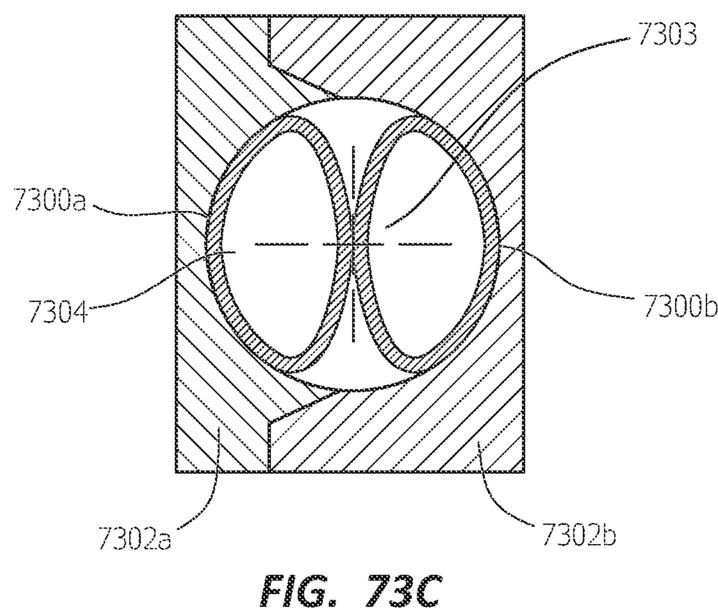

FIG. 71 illustrates an embodiment of the crimping tool for the second step of the crimping method described herein. Part A (7101*a*) and Part B (7101*b*) each comprise single channel (7102*a-b*) along the main axis of parts (7101*a-b*) and ribs (7103*a-b*) arranged perpendicular to the main axis. The floors of channels (7103*a-b*) have a half-circular cross-section. FIG. 72 shows perspective views of the single-channel crimping tool. The crimping process for the main body stent in the single-channel crimping tool is identical to that in the bifurcated crimping tool (see FIGS. 64A-C). The crimping process for the branch stent is different from that in the bifurcated crimping tool. FIGS. 73A-C illustrate the crimping process for the two branch stents. Branch stents (7300*a-b*) are placed into channels (7301*a-b*) of Part A (7302*a*) and Part B (7302*b*) of the crimping tool as shown in FIG. 73A. Branch stents (7300*a-b*) contact each other along centerline (7303) of the crimping tool. Moving Part A (7302*a*) and Part B (7302*b*) of the crimping tool toward each other forces branch stents (7300*a-b*) against each other, and at the same time pushes branch stents (7300*a-b*) into the floors of channels (7301*a-b*). Branch stents (7300*a-b*) are compressed inward toward common centerline (7303). FIG. 73C shows branch stents (7300*a-b*) in the crimped configuration. Branch stents (7300*a-b*) take on non-circular, generally oval shapes within circular channel (7304) formed by Part A (7302*a*) and Part B (7302*b*) of the crimping tool.

Figure 74:
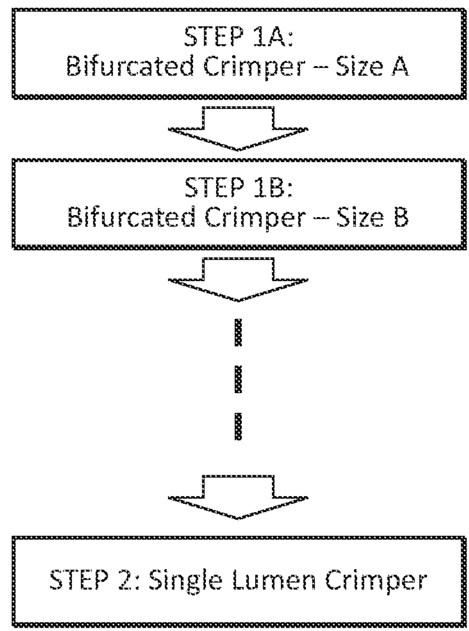
Figure 74:
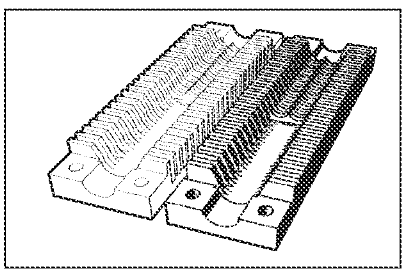
Figure 74:
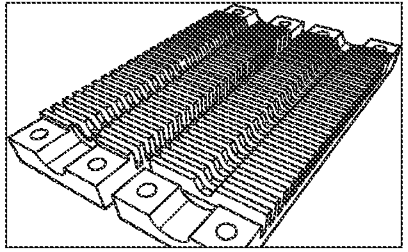
Figure 74:
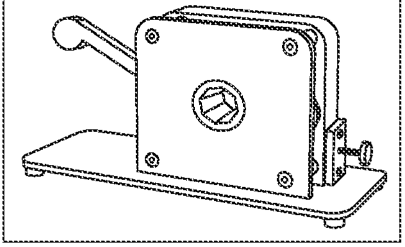
Figure 74:
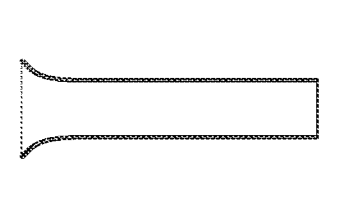

In some embodiments, in a first step of the crimping process, the main body is compressed inward toward its centerline and the branch stents are compressed inward toward their respective centerlines. In some embodiments, in the second step of the crimping process, the main body stent and the two branch stents are compressed inward toward a common centerline. FIG. 74 shows an exemplary flow chart of the crimping process described herein. In other embodiments, in a first step of the crimping procedure, the bifurcated stent is crimped by a crimping tool with a bifurcated channel. In some embodiments, a single bifurcated crimping tool is not sufficient to crimp the bifurcated stent from the un-crimped configuration into the desired final crimp configuration of the first step Such that the first step requires more than one crimping tools. In other embodiments, a single bifurcated crimping tool is sufficient. Several bifurcated crimping tools with progressively narrower channels can be used to reach the final crimped configuration of the bifurcated stent at the end of the first step. For example, the uncrimped main body of the bifurcated stent can have a diameter of about 13 mm and the uncrimped branch stents can have diameters of about 7 mm. A first bifurcated crimping tool (Size A) can have a main channel floor diameter of about 12 mm, and the two branch channels can have floor diameters of about 6 mm. The first bifurcated crimping tool compresses the main body stent to a diameter of about 12 mm and the branch stents to a diameter of about 6 mm. A second bifurcated crimping tool (Size B) can have a main channel floor diameter of about 10 mm, and the two branch channels can have floor diameters of about 5 mm. The second crimping tool compresses the main body stent to a diameter of about 10 mm and the branch stents to a diameter of about 5 mm. A third bifurcated crimping tool (Size C) can have a main channel floor diameter of about 8 mm, and the two branch channels can have floor diameters of about 4 mm. The third crimping tool can compress the main body stent to a diameter of about 8 mm and the branch stents to a diameter of about 4 mm. The number of bifurcated crimping tools used to complete the first step of the crimping procedure can be 1, 2, 3, 4 or more. The second step of the crimping process described herein can be accomplished with a single-channel interlacing crimping tool described herein (bottom left image of FIG. 74). Similar to the first step, a series of single-channel crimping tools with progressively smaller lumens may be used to reach the desired final crimped diameter of the bifurcated stent. In some embodiments, the second step can be accomplished by a standard radial crimper (bottom middle of FIG. 74). In other embodiments, the second step can be accomplished by a loading tube or a series of loading tubes with progressively smaller lumen diameters (bottom right of FIG. 36).

It is understood that the bifurcated channels in the crimping tool can take on various shapes and geometries. The crimping tool can comprise of more than two parts. The crimping tool can comprise of a pair of interlacing parts for crimping the main body stent and a pair of interlacing parts for crimping the branch stents. In some embodiments, the crimping tool comprises three pairs of interlacing parts for crimping the main body stent and the two branch stents respectively. In other embodiments, the crimping tool can comprise only two channels for crimping the branch stents. The main body stent can be crimped separately by a radial crimper. It is further understood that the crimping process can comprise more steps than the two crimping steps described herein. The crimping procedure can include a step of heating the bifurcated balloon assembly to increase the pliability of the balloon material during the crimping process. The crimping process can include inflation of the bifurcated balloon assembly during or at the end of each crimping step to conform the bifurcated balloon assembly to the shape of the crimped bifurcated stent. The crimping process can include heating and inflating the bifurcated balloon assembly at the same time.

In some embodiments a balloon catheter for treating a diseased bifurcating blood vessel is described. The balloon catheter comprises: a proximal hub; a shaft having a proximal shaft and a distal shaft; a distal hub; and a bifurcated balloon assembly comprising a first balloon having a proximal segment and a distal segment, and a second balloon having a proximal segment and a distal segment, wherein the first balloon and the second balloon are arranged substantially in parallel, and wherein the proximal segment of the first balloon is connected to the proximal shaft, the distal segment of the first balloon is connected to the distal hub, and the distal segment of the second balloon is connected to the distal hub.

In other embodiments, the balloon catheter further comprises a first guidewire lumen and a second guidewire lumen. The first guidewire lumen can extend from the proximal hub through the shaft, the first balloon, and the distal hub, and the second guidewire lumen can extend from the proximal hub through the shaft, the distal hub, and the second balloon.

In some embodiments, the balloon catheter further comprises a restraining sleeve. The distal segments of the first and the second balloon are constrained by the restraining sleeve.

In other embodiments, the first balloon and the second balloon can be non-compliant while the restraining sleeve can be compliant. The first balloon and the second balloon can comprise a waist that is located between the distal segment and the proximal segment of each balloon.

In some embodiments, the proximal segments of the balloons have a substantially constant diameter along their lengths and the distal segments of the balloons have a varying diameter along their lengths.

In other embodiments a balloon catheter for treating a diseased bifurcating blood vessel is described. The balloon catheter comprises: a proximal hub; a shaft having a proximal shaft and a distal shaft; a distal hub; and a bifurcated balloon assembly comprising a first balloon having a proximal end and a distal end, and a second balloon having a proximal end and a distal end, wherein the first balloon and the second balloon are arranged substantially in parallel, and wherein the proximal end of the first balloon is connected to the proximal shaft, the distal end of the first balloon is connected to the distal hub, and the distal end of the second balloon is connected to the distal hub.

In some embodiments, the balloons have a proximal end and a distal end. Balloons including ends can be balloons that do not have waists. In other embodiments, the balloons have a proximal segment and a distal segment. Balloons including segments can have waists.

In other embodiments, a method for deploying a bifurcated stent comprising a main body stent having a proximal end and a distal end, and two branch stents is described. In some embodiments, the method can be performed in at least two steps. The first step can comprise expanding the two branch stents and the main body stent with two parallel balloons. The second step can comprise further expanding the main body stent with a single balloon. It should be noted that more than two steps be used. In some embodiments, both steps can merge into one step.

In some embodiments, the first step can expand the branch stents to circular cross-sections and the main body stent to an oval cross-section. In other embodiments, the second step can decreases the ovality of the distal end of the main body stent.

In other embodiments, a method for crimping a balloon expandable bifurcated stent is described. The method of crimping a balloon-expandable bifurcated stent can comprise a main body stent and two branch stents onto a bifurcated balloon assembly. The method can comprise at least two steps. A first step during which the main body stent and the two branch stents are compressed inward toward their respective centerlines, and a second step in which the main body stent and the two branch stents are compressed toward a common centerline. It should be noted that there could be additional steps to perform this method. In some embodiments, the method can merge steps 1 and 2 into one step. The branch stents can be compressed to an oval cross-section and the main body stent is compressed to a circular cross-section. In the first step the bifurcated stent can be placed into a crimping tool with a bifurcating channel.

The preceding disclosures are illustrative embodiments. It should be appreciated by those of skill in the art that the devices, techniques and methods disclosed herein elucidate representative embodiments that function well in the practice of the present disclosure. However, those of skill in the art should, in light of the present disclosure, appreciate that many changes can be made in the specific embodiments that are disclosed and still obtain a like or similar result without departing from the spirit and scope of the invention.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects those of ordinary skill in the art to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A balloon catheter for treating a diseased bifurcating blood vessel, the balloon catheter comprising:

a proximal hub;

a shaft;

a distal hub;

a bifurcated balloon assembly comprising a first balloon having a proximal segment and a distal segment, and a second balloon having a proximal segment and a distal segment; and a first guidewire lumen and a second guidewire lumen, wherein the first balloon and the second balloon are arranged substantially in parallel, wherein the proximal segment of the first balloon is connected to the shaft, the distal segment of the first balloon is connected to the distal hub, and the distal segment of the second balloon is connected to the distal hub, and wherein the first guidewire lumen extends from the proximal hub through the shaft, the first balloon, and the distal hub, and the second guidewire lumen extends from the proximal hub through the shaft, the first balloon, the distal hub, and the second balloon.

2. The balloon catheter of claim 1, wherein the distal segments of the first and the second balloon are constrained by a restraining sleeve.

3. The balloon catheter of claim 2, wherein the first balloon and the second balloon are non-compliant and the restraining sleeve is compliant.

4. The balloon catheter of claim 2, wherein the restraining sleeve is tapered with a larger diameter on a distal end of the restraining sleeve than on a proximal end of the restraining sleeve.

5. The balloon catheter of claim 1, wherein the first balloon and the second balloon comprise a waist that is located between the distal segment and the proximal segment of each balloon.

6. The balloon catheter of claim 5, wherein the proximal segment of each balloon has a substantially constant diameter along its length and the distal segment of each balloon has a varying diameter along its length.

7. The balloon catheter of claim 1, wherein the shaft has a proximal shaft and a distal shaft, and wherein the bifurcated balloon assembly is disposed between the proximal shaft and the distal shaft.

8. The balloon catheter of claim 1, wherein the second guidewire lumen terminates at an opening at a proximal end of the second balloon.

9. The balloon catheter of claim 1, further comprising a tether that extends through an opening in the shaft that is proximal to the bifurcated balloon assembly and couples to a proximal end of the second balloon.

10. The balloon catheter of claim 1, further comprising:

a first flexible conduit that couples the first balloon to the distal hub; and a second flexible conduit that couples the second balloon to the distal hub.

11. A method of deploying a bifurcated stent from a balloon catheter for treating a diseased bifurcating blood vessel, the balloon catheter comprising:

a proximal hub;

a shaft;

a distal hub;

a bifurcated stent crimped to a bifurcated balloon assembly, the bifurcated balloon assembly comprising a first balloon having a proximal segment and a distal segment, and a second balloon having a proximal segment and a distal segment;

a first guidewire lumen and a second guidewire lumen;

a first guidewire that extends through the first guidewire lumen and exits a distal end of the balloon catheter; and a second guidewire that extends through the second guidewire lumen through the shaft, the first balloon, and the distal hub and then exits a first opening of the distal hub to form a loop distal to the distal hub and the second guidewire enters a second opening of the distal hub and extends through the second guidewire lumen to the second balloon and exits a proximal end of the second balloon, wherein the bifurcated stent comprises a main body stent having a proximal end and a distal end and two branch stents in at least two steps, wherein a first step comprises expanding the two branch stents and the main body stent with the first and second balloons.

12. The method of claim 11, wherein the first step expands the branch stents to circular cross-sections and the main body stent to an oval cross-section.

13. The method of claim 11, wherein a second step decreases ovality of the distal end of the main body stent by expanding the main body stent with a third balloon.

14. A method of crimping a balloon-expandable bifurcated stent comprising a main body stent and two branch stents onto a bifurcated balloon assembly of a balloon catheter for treating a diseased bifurcating blood vessel, the balloon catheter comprising:

a proximal hub;

a shaft;

a distal hub;

the bifurcated balloon assembly comprising a first balloon having a proximal segment and a distal segment, and a second balloon having a proximal segment and a distal segment; and a first guidewire lumen and a second guidewire lumen, wherein the first balloon and the second balloon are arranged substantially in parallel, wherein the proximal segment of the first balloon is connected to the shaft, the distal segment of the first balloon is connected to the distal hub, and the distal segment of the second balloon is connected to the distal hub, wherein the first guidewire lumen extends from the proximal hub through the shaft, the first balloon, and the distal hub, and the second guidewire lumen extends from the proximal hub through the shaft, the first balloon, the distal hub, and the second balloon, and wherein the method comprises of a first step in which the main body stent and the two branch stents are compressed inward toward their respective centerlines, and a second step in which the main body stent and the two branch stents are compressed toward a common centerline.

15. The method of claim 14, wherein the branch stents are compressed to an oval cross-section and the main body stent is compressed to a circular cross-section.

16. The method of claim 14, wherein in the first step the bifurcated stent is placed into a crimping tool with a bifurcating channel.

* * * * *